(12) United States Patent
Morrell et al.

(10) Patent No.: US 8,603,980 B2
(45) Date of Patent: Dec. 10, 2013

(54) GLUTAMATE RECEPTOR ANTAGONISTS AND METHODS OF USE

(75) Inventors: Craig N. Morrell, Brighton, NY (US); Charles J. Lowenstein, Pittsford, NY (US)

(73) Assignee: The Johns Hopkins University, Baltimore, MD (US)

( * ) Notice: Subject to any disclaimer, the term of this patent is extended or adjusted under 35 U.S.C. 154(b) by 423 days.

(21) Appl. No.: 12/523,437

(22) PCT Filed: Jan. 16, 2008

(86) PCT No.: PCT/US2008/000559
§ 371 (c)(1),
(2), (4) Date: Apr. 14, 2010

(87) PCT Pub. No.: WO2008/088820
PCT Pub. Date: Jul. 24, 2008

(65) Prior Publication Data
US 2010/0196354 A1    Aug. 5, 2010

Related U.S. Application Data

(60) Provisional application No. 60/880,655, filed on Jan. 16, 2007.

(51) Int. Cl.
*A61K 38/00* (2006.01)
*A61K 31/00* (2006.01)

(52) U.S. Cl.
USPC ............. 514/14.9; 514/1.1; 514/80; 514/247

(58) Field of Classification Search
None
See application file for complete search history.

(56) References Cited

U.S. PATENT DOCUMENTS

| | | | |
|---|---|---|---|
| 5,395,822 A | 3/1995 | Izumi et al. | |
| 5,719,152 A | 2/1998 | Nagata et al. | |
| 6,057,454 A | 5/2000 | Aloup et al. | |
| 6,921,775 B2 * | 7/2005 | Jensen et al. | 514/455 |
| 2008/0194519 A1 * | 8/2008 | Cloyd | 514/58 |

FOREIGN PATENT DOCUMENTS

| | | |
|---|---|---|
| WO | WO-97/32873 A1 | 9/1997 |
| WO | WO-02/064085 A2 | 8/2002 |
| WO | WO-03/041697 A1 | 5/2003 |

OTHER PUBLICATIONS

Chang Y. et al. "Mechanisms involved in the antiplatelet activity of ketamine in human platelets." J Biomed Sci. Nov.-Dec. 2004;11(6):764-72.
Erdo F., et al. "The AMPA-antagonist talampanel is neuroprotective in rodent models of focal cerebral ischemia." Brain Res Bull. Jul. 15, 2005;66(1):43-9.
Macdonald AG., et al. "Single channel analysis of ketamine interaction with a quisqualate receptor." Eur J Pharmacol. Jan. 21, 1992;210(3):223-9.
Matucz E., et al. "Reduction of cerebral infarct size by non-competitive AMPA antagonists in rats subjected to permanent and transient focal ischemia." Brain Res. Sep. 3, 2004;1019(12):210-6.
Meden P., et al. "Enhancing the efficacy of thrombolysis by AMPA receptor blockade with NBQX in a rat embolic stroke model." J Neurol Sci. Nov. 1993;119(2):209-16.
Page R.L. II, et al. "Intractable epistaxis associated with topiramate administration." Ann Pharmacother. Jul.-Aug. 2006;40(7-8):1462-5.
Physcans' Desk Reference entry for AGGRASTAT (tirofiban hydrochloride), May 2002, pp. 1-14 of 14, especially p. 1, "Description".
Suzuki M. et al. Neuroprotective effects of YM872 coadministered with t-PA in a rat embolic stroke model. Brain Res. Jan. 3, 2003;959(1):169-72.
Topiramate package insert downloaded from http://www.drugs.com/pro/topiramate.html, published Oct. 2006, pp. 1-34 of 34, especially p. 2, "Mechanism of Action".
Vitamin K (MEPHYTON) description downloaded from http://www.medicinenet.com, Mar. 2005, pp. 1-2 of 2.
Yao H., et al. "AMPA receptor antagonist, YM90K, reduces infarct volume in thrombotic distal middle cerebral artery occlusion in spontaneously hypertensive rats." Brain Res. Apr. 4, 1997;753(1):80-5.
Supplementary European Search Report issued May 25, 2011 and mailed Jun. 1, 2011 for European Patent Application No. EP 08713155.3.
Internation Search Report issued Aug. 13, 2008 and mailed Sep. 17, 2008 for PCT Application No. PCT/US08/00559.

* cited by examiner

*Primary Examiner* — Christine J Saoud
*Assistant Examiner* — Jon M Lockard
(74) *Attorney, Agent, or Firm* — Edwards Wildman Palmer LLP; Peter F. Corless; Richard B. Emmons

(57) ABSTRACT

The present invention relates to methods and compositions for modulating platelet activity by inhibiting or activating glutamate receptors. The invention further relates to preventing or treating thrombotic diseases.

6 Claims, 19 Drawing Sheets

Figure 1
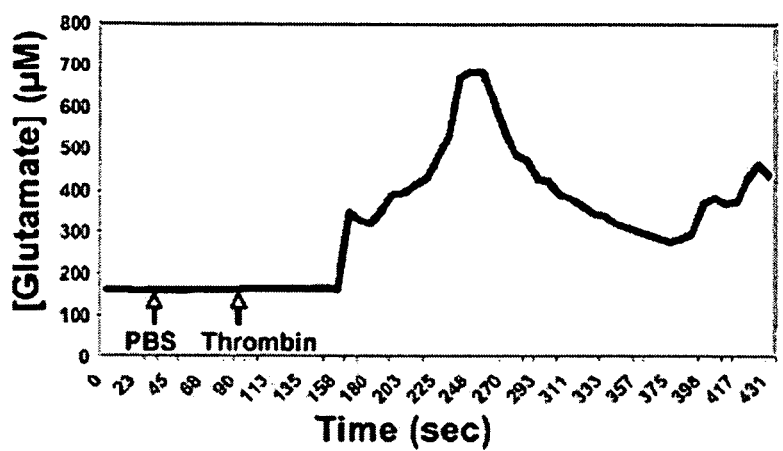
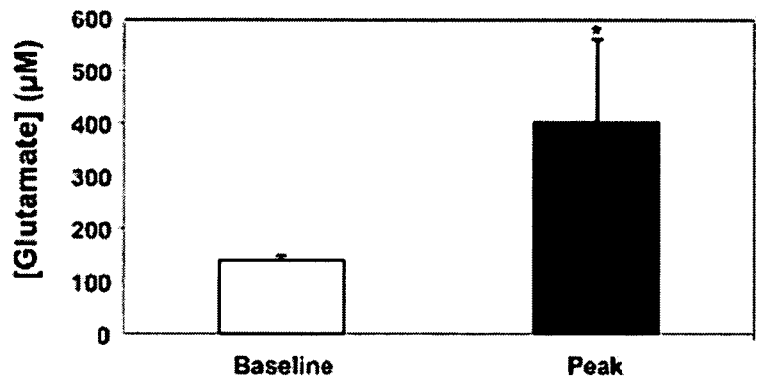

Figure 2
A. 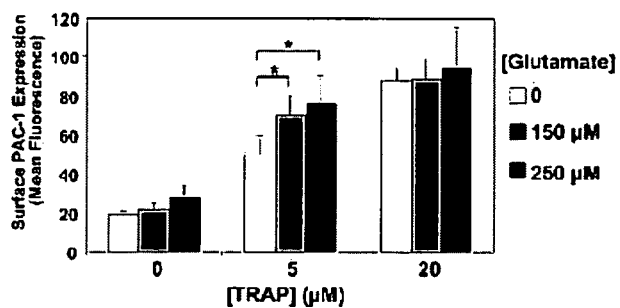
B. 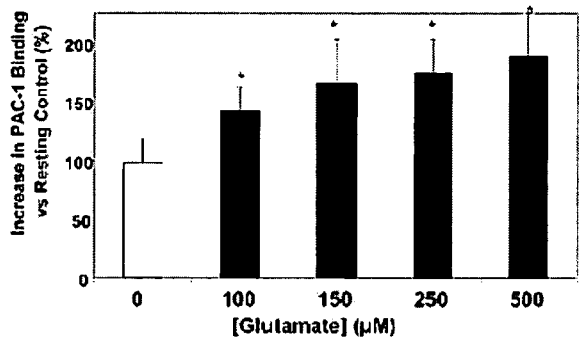
C. 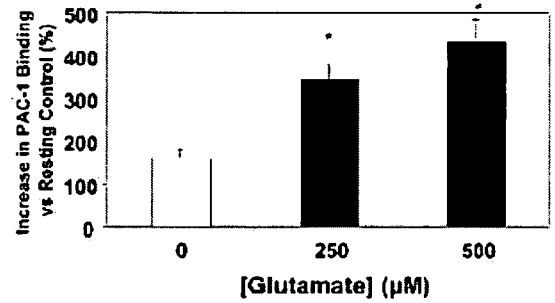
D. 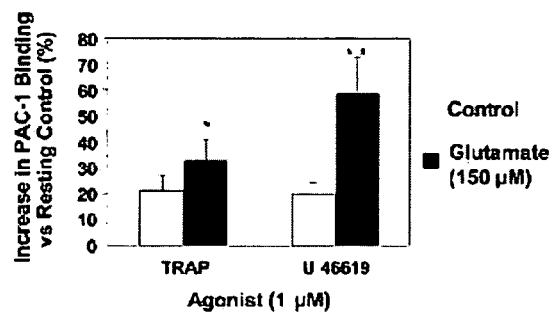

Figure 3
A.
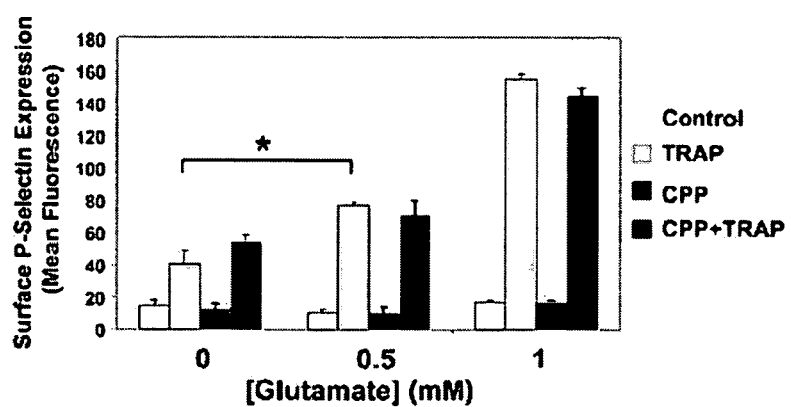
B.
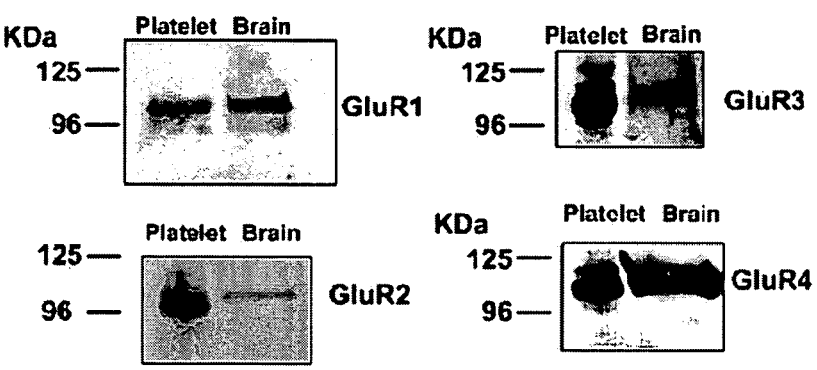
C.
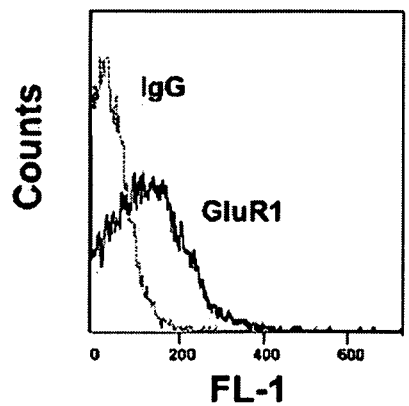

Figure 5
A. 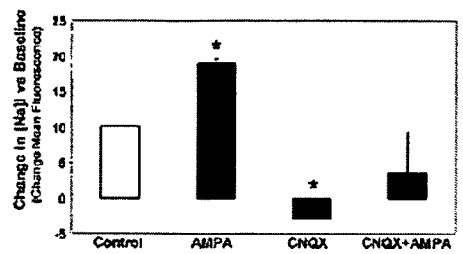
B. 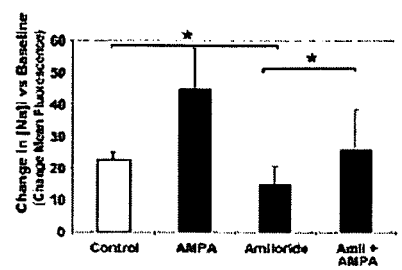
C. 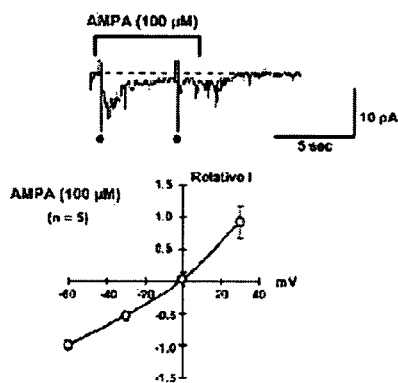
D. 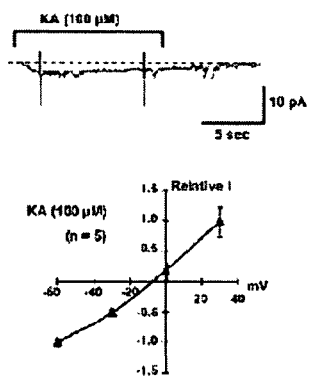
E. 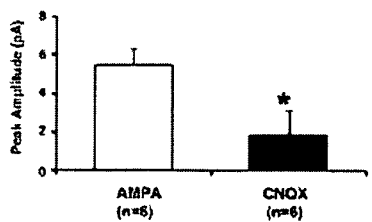
F. 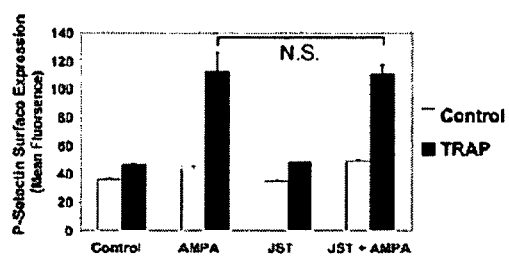

Figure 6
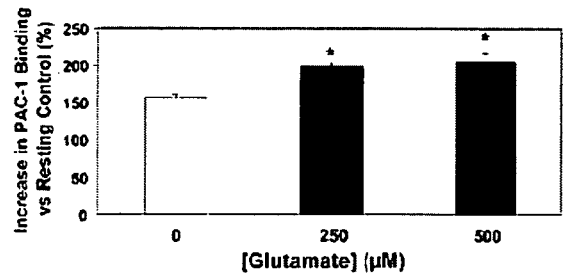
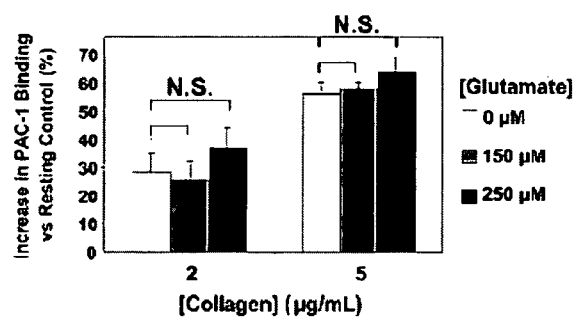
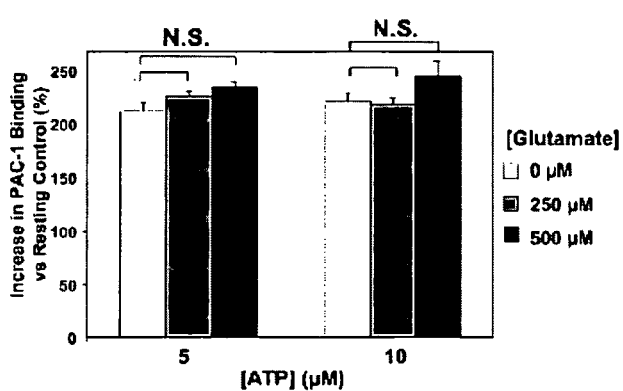
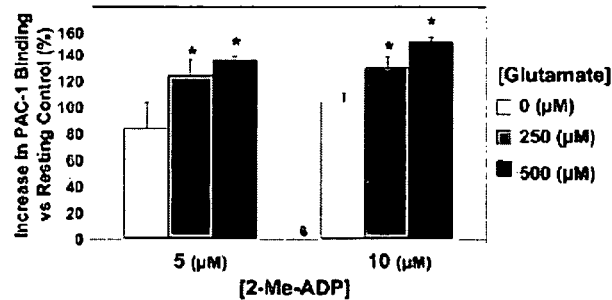

Figure 7
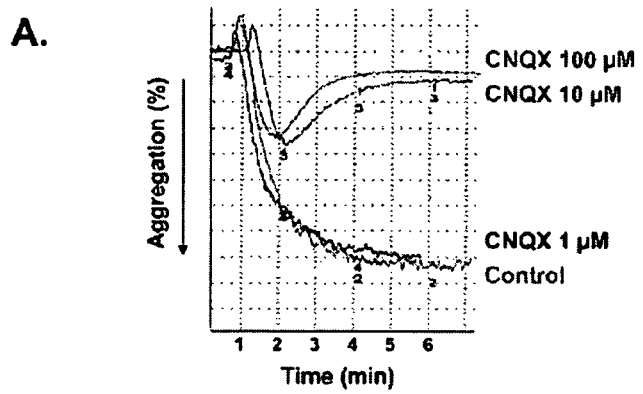
A.
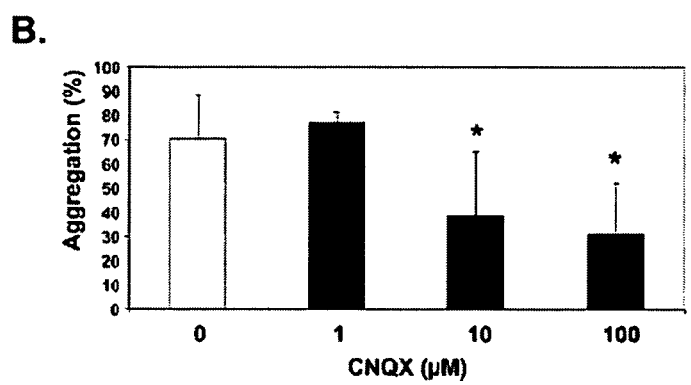
B.
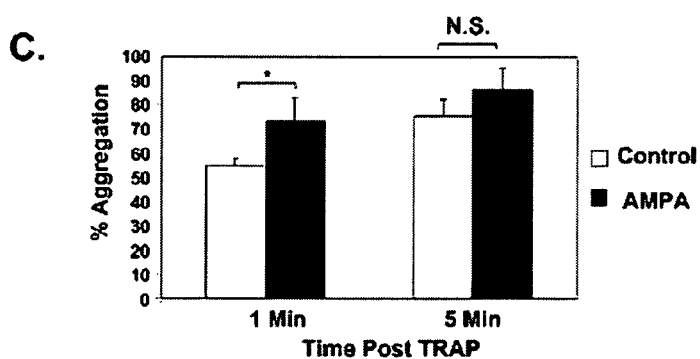
C.

Figure 9 (1/5)
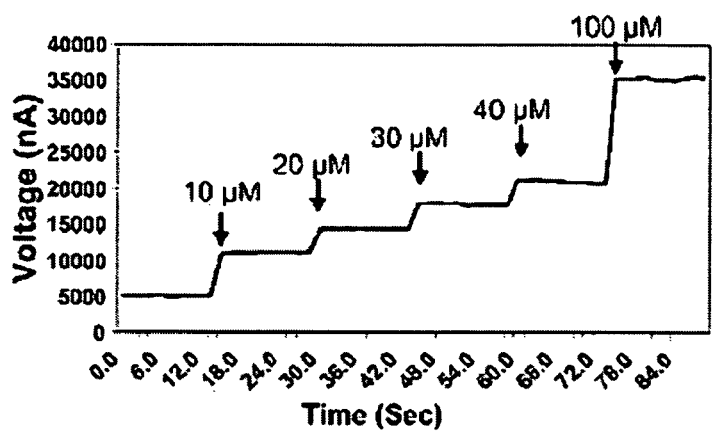
A.
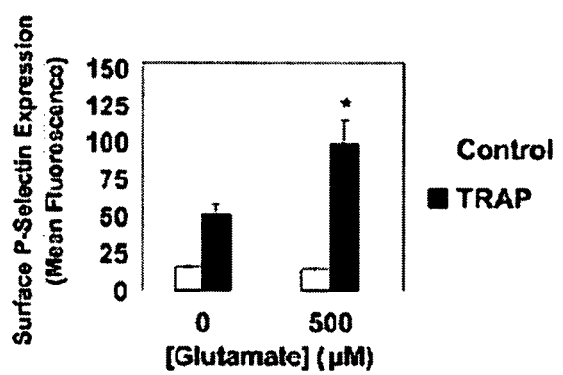
B.
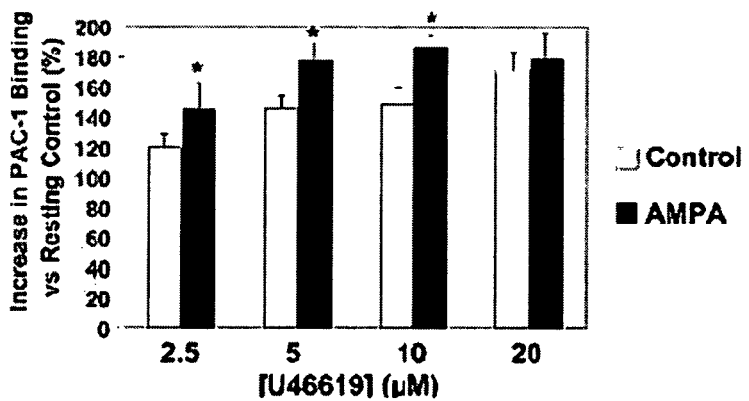
C.

Figure 9 (2/5)
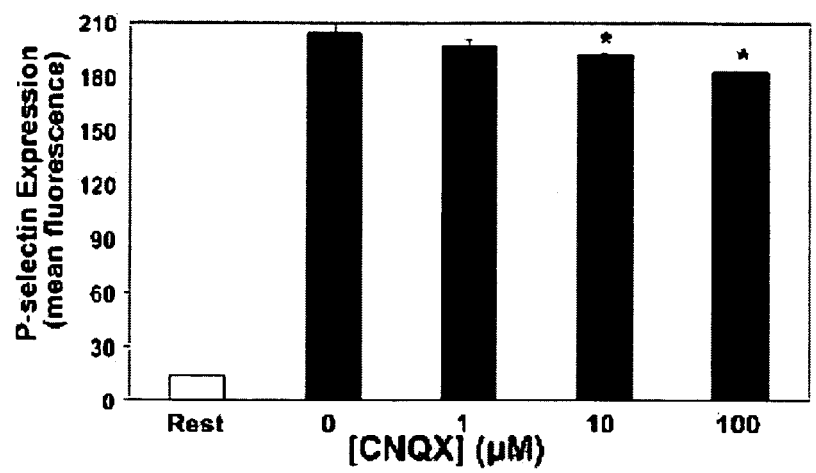
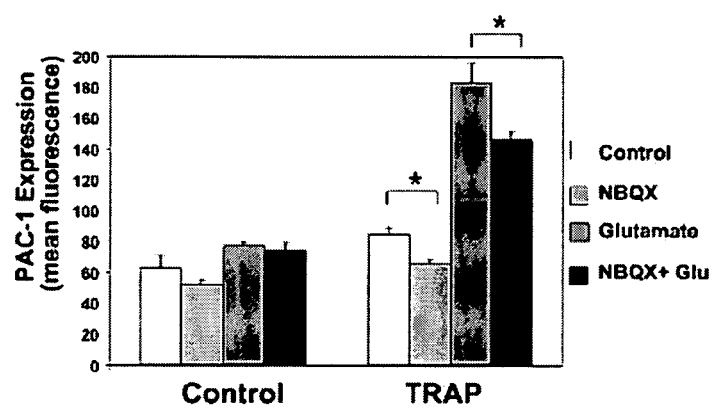
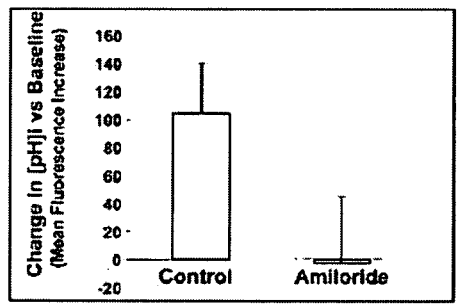

Figure 9 (3/5)
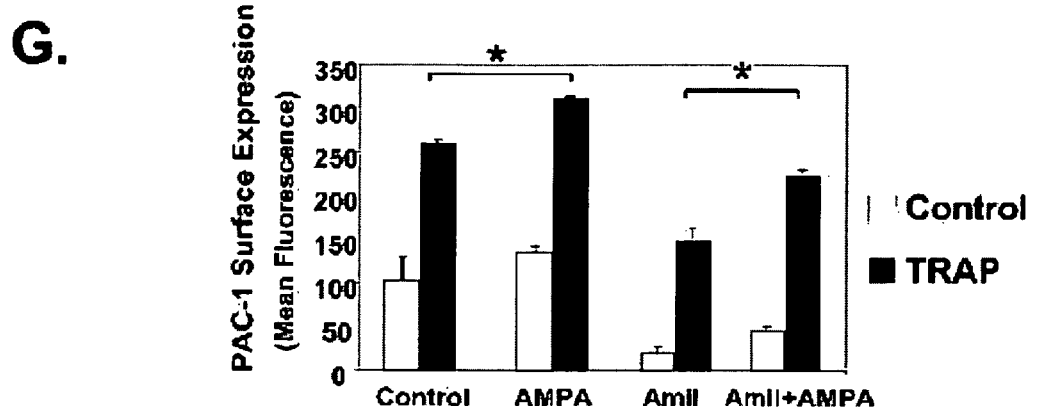

Figure 9 (4/5)
H.
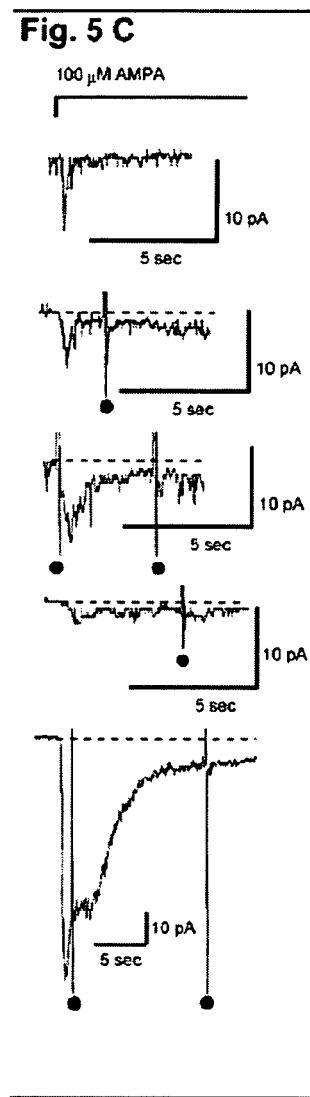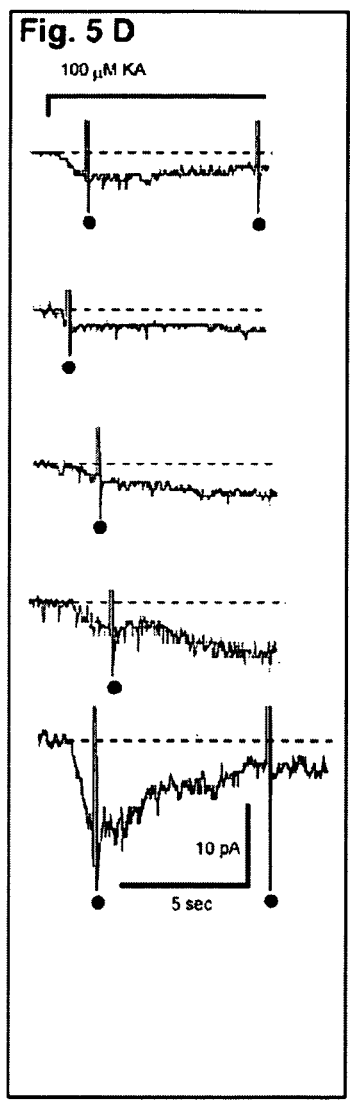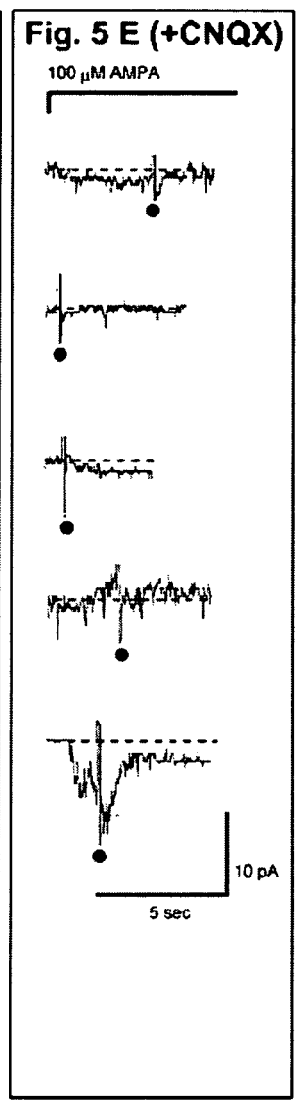

Figure 9 (5/5)
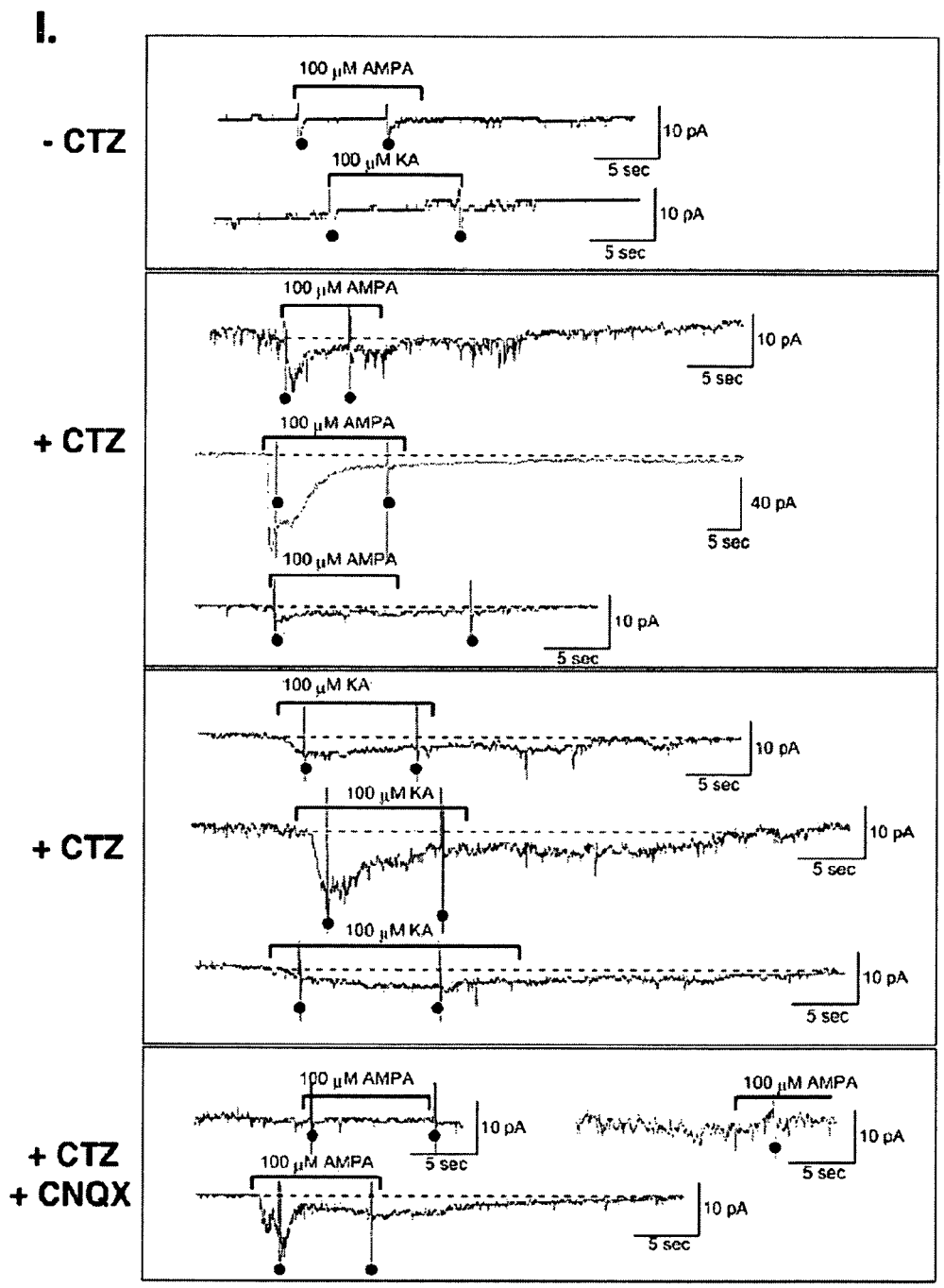

[UBP302] (uM) with TRAP activation

Figure 14
A
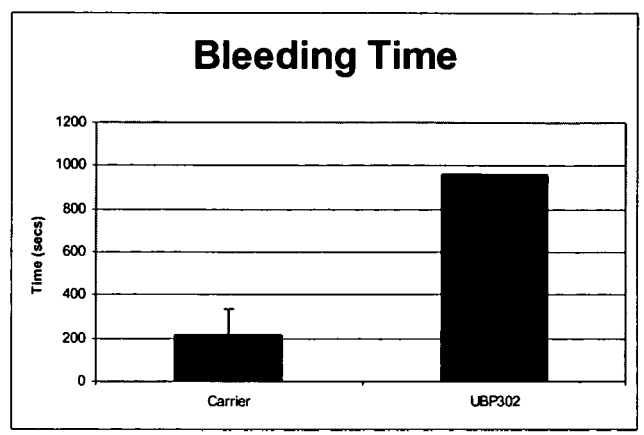
B
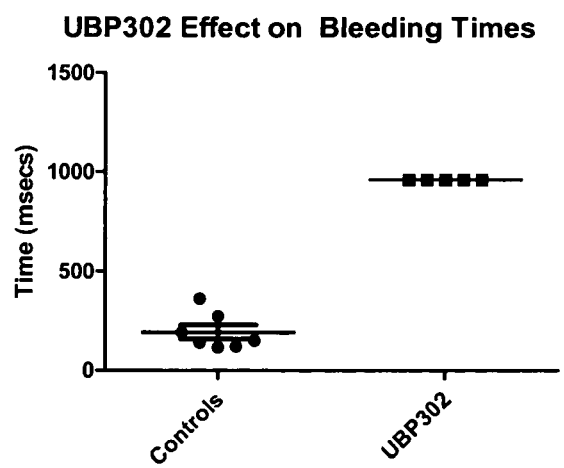

GLUTAMATE RECEPTOR ANTAGONISTS AND METHODS OF USE

RELATED APPLICATIONS

This application claims the benefit of U.S. Provisional application No. 60/880,655, filed on Jan. 16, 2007. The entire contents of the aforementioned application are hereby incorporated herein by reference.

SEQUENCE LISTING

The instant application contains a Sequence Listing which has been submitted electronically in ASCII format and is hereby incorporated by reference in its entirety. Said ASCII copy, created on Oct. 3, 2013, is named 80960(71699)_SL.txt and is 78,543 bytes in size.

FIELD OF THE INVENTION

The present invention relates to methods and compositions for modulating glutamate receptor activity. The invention relates to methods and compositions for modulating platelet activity by inhibiting or activating glutamate receptors. The invention further relates to preventing or treating thrombotic diseases.

BACKGROUND OF THE INVENTION

Glutamate is an excitatory neurotransmitter that binds to the kainate receptor (KAR), the N-methyl-D-aspartate receptor (NMDAR), and the alpha($\alpha$)-amino-3-hydroxy-5-methyl-4-isoxazolepropionic acid receptor (AMPAR). Each receptor was first characterized and cloned in the central nervous system (CNS). Glutamate is also present in the periphery, and glutamate receptors have been identified in non-neuronal tissues, including bone, heart, kidney, pancreas, and platelets.

Platelets play a central role in normal thrombosis and hemostasis, as well as contributing greatly to diseases such as stroke and myocardial infarction. Cardiovascular disease and stroke are major causes of morbidity and mortality. Although many pathophysiologic processes play a role in the chronic development of cardiovascular disease, thrombosis is often the event that precipitates stroke and acute coronary syndromes. Thrombosis is initiated by receptors on resting platelets that respond to activation initiators such as von Willebrand factor (vWf), thrombin, adenosine diphosphate (ADP), and collagen. Blood glutamate concentration is relatively high compared to the concentration in the central nervous system (CNS), and it is tightly controlled by peripheral glutamate transporters. Platelets express glutamate uptake transporters (EAATs) to clear glutamate from the extracellular environment and vesicular glutamate (vGlut) transporters to load glutamate into granules. It has been demonstrated in studies using platelets as peripheral markers of CNS diseases that glutamate is released upon platelet activation. For example, increased plasma glutamate concentrations have been reported in patients upon admission for stroke, perhaps contributing to an increased thrombotic risk, and following stroke, plasma glutamate concentrations rise and remain elevated for up to two weeks. However, functional studies of peripheral glutamate signaling and its role in vascular physiology are limited to date.

Despite the acknowledged principal role of platelet activation in initiating or exacerbating thrombotic or cardiovascular disease, there are currently few platelet specific drugs available. Thus, there is a need in the art for improved anti-thrombotic therapies that would be useful in disease prevention and treatment.

SUMMARY

The present invention is based on the finding that glutamate receptors, in preferred embodiments ionotropic glutamate receptors, modulate platelet activity and thrombosis. These results have important implications for treating and preventing thrombotic diseases where plasma glutamate levels can rise significantly.

In a first aspect, the invention features a method of delaying or preventing platelet activity in a subject comprising administering to the subject an effective amount of a compound that inhibits the activity of one or more glutamate receptors in non-neuronal cells, thereby delaying or preventing platelet activity in a subject.

In one embodiment, platelet activity comprises platelet activation, aggregation, adherence, clotting, or thrombosis.

In another aspect, the invention features a method of treating or preventing a thrombotic disease or disorder in a subject comprising: administering to the subject an effective amount of a compound that inhibits the activity of one or more glutamate receptors in non-neuronal cells in a subject, thereby treating or preventing a thrombotic disease or disorder in a subject.

In another embodiment of the above aspects, the one or more glutamate receptors are selected from ionotrophic glutamate receptors or metabotropic glutamate receptors.

In a further embodiment, the ionotrophic glutamate receptors are selected from the group consisting of: alpha ($\alpha$)-amino-3-hydroxy-5-methyl-4-isoxazolepropionic acid receptors (AMPAR), N methyl-D-aspartate receptors (NMDAR), and Kainate receptors (KAR).

In a related embodiment, the AMPAR comprises at least one subunit selected from the group consisting of: GluR1, GluR2, GluR3 and GluR4. In another related embodiment, the KAR comprises at least one subunit selected from the group consisting of: GluR5, GluR6, GluR7, KA1 and KA2.

In still another embodiment, the non-neuronal cell is selected from the group consisting of platelets, endothelial cells, sub-endothelial cells, leukocytes and megakaryocytes.

In a further embodiment, the thrombotic disease or disorder is selected from the group consisting of: thrombocytopenia and a thrombocytosis.

In a further related embodiment, the thrombotic disease or disorder is selected from the group consisting of: stroke, myocardial infarction (MI), acute coronary syndrome, thrombosis, thrombocytic thrombocytopenic purpura (TTP), vascular occlusion, deep vein thrombosis (DVT), embolism, pulmonary embolism, sepsis, and hereditary hemolytic syndrome (HHS).

In another aspect, the invention features a method of delaying or preventing platelet activity in a subject comprising: administering to the subject an effective amount of a compound that inhibits the activity of AMPA receptors in platelet cells in a subject, thereby delaying or preventing platelet activity.

In still another aspect, the invention features a method of delaying or preventing platelet activity in a subject comprising: administering to the subject an effective amount of a compound that inhibits the activity of KA receptors in platelet cells in a subject, thereby delaying or preventing platelet activity.

In another aspect, the invention features a method of treating or preventing a thrombotic disease or disorder in a subject comprising: administering to the subject an effective amount of a compound that inhibits the activity of AMPA receptors in platelet cells in a subject, thereby treating or preventing a thrombotic disease or disorder in a subject.

In a further aspect, the invention features a method of treating or preventing a thrombotic disease or disorder in a subject comprising: administering to the subject an effective amount of a compound that inhibits the activity of KA receptors in platelet cells in a subject, thereby treating or preventing a thrombotic disease or disorder in a subject.

In one embodiment, any one of the above aspects further comprises inhibiting the activity of a second glutamate receptor.

In another particular embodiment, the second glutamate receptor is selected from the group consisting of: alpha($\alpha$)-amino-3-hydroxy-5-methyl-4-isoxazolepropionic acid (AMPA) receptors (AMPAR), N methyl-D-aspartate (NMDA) receptors (NMDAR), and Kainate (KA) receptors (KAR).

In an embodiment of any one of the above-mentioned aspects, the activity of glutamate receptors is inhibited by a small molecule inhibitor, a nucleic acid inhibitor or an antibody.

In a further embodiment, the small molecule inhibitor is selected from the group consisting of: CNQX, NBQX, GYKI52466, GYKI53655, GYKI47261, cyclothiazide, YM90K, Zonampel (YM872), YM928, Perampanel (E2007), CP-465,022, ZK200775, Talampanel (LY300164), and Tezampanel (NGX424), LY382884, NS-102, UBP301, CX-516, CX-717, topiramate, and philanthotoxin-343, and pharmaceutically acceptable salts, prodrugs, esters, and hydrates thereof.

In another aspect, the invention features a method of increasing platelet activity in a subject comprising: administering to the subject an effective amount of a compound that activates one or more glutamate receptors in non-neuronal cells in a subject, thereby increasing platelet activity in a subject.

In one embodiment, platelet activity comprises platelet activation, aggregation, adherence, clotting, or thrombosis.

In another aspect, the invention features a method of treating or preventing bleeding or a bleeding disease or disorder in a subject comprising: administering to the subject an effective amount of a compound that activates one or more glutamate receptors in non-neuronal cells in a subject, thereby treating or preventing bleeding or a bleeding disease or disorder in a subject.

In a further embodiment, the glutamate receptors are selected from ionotrophic glutamate receptors or metabotropic glutamate receptors.

In a related embodiment, the ionotrophic glutamate receptors are selected from the group consisting of: alpha($\alpha$)-amino-3-hydroxy-5-methyl-4-isoxazolepropionic acid receptors (AMPAR), N methyl-D-aspartate receptors (NMDAR), and Kainate receptors (KAR). In still another related embodiment, the AMPAR comprises at least one subunit selected from the group consisting of: GluR1, GluR2, GluR3 and GluR4. In another further embodiment, the KAR comprises at least one subunit selected from the group consisting of: GluR5, GluR6, GluR7, KA1 and KA2

In another embodiment, the non-neuronal cell is selected from the group consisting of platelets, endothelial cells, subendothelial cells, leukocytes and megakaryocytes.

In a further embodiment, the bleeding is the result of a wound.

In another further embodiment, the bleeding disease or disorder is selected from the group consisting of: von Willebrand Disease, hemophilia, and thrombocytopenia.

In another embodiment, any one of the above-mentioned aspects further comprises the administration of an additional agent.

In a particular embodiment, the additional agent inhibits the activity of a second glutamate receptor.

In another particular embodiment, the additional agent is an imaging agent or a therapeutic agent.

In a further particular embodiment, the therapeutic agent is selected from the group consisting of: anticoagulants, antiplatelet drugs, thrombolytic agents, steroids, hormones, antibiotics, and antiinflammatories.

In another aspect, the invention features a method of diagnosing a subject as having or having a propensity to develop a thrombotic disease or disorder comprising measuring plasma levels of glutamate in a sample from the subject, wherein increased levels of plasma glutamate indicate that the subject has or has a propensity to develop a thrombotic disease or disorder.

In another aspect, the invention features a method of identifying a compound that delays or inhibits platelet activity, the method comprising contacting a cell that expresses a glutamate receptor with a candidate compound, and comparing the biological activity of the glutamate receptor in the cell contacted by the candidate compound with the level of biological activity in a control cell not contacted by the candidate compound, wherein an alteration in the biological activity of the glutamate receptor identifies the candidate compound as a candidate compound that delays or inhibits platelet activity.

In still another aspect, the invention features a method of identifying a compound that delays or inhibits a thrombotic disease or disorder, the method comprising contacting a cell that expresses a glutamate receptor with a candidate compound, and comparing the biological activity of the glutamate receptor in the cell contacted by the candidate compound with the level of biological activity in a control cell not contacted by the candidate compound, wherein an alteration in the biological activity of the glutamate receptor identifies the candidate compound as a candidate compound that delays or inhibits a thrombotic disease.

In one embodiment, the glutamate receptor is selected from an ionotrophic glutamate receptor or a metabotropic glutamate receptor.

In another embodiment, the ionotrophic glutamate receptor is selected from the group consisting of: AMPAR, NMDAR, and KAR. In a related embodiment, the AMPAR comprises at least one subunit selected from the group consisting of: GluR1, GluR2, GluR3 and GluR4. In still another related embodiment, the KAR comprises at least one subunit selected from the group consisting of: GluR5, GluR6, GluR7, KA1 and KA2.

In a further embodiment, the non-neuronal cell is selected from the group consisting of platelets, endothelial cells, subendothelial cells, leukocytes and megakaryocytes.

In another embodiment, the cell is in vitro.

In another embodiment, the cell is in vivo.

In another embodiment, the cell is a human cell.

In a particular embodiment, the alteration in expression is assayed using an immunological assay, an enzymatic assay, a radioimmunoassay, measurement of platelet adhesion, measurement of platelet aggregation, or measurement of platelet activation.

In another aspect, the invention features a pharmaceutical composition comprising a compound that delays or inhibits platelet activity, and a pharmaceutically acceptable excipient.

In a further aspect, the invention features a pharmaceutical composition comprising a compound that delays or inhibits platelet activity, and a pharmaceutically acceptable excipient, wherein the compound is capable of modulating platelet activation, aggregation, thrombosis, adherence or clotting.

In still another aspect, the invention features a pharmaceutical composition comprising a compound that increases platelet activity, and a pharmaceutically acceptable excipient.

In another aspect, the invention features a pharmaceutical composition comprising a compound that increases platelet activity, and a pharmaceutically acceptable excipient, wherein the compound is capable of modulating platelet activation, aggregation, thrombosis, adherence or clotting.

In one embodiment of any one of the above aspects, the pharmaceutical composition further comprises an additional agent.

In a further embodiment, the additional agent inhibits the activity of a second glutamate receptor.

In another further embodiment, the additional agent is an imaging agent or a therapeutic agent.

In another embodiment, the therapeutic agent is selected from the group consisting of:
anticoagulants, antiplatelet drugs, thrombolytic agents, steroids, hormones, antibiotics, and antiinflammatories.

In another aspect, the invention features a method of delaying or preventing platelet activity in a subject comprising (a) identifying a subject that is in need of treatment for delaying or preventing of platelet activity; (b) administering an effective amount of a compound that delays or inhibits platelet activity to the subject, thereby delaying or preventing platelet activity in the subject.

In still another aspect, the invention features a method of treating a thrombotic disease or disorder in a subject comprising: (a) identifying a subject that is in need of treatment for a thrombotic disorder; (b) administering an effective amount of a compound that delays or inhibits platelet activity to the subject, thereby treating the thrombotic disease or disorder in the subject.

In one embodiment, the compound that delays or inhibits platelet activation is selected from the group consisting of: CNQX, NBQX, GYKI52466, GYKI53655, GYKI47261, cyclothiazide, YM90K, Zonampel (YM872), YM928, Perampanel (E2007), CP-465,022, ZK200775, Talampanel (LY300164), and Tezampanel (NGX424), LY382884, NS-102, UBP301, CX-516, CX-717, topiramate, and philanthotoxin-343, and pharmaceutically acceptable salts, prodrugs, esters, and hydrates thereof.

In another embodiment, the thrombotic disease or disorder is selected from the group consisting of: stroke, myocardial infarction (MI), acute coronary syndrome, thrombosis, thrombocytic thrombocytopenic purpura (TTP), vascular occlusion, deep vein thrombosis (DVT), embolism, pulmonary embolism, sepsis, and hereditary hemolytic syndrome (HHS).

In a further embodiment of the above-mentioned aspects, the method further comprises the administration of an additional agent.

In a related embodiment, the additional agent inhibits the activity of a second glutamate receptor.

In another embodiment, the additional agent is an imaging agent or a therapeutic agent.

In another related embodiment, the therapeutic agent is selected from the group consisting of: anticoagulants, antiplatelet drugs, thrombolytic agents, steroids, hormones, antibiotics, and antiinflammatories.

In another aspect, the invention features a kit for the use in delaying or preventing platelet activity in a subject comprising one or more glutamate receptor inhibitors and instructions for use.

In another aspect, the invention features a kit for the use in delaying or preventing a thrombotic disease in a subject comprising one or more glutamate receptor inhibitors and instructions for use.

In still another aspect, the invention features a kit comprising an effective amount of a compound that delays or inhibits platelet activity and associated instructions for using the compound to delay or inhibit platelet activity.

In another aspect, the invention features a kit comprising an effective amount of a compound that delays or inhibits platelet activity and associated instructions for using the compound to treat or prevent a thrombotic disease or disorder.

In another aspect, the invention features a kit comprising an effective amount of a compound that treats or prevents a thrombotic disease or disorder in a subject and associated instructions for using the compound to treat or prevent a thrombotic disease or disorder.

In yet another aspect, the invention features a kit comprising an effective amount of a compound that treats or prevents a thrombotic disease or disorder in a subject wherein the compound inhibits the activity of one or more glutamate receptors in non-neuronal cells in a subject, thereby treating or preventing a thrombotic disease or disorder in the subject.

In an embodiment of any one of the above-mentioned aspects, the subject is a mammal.

In another embodiment of any one of the above-mentioned aspects, the mammal is a human.

Other aspects of the invention are described infra.

BRIEF DESCRIPTION OF THE FIGURES

FIGS. 1(A & B) shows glutamate release in clot formation. (A) Whole blood was diluted in Tyrode's buffer (1:1) and glutamate concentration measured with a voltage sensitive enzymatic probe at rest, following addition of PBS (no change) or thrombin (0.5 U/mL) (representative tracing). (B) is quantification of the results, showing baseline and peak glutamate concentrations during clot formation (n=3-4 *P<0.05).

FIG. 2(A-D) illustrates that glutamate mediates platelet activation. In panel (A), platelets were incubated with glutamate and activated with a moderate concentration of TRAP (5 µM) or high concentration of TRAP (20 µM). Activation was measured by FACS analysis for surface PAC-1 antibody binding (n=4±S.D. *P<0.02 vs 0, 5 µM TRAP). Panel (B) shows a dose response. Platelets were incubated with glutamate and activated with a moderate concentration of TRAP (5 µM). Activation was measured by FACS analysis for surface PAC-1 antibody binding and expressed as per cent increase in fluorescence vs resting platelets (n=5-7±S.D. *P<0.01 vs 0). Panel (C) shows that AMPAR regulates platelet activation. Glutamate increases thromboxane mimetic (U46619, 10 µM) induced platelet activation measured by PAC-1 antibody binding (n=3±S.D. *P<0.01 vs 0 µM). Panel (D) shows that glutamate is highly effective at low dose agonist stimulation. Platelets were incubated with glutamate (150 µM) and activated with TRAP or U46619 (1 µM) (n=5±S.D. *P<0.05 **P<0.01 vs Control).

FIG. 3(A-C) shows platelets express the AMPA receptor. Panel (A) shows glutamate does not act through the NMDA receptor. Platelets were incubated with control, glutamate, or glutamate after the NMDA receptor inhibitor CPP, and then activated or not with TRAP (n=3±S.D. *P<0.05 vs 0 mM).

Panel (B) shows that platelets express AMPAR subunits. Human platelet and mouse brain lysates were immunoblotted for AMPAR subunit proteins GluR1-4. (C) GluR1 is localized to the surface of platelets. Platelets were incubated with control IgG or GluR1 antibody and surface expression assayed by FACS (representative of 3 experiments with similar results).

Figure 4:
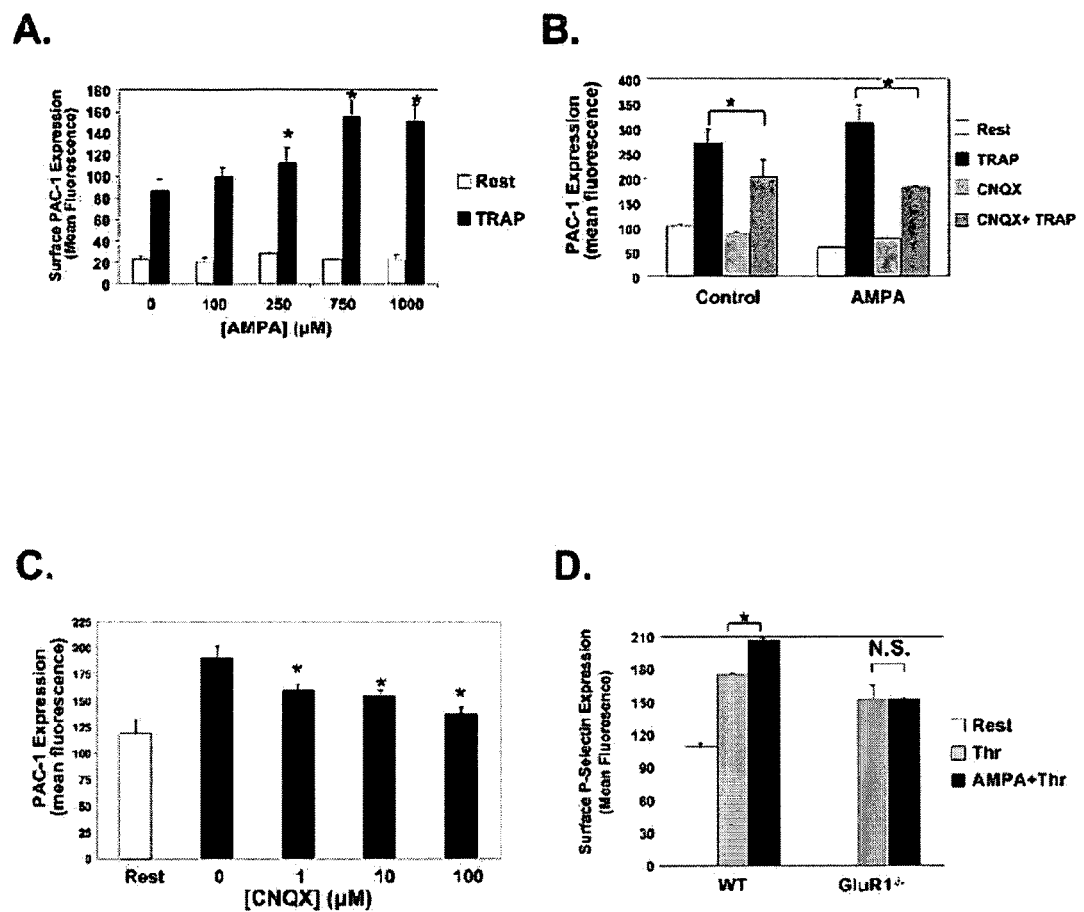

FIG. 4(A-D) illustrates that AMPA receptor signaling mediates platelet activation. (A) AMPA dose dependently increases agonist induced platelet activation. Platelets were incubated with AMPA and then activated with TRAP. Platelet activation was measured by FACS analysis for surface PAC-1 antibody binding (n=5±S.D. *P<0.05 vs 0 mM). Panel (B) shows AMPAR antagonist inhibits AMPA mediated increase in platelet activation. Platelets were incubated with control, CNQX, AMPA, or AMPA after CNQX, and then activated with TRAP (n=3±S.D. *P<0.05). Panel (C) shows AMPAR antagonist decreases platelet activation. Platelets were incubated with control or CNQX, and then activated or not with TRAP (n=5±S.D. *P<0.05). (D) GluR1−/− platelets do not respond to AMPA. Platelets from WT and GluR1−/− mice were incubated with control or AMPA, and activated with 0.25 U/mL thrombin (Thr) (n=3±S.D. *P<0.05; N.S.=not significant).

FIG. 5(A-F) shows that platelet AMPA receptor mediates sodium transport. Panel (A) illustrates AMPA increases intracellular sodium. Platelets were loaded with SBFI; treated with control, AMPA, CNQX, or AMPA after CNQX; and activated with TRAP. Change in intracellular sodium was measured by FACS (n=3±S.D. *P<0.05 vs control). Panel (B) shows that AMPAR increases Na+ influx independent of NHE. Platelets were treated with control, amiloride, AMPA or amiloride prior to AMPA. Intracellular Na+ was determined by FACS. (n=3±S.D. *P<0.05). In panel (C) fast application of AMPA to megakaryocytes induces a rapid inward current that reverses close to 0 mV. The top panel depicts a current trace showing an inward current induced by fast application of AMPA (time of application shown by the solid line). Rapid current steps for determining I-V relationships were applied before (not shown) and during application of AMPA (rapid current deflection, black dots). The bottom panel shows the I-V relationship obtained for the AMPA-induced current. The plot represents the averaged I-V curves obtained from 5 different cells, normalized to the current obtained at −60 mV. In panel (D) fast application of KA to megakaryocytes induced a rapid inward current that reversed close to 0 mV. The top panel shows a current trace while the averaged I-V curves for KA application is shown in the bottom panel. Panel (E) shows that the inward current induced by AMPA was blocked by administration of the AMPAR antagonist CNQX, (30 µM; *P<0.01) Panel (F) shows that joro spider toxin (JST) had no effect on the AMPAR triggered increase in platelet activation. Platelets were incubated with 1 µM JST and then activated or not with TRAP (n=3+/−S.D.).

FIG. 6(A-D) illustrates glutamate mediates an increase in GPCR signaling. Panel (A) shows that glutamate increases epinephrine mediated platelet activation. Epinephrine (10 µM) induced platelet activation was measured by PAC-1 antibody binding (n=5±S.D. *P<0.01 vs 0 µM). Panel (B) shows that glutamate does not effect collagen mediated platelet activation. Platelets were incubated with glutamate and activated with collagen. Activation was measured by FACS analysis for surface PAC-1 antibody binding (n=5±S.D., N.S.=not significant). Panel (C) shows that glutamate does not increase ATP induced platelet activation. ATP induced platelet activation was measured by PAC-1 antibody binding (n=5±S.D., N.S.=not significant). Panel (D) shows that glutamate increases P2Y mediated platelet activation. P2Y agonist, 2-Me-ADP, induced platelet activation was measured by PAC-1 antibody binding (n=5±S.D. *P<0.01 vs 0 µM).

FIG. 7(A-C) illustrates that AMPA receptor signaling mediates platelet aggregation. In Panel (A) AMPAR inhibition decreases platelet aggregation. Platelets were incubated with control or CNQX and activated with TRAP (10 µM). Platelet aggregation was measured by an aggregometer. Panel (B) shows quantification. AMPAR inhibition decreases platelet aggregation (n=5-12±S.D. *P<0.01). In Panel (C) exogenous AMPA increases early platelet aggregation (n=5±S.D. *P=0.03, N.S.=Not Significant, p=0.09).

Figure 8:
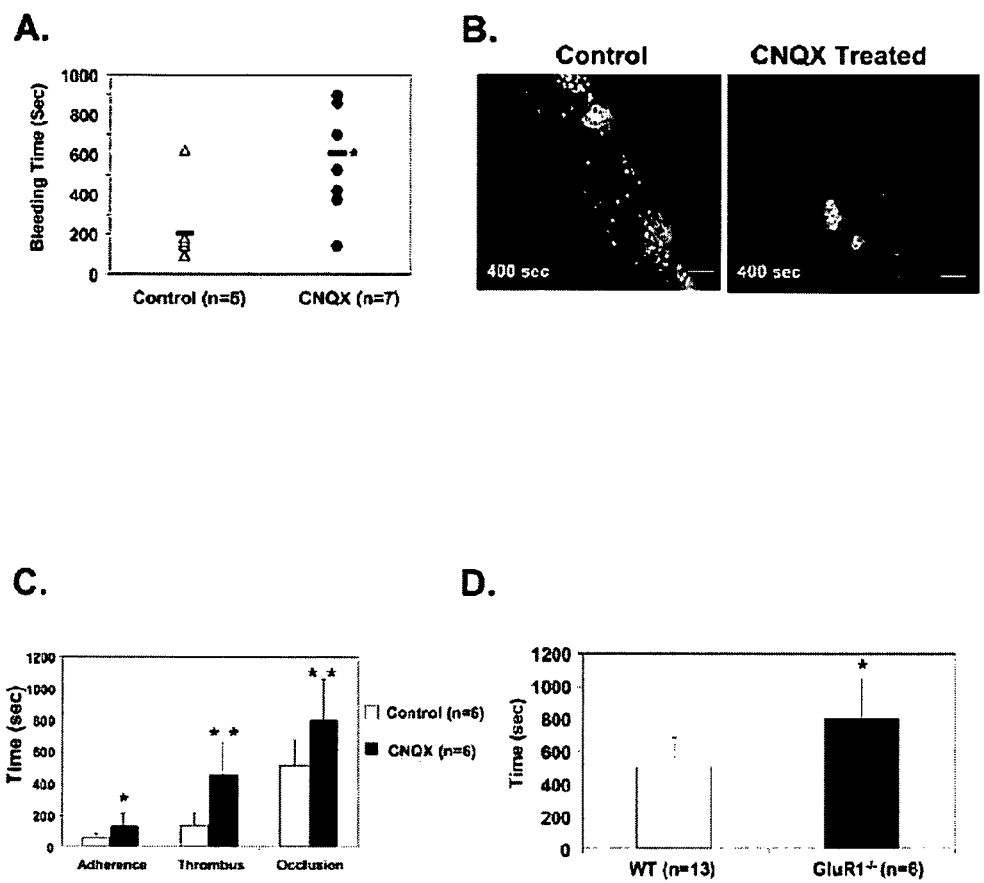

FIG. 8(A-D) illustrates AMPA receptor mediates platelet function in vivo. In panel (A) AMPAR inhibition with CNQX (0.1 mg/kg) prolongs bleeding time in vivo. (*P<0.01 vs control). In Panel (B) FeCl3 was placed on externalized mesenteric arterioles and platelets were imaged using intravital microscopy (representative images 400 sec after FeCl3, bar=25 µM). Panel (C) shows AMPAR inhibition with CNQX (0.1 mg/kg) prolongs platelet adherence, thrombus formation, and vessel occlusion in vivo. (±S.D. *P<0.05, **P<0.01 vs control). Panel (D) shows that GluR1−/− mice have prolonged time to vessel occlusion in vivo (±S.D. *P<0.02 vs WT).

FIG. 9(A-I) is nine panels. Panel (A) shows calibration of glutamate probe. Panel (B) illustrates that glutamate increases agonist induced platelet activation: P-selectin. Platelets were incubated with control or glutamate and activated or not with TRAP. P-selectin expression measured by FACS (n=3±S.D. *P<0.05 vs 0 mM). Panel (C) shows that AMPA increases agonist induced platelet activation at moderate agonist concentrations. Platelets were incubated with AMPA (250 µM) and then activated or not with thromboxane mimetic. Platelet activation was measured by FACS analysis for surface increase in PAC-1 antibody binding vs resting platelets (n=5±S.D. *P<0.01 vs Control). Panel (D) illustrates AMPAR antagonist decreases platelet activation. P-selectin. Platelets were incubated with control, or CNQX, and then activated or not with TRAP. Platelet activation was measured by FACS for P-selectin expression (n=5±S.D. *P<0.05 vs 0). In Panel (E) AMPAR antagonist decreases platelet activation. Platelets were incubated with control or NBQX and activated or not with TRAP. Platelet activation was measured by FACS for PAC-1 antibody binding (n=3±S.D. *P<0.05). Panel (F) shows that amiloride inhibits NHE. Platelets were preincubated with the pH sensitive dye BCEF and the change in intracellular pH with TRAP activation was measured by FACS. Panel (G) shows that platelet AMPA Receptor Mediates Ion Transport. AMPAR activity is independent of NHE. Platelets were incubated with control, AMPA, amiloride (Amil), or amiloride prior to AMPA and activated or not with TRAP (n=3±S.D. *P<0.05). In Panel (H) representative current traces for electrophysiology experiments are shown. Left most panel; AMPA (100 µM) evoked currents correspond to FIG. 5 C. Middle panel; KA (100 µM) evoked currents correspond to FIG. 5 D. Right most panel; CNQX (30 µM) blocks AMPA induced current corresponding to FIG. 5 E. Panel (I) illustrates representative current traces. Traces represent time pre and post agonist/antagonist application with and without cyclothiazide (CTZ).

Figure 10:
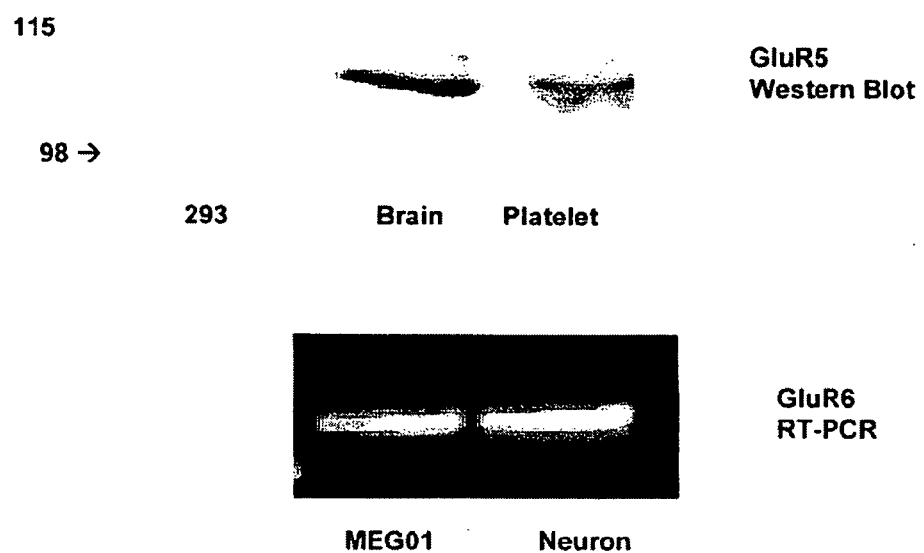

FIG. 10 shows the kainate (KA) receptor is present in platelet cells. The top panel shows the results of a Western blot and the bottom panel shows the results of RT-polymerase chain reaction (PCR) experiments.

Figure 11:
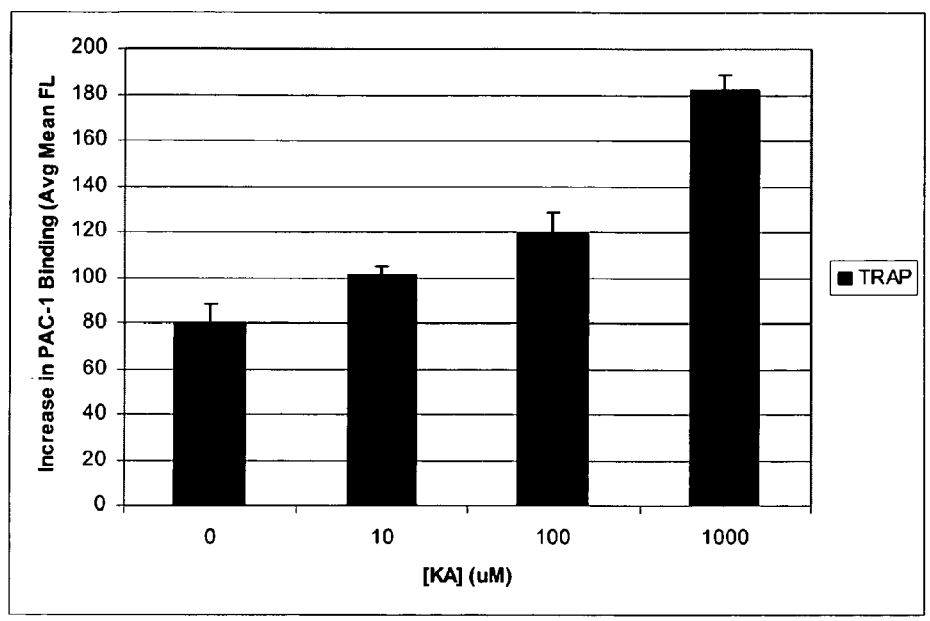

FIG. 11 is a graph that illustrates that KA dose dependently increases TRAP-induced platelet activation by FACS.

Figure 12:
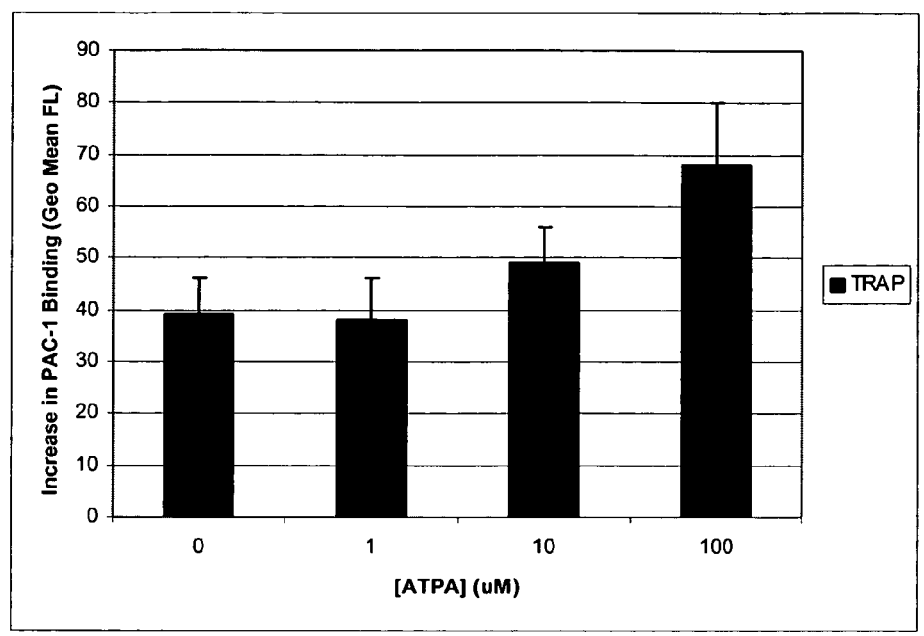

FIG. 12 is a graph that shows the KAR specific agonist ATPA increases platelet activation by FACS.

Figure 13:
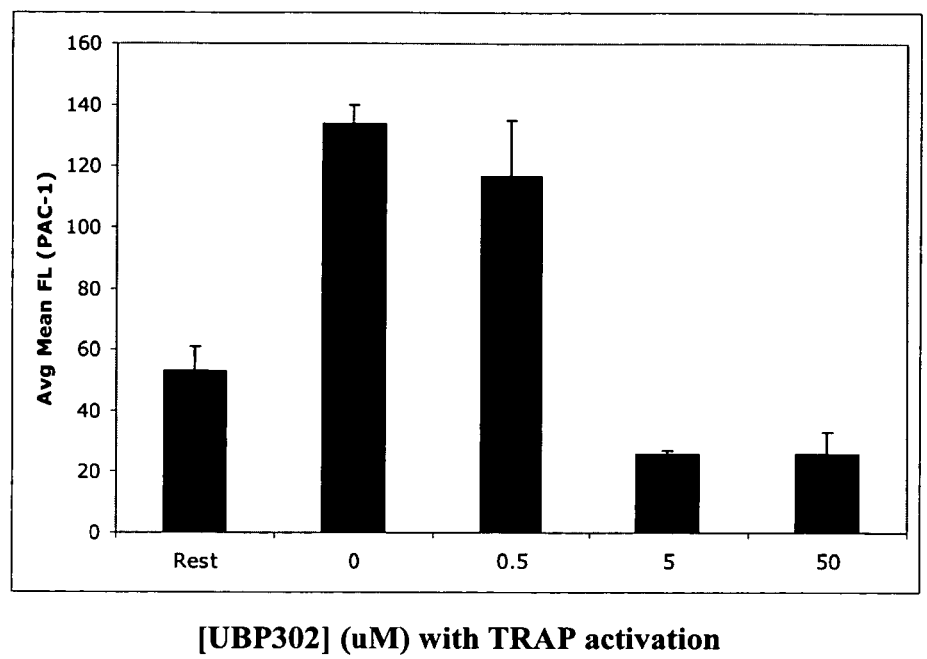

FIG. 13 is a graph that shows the KA receptor specific inhibitor UBP302 dose dependently reduces platelet activation.

FIGS. 14(A & B) is two graphs that illustrate KA receptor specific antagonist UBP302 prolongs bleeding time in mice.

Figure 15:
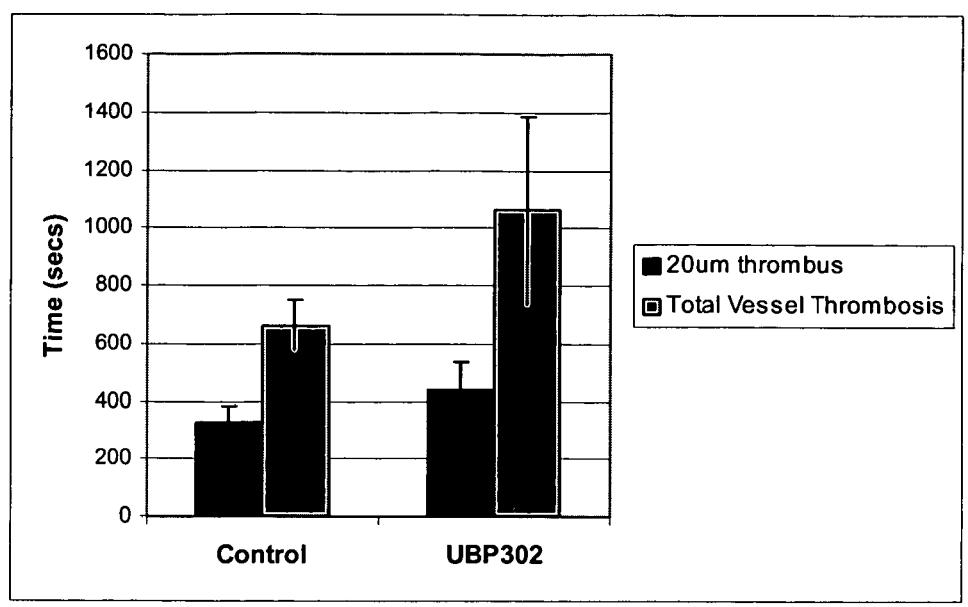

FIG. 15 is a graph that shows mice treated with KA receptor antagonists have prolonged time to total vessel occlusion. The inset legend shows that 20 um thrombus and total vessel thrombosis were measured.

DETAILED DESCRIPTION OF THE INVENTION

The present invention is based on the novel finding that activated platelets release glutamate, that platelets express glutamate receptors, and that glutamate increases agonist induced platelet activation. The identification of glutamate as a regulator of platelet activation suggests glutamate receptors as novel therapeutic targets.

The present invention provides methods and compositions for modulating platelet activity by inhibiting or activating glutamate receptors. The invention further relates to preventing or treating thrombotic diseases.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used in the specification and claims, the singular form "a," "an" and "the" include plural references unless the context clearly dictates otherwise. For example, the term "a cell" includes a plurality of cells, including mixtures thereof The term "a nucleic acid molecule" includes a plurality of nucleic acid molecules.

As used herein, the term "comprising" is intended to mean that the compositions and methods include the recited elements, but do not exclude others. "Consisting essentially of," when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The terms "administration" or "administering" as used herein is meant to refer to an act of providing a compound or pharmaceutical composition of the invention to a subject in need of treatment.

The term "agent" as used herein is meant to refer to any biologically active molecule. An agent can be a polypeptide, polynucleotide, or fragment, or analog thereof, a small molecule, a synthetic molecule, or a chemical compound.

The terms "bleeding disease or disorder" are meant to refer to a disease or disorder that is characterized by abnormal bleeding, e.g. excessive bleeding. In certain cases, abnormal bleeding can be caused by the failure of clots to form. Exemplary bleeding diseases include, but are not limited to, hemophilia, von Willebrand Disease, and thrombocytopenia. In other certain embodiments, excessive bleeding may be the result of another condition, e.g. secondary to another disease or disorder.

The term "control" as used herein is meant to refer to a standard or reference condition.

The term "glutamate receptor(s)" is meant to refer to membrane receptors that bind glutamate. Glutamate receptors can be classified as ionotropic or metabotropic. "Ionotrophic" glutamate receptors are meant to refer to ligand gated ion channels that bind glutamate. "Metabotropic" receptors are meant to refer to signal transduction protein coupled transmembrane receptors that bind glutamate. Exemplary glutamate receptors include, but are not limited to, kainate (KA) receptors, N methyl-D-aspartate (NMDA) receptors, and alpha ($\alpha$)-amino-3-hydroxy-5-methyl-4-isoxazolepropionic acid (AMPA) receptors (AMPAR).

The GenBank Accession No. for the amino acid sequence of an exemplary AMPAR subunit 1 is NP_000818 and corresponds to SEQ ID NO: 1.

The GenBank Accession No. for the amino acid sequence of an exemplary AMPAR subunit 2 (isoform 1) is NP_000817 and corresponds to SEQ ID NO: 2.

The GenBank Accession No. for the amino acid sequence of an exemplary KARGluR6 subunit is CAC67487 and corresponds to SEQ ID NO: 3.

The GenBank Accession No. for the amino acid sequence of an exemplary KAR 1 subunit is NP_055434 and corresponds to SEQ ID NO: 4.

The GenBank Accession No. for the amino acid sequence of an exemplary KAR 2a subunit is NP_002079 and corresponds to SEQ ID NO: 5.

The GenBank Accession No. for the amino acid sequence of an exemplary GluR3 subunit is NP_000831 and corresponds to SEQ ID NO: 6.

The GenBank Accession No. for the amino acid sequence of an exemplary GluR4 subunit is NP_000820 and corresponds to SEQ ID NO: 7.

The GenBank Accession No. for the amino acid sequence of an exemplary GluR5 subunit is NP_000821 and corresponds to SEQ ID NO: 8

The GenBank Accession No. for the amino acid sequence of an exemplary GluR6 subunit is NP_068775 and corresponds to SEQ ID NO: 9.

The GenBank Accession No. for the amino acid sequence of an exemplary GluR7 subunit is NP_000822 and corresponds to SEQ ID NO: 10.

The term "imaging agent" is meant to refer to any agent that can be detected by an imaging device. In certain preferred embodiments, an imaging agent is a radiolabel. In certain exemplary embodiments an imaging agent is used to visualize sites of platelet deposition or thrombus formation.

The term "inhibit" or "decrease" as used herein is meant to refer to a reduction by at least about 5% relative to a reference level. A decrease may be by 5%, 10%, 15%, 20%, 25% or 50%, or even by as much as 75%, 85%, 95% or more. An inhibition may be 2-fold, 5-fold, 10-fold, 20-fold, 40-fold, or even 100-fold.

The term "increase" or "activate" as used herein is meant to refer to a stimulation by at least about 5% relative to a reference level. An increase may be by 5%, 10%, 15%, 20%, 25% or 50%, or even by as much as 75%, 85%, 95% or more. An increase may be 2-fold, 5-fold, 10-fold, 20-fold, 40-fold, or even 100-fold.

The term "megakaryocyte" is meant to refer to a bone marrow cell that produces platelets.

The term "non-neuronal cell" as used herein is meant to refer to any cell that is not derived from nervous tissue. In exemplary embodiments, a non-neuronal cell is a platelet.

The term "pharmaceutically-acceptable excipient" as used herein means one or more compatible solid or liquid filler, diluents or encapsulating substances that are suitable for administration into a human.

The term "platelets" as used herein is meant to refer to cells that circulate in the blood take part in the clotting process. Platelets contain granules that contain compounds that enhance the ability of platelets to stick to each other and to the surface of a damaged blood vessel wall. "Thrombocytopenia" refers to a platelet count that is below a normal level. "Thrombocytosis" refers to a platelet count that is above a normal level. In certain embodiments, a normal level of platelets is between 150,000 to 400,000/mm3.

The phrase "platelet activity" is meant to refer to one or more functions of platelets. In certain embodiments platelet activity includes, but is not limited to, platelet activation, aggregation, adherence, clotting, or thrombosis.

The terms "prevent," "preventing," "prevention" and the like as used herein are meant to refer to reducing the probability of developing a disorder or condition in a subject, who does not have, but is at risk of or susceptible to developing a disorder or condition.

The term "small molecule" inhibitor as used herein is meant to refer to a molecule of less than about 3,000 daltons having glutamate receptor inhibitory activity. In certain embodiments, small molecule inhibitors can have inhibitory activity against one or more glutamate receptor type, e.g. a small molecule inhibitor that is an AMPA receptor inhibitor, a KA receptor inhibitor, or that is both a AMPA receptor inhibitor and a KA receptor inhibitor.

The term "subject" as used herein is a vertebrate, preferably a mammal, more preferably a human. Mammals include, but are not limited to, murines, simians, humans, farm animals, sport animals, and pets. Subjects may include animal disease models (e.g., mice).

The term "thrombosis" is meant to refer to the formation of a thrombus, or clot.

The term "thrombotic disease or disorder" is meant to refer to any disease caused by the occlusion of blood vessels. A thrombotic disease or disorder includes, but is not limited to, stroke, myocardial infarction (MI), acute coronary syndrome, thrombosis, thrombocytic thrombocytopenic purpura (TTP), vascular occlusion, deep vein thrombosis (DVT), embolism, pulmonary embolism, sepsis, and hereditary hemolytic syndrome (HHS).

The term "treating" a thrombotic disease or disorder is meant to slow the progression of the disease, to slow the growth of progression of the thrombus formation, to relieve symptoms caused by the thrombus, or to prevent growth or formation of the thrombus.

I. Glutamate Receptors

Glutamate is an important excitatory neurotransmitter in the mammalian central nervous system. Glutamate is involved in many physiological functions, including learning and memory, but also in toxic phenomena occurring in numerous degenerative or neurological diseases. These functions mainly result from its interaction with Glu receptors (GluRs). The broad spectrum of roles played by glutamate is derived from the large number of membrane receptors, which are currently classified in two main categories: ionotropic (iGluRs) and metabotropic (mGluRs) receptors. The iGluRs are ion channels, permeant to Na(+) (Ca(2+)) and K(+) while the mGluRs belongs to the superfamily of G-protein coupled receptors (GPCRs). The iGluRs are ligand gated ion channels that were originally named for exogenous agonists that are selective for each subtype and include α-amino-3-hydroxy-5-methyl-4-isoxazole propionic acid (AMPA), kainate, and N-methyl-D-aspartate (NMDA). Each of these receptors are multimeric assemblies of one or more subunits, and there are considerable numbers of variants of the subunits related by either alternate splicing of the RNA transcripts or editing of the RNA that results in changes in a single base and a corresponding change in a single amino acid. (Sheldon et al. Neurochem Int. 2007; 51(6-7): 333-355).

In general, the term "glutamate receptor(s)" is meant to refer to membrane receptors that bind glutamate.

Exemplary ionotropic glutamate receptors include, but are not limited to, kainate (KA) receptors, N-methyl-D-aspartate (NMDA) receptors, and alpha(α)-amino-3-hydroxy-5-methyl-4-isoxazolepropionic acid (AMPA) receptors (AMPAR).

The NMDA, KA, and AMPA receptors have been well described as responding to glutamate released from a presynaptic neuron during excitatory neurotransmission, but glutamate mediated signaling may also be important in cells not commonly considered excitatory (16). For example, AMPA receptor activity can stimulate insulin release from beta-cells in the pancreas, and NMDA receptors have been noted in osteoblasts, osteoclasts, and platelets (17-19). NMDA receptor signaling is reported to have a role in regulating platelet production from megakaryocytes, in addition to potentially inhibiting platelet activation (20-23).

Glutamate receptors have been identified at sites outside of the central nervous system (CNS), including, but not limited to the heart, spleen, testis, and kidney (16, 24). Several of these peripheral glutamate receptors have been cloned and sequenced and are identical to those in the CNS (16). Blood glutamate concentration is relatively high compared to the CNS and is tightly controlled by peripheral glutamate transporters (16). Platelets express glutamate uptake transporters (EAATs) to clear glutamate from the extracellular environment and vesicular glutamate (vGlut) transporters to load glutamate into granules (12, 13, 15). Studies primarily aimed at using platelets as peripheral markers of CNS diseases have demonstrated that glutamate is released upon platelet activation (12, 14, 25, 26). Following stroke plasma glutamate concentrations rise and remain elevated for up to two weeks (14, 27). Concentrations greater than 200 μM have been reported in patients upon admission for stroke, perhaps contributing to an increased thrombotic risk (25, 27).

Although described in many tissues, AMPAR is best characterized in the brain as a glutamate sensitive ion channel of neuronal activation (16, 20). AMPA receptors are comprised of heteromeric tetramer complexes of subunits designated GluR1-GluR4 (28, 29). The AMPAR subunits combine to form a transmembrane receptor with a central ion permeable channel. Glutamate binding to AMPAR triggers Na+ influx and facilitates transduction of an electrical current (30). Calcium permeability of the AMPAR is dictated by the GluR2 subunit isoform present. GluR2 isoform expression varies between regions of the brain, and with it, AMPAR permeability to calcium also varies (31, 32).

Five different Na+-dependent high-affinity glutamate transporters have been identified; these transporters share approximately 50-60% amino acid sequence similarity. Based on the elucidation of the crystal structure of a bacterial glutamate transporter homologue (Yernool, et al., Nature. 2004; 431:811-818), the transporters are predicted to have 8 transmembrane domains with intracellular carboxyl and amino termini and most likely exist as trimers. Two of these transporters are called GLAST (Storck, et al., Proceedings of the National Academy of Sciences USA. 1992; 89:10955-10959) and GLT-1 (Pines, et al., Nature. 1992; 360:464-467); these are also called EAAT1 or EAAT2, respectively (Arriza, et al., J Neurosci. 1994; 14:5559-5569). There are several variants of GLT-1 that originate from alternate splicing of mRNA and these variants differ in their carboxyl- and amino-terminal sequences (Reye, et al., J Comp Neurol. 2002a; 447:323-30; Reye, et al., Glia. 2002b; 38:246-55; Rauen, et al., Neurochem Int. 2004; 45:1095-106; Sullivan, et al., Glia. 2004; 45:155-69).

Platelets

The role of platelets in mammalian physiology is diverse, but their primary role is in promoting hemostasis. Platelets are cells that circulate in the blood and take part in the clotting process. Platelets play a critical role in the maintenance of normal hemostasis. When exposed to a damaged blood vessel, platelets will adhere to exposed sub-endothelial matrix. Following the initial adhesion, various factors released or produced at the site of injury such as thrombin, ADP and collagen activate the platelets. Once platelets are activated, a conformational change occurs in the platelet glycoprotein GPIIb/IIIa receptor, allowing it to bind fibrinogen and/or von Willebrand factor. It is this binding of the multivalent fibrinogen and/or von Willebrand factor molecules by GPIIb/IIIa receptors on adjacent platelets that results in the recruitment of additional platelets to the site of injury and their aggregation to form a hemostatic plug or thrombus.

Platelets contain granules that contain compounds that enhance the ability of platelets to stick to each other and to the surface of a damaged blood vessel wall. Platelets secrete and express a large number of substances that are mediators of both coagulation and inflammation.

The phrase "platelet activity" is meant to refer to one or more functions of platelets. In certain embodiments platelet activity includes, but is not limited to platelet activation, aggregation, adherence, clotting, or thrombosis.

Platelets are known to aggregate under a variety of conditions and in the presence of a number of different reagents. Platelet aggregation is a term used to describe the binding of platelets to one another. Platelet aggregation in vitro depends upon the ability of platelets to bind fibrinogen to their surfaces after activation by an aggregation-inducing agent such as ADP or collagen.

Despite the acknowledged principal role of platelet activation in initiating or exacerbating cardiovascular disease, there are currently few platelet specific drugs available, making investigation into mechanisms of platelet activation very important.

Following the initiation of platelet activation subsequent pathways are activated, including conformational changes in receptors (e.g. GPIIb/IIIa), granule exocytosis, and the secretion of vasoactive mediators. Activation of resting platelets triggers a variety of intraplatelet signaling pathways, including changes in intracellular ion concentrations such as a burst of intracellular Na+ (1-3). The primary identified means of increasing intracellular Na+ is via the Na+/H+ exchanger, which is relatively slow and does not account for the large rapid increase in Na+ influx (4, 5). It has also been demonstrated that membrane depolarization in megakaryocytes and other cells mediates an increase in ligand affinity and downstream signaling of G coupled protein receptors (GPCR), such as the platelet purinic receptors (P2Y) (6-8). Therefore, efficient generation of inward currents by ion flux may be an important modulator of platelet response to agonists such as ADP, thrombin, and thromboxane.

Many molecules and receptors involved in platelet function also have important roles in neuronal function including: exocytosis regulatory molecules, serotonin/serotonin receptor, ADP/Purinergic Receptors, PAR receptors, ApoE/ApoER, alpha-synuclein, acetylcholine, epinephrine, and substance P (9-11). Platelet dense granules also contain and release glutamate, an important neurotransmitter (12-15).

Tests that can be used to determine and assess platelet function include platelet aggregometry, the platelet function analyzer and thromboelastography.

In vitro platelet aggregometry is the laboratory method used to assess the in vivo ability of platelets to form the aggregates leading to a primary hemostatic plug. In this technique an aggregating agent such as ADP or collagen is added to whole blood or platelet-rich plasma and aggregation of platelets monitored. Platelet aggregometry is a diagnostic tool that can aide in patient diagnosis and selection of therapy.

A rapid platelet function assay has recently been developed and is described in U.S. Pat. No. 5,763,199, incorporated by reference in its entirety herein. The assay determines glycoprotein (GP) IIb/IIIa receptor blockade in whole blood. Agglutination of small polymeric beads coated with a GPIIb/IIIa ligand such as fibrinogen results when the beads are contacted with whole blood containing platelets with activated GPIIb/IIIa receptors that are not blocked. Failure to agglutinate indicates either failure of the GPIIb/IIIa receptors to become activated and/or blockade of the GPIIb/IIIa receptors. In a preferred embodiment, the addition of a thrombin receptor activator results in an assay that is rapid and convenient enough to be performed at the bedside and that results in agglutination of the small polymeric beads within a convenient, known period of time if the GPIIb/IIIa receptors are not blocked. The assay includes the ability to transfer blood to be tested from a collection container to an assay device without opening the collection container. This platelet aggregation assay can be conducted at the same time as the activated clotting time (ACT), which is performed to assess the adequacy of heparinization.

II. Methods

The invention features in certain aspects methods of delaying or preventing platelet activity in a subject comprising administering to the subject an effective amount of a compound that inhibits the activity of one or more glutamate receptors in non-neuronal cells, and thereby delays or prevents platelet activity in a subject.

The term "platelets" as used herein is meant to refer to cells that circulate in the blood that take part in the clotting process. Platelets contain granules that contain compounds that enhance the ability of platelets to stick to each other and to the surface of a damaged blood vessel wall.

The phrase "platelet activity" is meant to refer to one or more functions of platelets. In certain embodiments platelet activity includes, but is not limited to platelet activation, aggregation, adherence, clotting, or thrombosis.

The invention features methods of treating or preventing a thrombotic disease or disorder in a subject comprising administering to the subject an effective amount of a compound that inhibits the activity of one or more glutamate receptors in non-neuronal cells in a subject, thereby treating or preventing a thrombotic disease or disorder in a subject.

Glutamate (Glu) receptors are classified into two major categories in the mammalian central nervous system: ionotropic receptors linked to ion channels and metabotropic receptors linked to phosphatidylinositol (PI) metabolism. Classification of the ionotropic Glu receptors is based on the differential sensitivity to excitement by N-methyl-D-aspartic acid (NMDA), DL-alpha-amino-3-hydroxy-5-methylisoxazole-4-propionic acid (AMPA) and kainic acid (KA). The NMDA-sensitive subclass is composed of a receptor ionophore complex consisting of at least four different subcomponents, including an NMDA recognition site, a glycine (Gly) recognition site, a polyamine recognition site and a cation channel. The NMDA site is radiolabeled by both Glu and competitive antagonists, such as (+−)-3-(2-carboxypiperazin-4-yl)propyl-1-phosphonic acid (CPP) and DL-(E)-2-amino-4-propyl-5-phosphono-3-pentenoic acid (CGP 39653). The Gly domain, which is labeled by both [3H] Gly and [3H] 5,7-dichlorokynurenic acid, is sensitive to D-serine but insensitive to strychnine, and this domain seems to be absolutely required for an activation of the NMDA channel by agonists. The ionophore domain is identified by radiolabeled non-competitive NMDA antagonists that gain access to the binding sites within the channel only when it is gated by agonists. The opening of an NMDA channel is allosterically potentiated by Gly and several polyamines. In contrast, an activation of the NMDA channel is blocked by both H+ and divalent cations such as $Mg2+$ and $Zn2+$. [3H]AMPA binding displays pharmacological profiles of the AMPA-sensitive subclass with a rank order of agonistic potencies of quisqualic acid (QA) greater than or equal to AMPA greater than Glu greater than KA, which is apparently different from that found for the KA-sensitive subclass (domoic acid greater than or equal to KA greater than QA greater than Glu). In contrast, several quinoxaline derivatives competitively antagonize neuronal responses mediated not only by the AMPA receptor but also by the KA receptor.

The metabotropic Glu receptors, which stimulate PI metabolism through an activation of the guanosine triphosphate-binding proteins, are activated by Glu, QA and trans-1-amino-cyclopentyl-1,3-di-carboxylic acid (ACPD). Responses mediated by the metabotropic receptors are competitively blocked by 2-amino-3-phosphonopropionic acid. Three or four cloned complementary deoxyribonucleic acids (cDNAs) encoding inotropic Glu receptors are isolated from a rat brain cDNA library. Pharmacological and electrophysiological properties of receptor-ion channels encoded by a transfection of these cDNAs are similar to those observed with the AMPA receptor as well as the KA receptor, but not with the NMDA receptor.

In certain embodiments of the invention, the one or more glutamate receptors may be ionotrophic glutamate receptors or metabotropic glutamate receptors.

In other certain embodiments, the ionotrophic glutamate receptors are selected from the group consisting of: alpha ($\alpha$)-amino-3-hydroxy-5-methyl-4-isoxazolepropionic acid receptors (AMPAR), N methyl-D-aspartate receptors (NMDAR), and Kainate receptors (KAR). As described previously herein the AMPA Receptor can comprise at least one subunit selected from the group consisting of GluR1, GluR2, GluR3 and GluR4. The KA Receptor can comprise at least one subunit selected from the group consisting of: GluR5, GluR6, GluR7, KA1 and KA2.

The invention features in certain other aspects methods of delaying or preventing platelet activity in a subject comprising administering to the subject an effective amount of a compound that inhibits the activity of AMPA receptors in platelet cells in a subject, thereby delaying or preventing platelet activity.

The invention features in other aspects methods of delaying or preventing platelet activity in a subject comprising administering to the subject an effective amount of a compound that inhibits the activity of KA receptors in platelet cells in a subject, thereby delaying or preventing platelet activity.

The invention features in other aspects methods of treating or preventing a thrombotic disease or disorder in a subject comprising administering to the subject an effective amount of a compound that inhibits the activity of AMPA receptors in platelet cells in a subject, thereby treating or preventing a thrombotic disease or disorder in a subject.

The invention features in other aspects methods of treating or preventing a thrombotic disease or disorder in a subject comprising administering to the subject an effective amount of a compound that inhibits the activity of KA receptors in platelet cells in a subject, thereby treating or preventing a thrombotic disease or disorder in a subject.

In any of the methods as described herein, the methods may comprise inhibiting the activity of a second glutamate receptor. The second glutamate receptor can be of a different class as the first glutamate receptor that is inhibited. For example, the first glutamate receptor that is inhibited may be an ionotrophic glutamate receptor, and the second glutamate receptor that is inhibited is a metabotropic glutamate receptor. Alternatively, the second glutamate receptor can be of the same class as the first glutamate receptor that is inhibited. For example, the first glutamate receptor that is inhibited may be an ionotrophic glutamate receptor, and the second glutamate receptor that is inhibited is also an ionotrophic glutamate receptor. In the latter case, the first ionotrophic glutamate receptor may be AMPAR and the second ionotrophic glutamate receptor may be KAR, e.g. the ionotrophic glutamate receptors are of different types. Alternatively, the second glutamate receptor may be a different subunit, for example the first glutamate receptor that is inhibited may be the GluR1 subunit of AMPAR and the second glutamate receptor that is inhibited may be the GluR2 subunit of AMPAR.

In certain preferred embodiments, the second glutamate receptor is selected from the group consisting of alpha($\alpha$)-amino-3-hydroxy-5-methyl-4-isoxazolepropionic acid (AMPA) receptors (AMPAR), N methyl-D-aspartate (NMDA) receptors (NMDAR), and Kainate (KA) receptors (KAR).

The invention also features methods of increasing platelet activity in a subject comprising administering to the subject an effective amount of a compound that activates one or more glutamate receptors in non-neuronal cells in a subject, thereby increasing platelet activity in a subject.

In certain cases, increasing platelet activity can be beneficial, for example, when increased clotting (thrombus formation) is desired. Such a situation, for example, may be in a wound dressing in a situation where rapid stopping of bleeding is desired. Accordingly, the bleeding can be the result of a wound.

The invention also features methods of treating or preventing bleeding, or a bleeding disease or disorder in a subject comprising administering to the subject an effective amount of a compound that activates one or more glutamate receptors in non-neuronal cells in a subject, thereby treating or preventing bleeding or a bleeding disease or disorder in a subject.

The bleeding disease or disorder may be the result of another disease or condition (e.g. liver disease). The bleeding disease may be hereditary (von Willebrand Disease), or the bleeding disease may be the result of a medication or therapeutic regimen.

The bleeding disease or disorder can be von Willebrand Disease (vWD). Von Willebrand Disease is a bleeding disorder caused by a defect or deficiency of a blood clotting protein, called von Willebrand Factor. The disease is estimated to occur in 1% to 2% of the population. VWD occurs about as often in men as it does in women. Von Willebrand Factor is a protein critical to the initial stages of blood clotting. VWF is produced by the cells that line the blood vessel walls, and interacts with platelets to form a clot (thrombus), which prevents the blood from flowing at the site of injury. People with von Willebrand Disease are unable to make a clot because they do not have enough von Willebrand Factor, or their factor is abnormal. Researchers have identified many variations of the disease, but most fall into the following classifications: Type I: This is the most common and mildest form of von Willebrand disease. Levels of von Willebrand factor are lower than normal, and levels of factor VIII may also be reduced. Type II: In these people, the von Willebrand factor itself has an abnormality. Depending on the abnormality, they may be classified as having Type IIa or Type IIb. In Type IIa, the level of von Willebrand factor is reduced, as is the ability of platelets to clump together. In Type IIb, although the factor itself is defective, the ability of platelets to clump together is actually increased. Type III: This is severe von Willebrand disease. These people may have a total absence of von Willebrand factor, and factor VIII levels are often less than 10%. Pseudo (or platelet-type) von Willebrand disease: This disorder resembles Type Jib von Willebrand disease, but the defects appear to be in the platelets, rather than the von Willebrand factor.

The bleeding disease or disorder may be hemophilia. Hemophilia is a well-known but rare bleeding disorder that runs in families. Both men and women have this condition, but almost all people with severe hemophilia are men. However, many women have mild symptoms of hemophilia. This condition is caused by a shortage of clotting factors needed to stop bleeding. Signs of hemophilia include: easy bruising, excessive bleeding after cuts, dental work and surgery, blood in the stool or urine.

The bleeding disease or disorder may be thrombocytopenia. Thrombocytopenia is the medical term for a low blood platelet count. Thrombocytopenia often occurs as a result of a separate disease or disorder. For example, a bone marrow disorder such as leukemia can interfere with platelet production and reduce the number of platelets in your blood. Or sometimes, thrombocytopenia occurs because of an immune system malfunction that develops for unknown reasons. In addition, thrombocytopenia may occur as a reaction to a medication.

Other rare coagulation disorders are congenital fibrinogen defects. They include afibrinogenemia and hypofibrinogenemia, and dysfibrinogenemia. The first two are called quantitative abnormalities because they have to do with an absent or low quantity of fibrinogen. The third is called a qualitative abnormality because the fibrinogen does not work well.

Fibrinogen, also known as Factor I, is needed for most types of platelet aggregation. People who have a Factor I deficiency have a combined bleeding disorder, meaning that both platelets and clotting are abnormal. Afibrinogenemia is the complete absence of fibrinogen. Hypofibrinogenemia is a low level of fibrinogen—less than 100 mg in 1 dL of blood. Both conditions are inherited in an autosomal fashion and can affect males and females.

The severity of the disorder is related to the amount of fibrinogen. Afibrinogenemia is usually discovered in newborns and can cause bleeding from the umbilical cord, genitourinary tract, or central nervous system. People with hypofibrinogenemia may have little, moderate, or severe bleeding.

Dysfibrinogenemias are due to variations in the Factor I molecule. More than 70 different types of dysfibrinogenemia have been identified. Few people who have any of these disorders suffer symptoms, although some are predisposed to form blood clots (thrombosis).

In any of the methods as described herein the non-neuronal cell may be any type of cell. In certain examples, the non-neuronal cell is a white blood cell. There are several different types of white blood cells. Granulocytes are leukocytes that are characterized by the presence of differently staining granules in the cytoplasm when viewed under light microscopy. These granules are membrane-bound enzymes which primarily act in the digestion of endocytosed particles. There are three types of granulocytes: neutrophils, basophils, and eosinophils, which are named according to their staining properties. Agranulocytes are leukocytes that are characterized by the absence of specific granules in their cytoplasm. These include lymphocytes, monocytes, and macrophages.

In other certain examples, the non-neuronal cell is an endothelial cell. In preferred embodiments, the neuronal cell is selected from, but not limited to, platelets, endothelial cells, sub-endothelial cells, leukocytes and megakaryocytes.

The invention features methods of diagnosis. In certain aspects the invention features diagnosing a subject as having or having a propensity to develop a thrombotic disease or disorder comprising measuring plasma levels of glutamate in a sample from the subject, wherein increased levels of plasma glutamate indicate that the subject has or has a propensity to develop a thrombotic disease or disorder.

According to any of the methods as described herein, the activity of glutamate receptors can be inhibited by a small molecule inhibitor, a nucleic acid inhibitor or an antibody.

The term "small molecule" inhibitor as used herein is meant to refer to a molecule of less than about 3,000 daltons having glutamate receptor inhibitory activity. In certain preferred embodiments, the small molecule inhibitor is selected from the group consisting of: CNQX, NBQX, GYKI52466, GYKI53655, GYKI47261, cyclothiazide, YM90K, Zonampel (YM872), YM928, Perampanel (E2007), CP-465, 022, ZK200775, Talampanel (LY300164), and Tezampanel (NGX424), LY382884, NS-102, UBP301, CX-516, CX-717, topiramate, and philanthotoxin-343, and pharmaceutically acceptable salts, prodrugs, esters, and hydrates thereof.

Diseases and Disorders Treated

The invention features methods and compositions for treating or preventing a thrombotic disease or disorder. By thrombotic disease or disorder is meant any disease caused by the occlusion of blood vessels. A thrombotic disease or disorder includes, but is not limited to, stroke, myocardial infarction (MI), acute coronary syndrome, thrombosis, thrombocytic thrombocytopenic purpura (TTP), vascular occlusion, deep vein thrombosis (DVT), embolism, pulmonary embolism, sepsis, and hereditary hemolytic syndrome (HHS).

Cardiovascular disease and stroke are major causes of morbidity and mortality. Although many pathophysiologic processes play a role in the chronic development of cardiovascular disease, thrombosis is often the event that precipitates stroke and acute coronary syndromes.

Thrombosis is initiated by receptors on resting platelets responding to activation initiators such as vWF, thrombin, adenosine diphosphate (ADP), and collagen.

Thrombocytopenia may be caused by cancer chemotherapy, disseminated intravascular coagulation (DIC), hemolytic anemia, hypersplenism, idiopathic thrombocytopenic purpura (ITP), leukemia, massive blood transfusion, or prosthetic heart valve. These are not the only causes but serve as examples.

Thrombocytosis may be caused by anemia, certain malignancies, early CML, polycythemia vera, post-splenectomy syndrome, or primary thrombocytosis. These are not the only causes but serve as examples.

In exemplary embodiments, a thrombotic disease or disorder is selected from, but not limited to stroke, myocardial infarction (MI), acute coronary syndrome, including patients undergoing thrombolysis or those with stents or percutaneous coronary intervention (PCI), or both, post-myocardial infarction (MI), in patients who have received thrombolysis or those with percutaneous coronary intervention or post coronary bypass surgery, thrombosis, thrombocytic thrombocytopenic purpura (TTP), vascular occlusion, deep vein thrombosis (DVT), embolism, pulmonary embolism, sepsis, and hereditary hemolytic syndrome (HHS), and other thrombotic events in patients at risk for such events (for example, but not limited to post-orthopedic surgery, medical patients, cancer patients, surgical patients).

A stroke occurs when a blood vessel that brings oxygen and nutrients to the brain bursts or is clogged by a blood clot or some other mass. Because of this rupture or blockage, part of the brain doesn't get the blood and oxygen it needs. Deprived of oxygen, nerve cells in the affected area of the brain cannot work, and die within minutes. And when nerve cells can't work, the part of the body they control can't work either. The devastating effects of a severe stroke are often permanent because dead brain cells aren't replaced. There are two main types of stroke. One (ischemic stroke) is caused by blockage of a blood vessel; the other (hemorrhagic stroke) is caused by bleeding.

Ischemic stroke is the most common type. It accounts for about 88 percent of all strokes. It occurs when a blood clot (thrombus) forms and blocks blood flow in an artery bringing blood to part of the brain. Blood clots usually form in arteries damaged by fatty buildups, called atherosclerosis. When the blood clot forms within an artery of the brain, it's called cerebral thrombotic stroke. These often occur at night or first thing in the morning. Another distinguishing feature is that very often they are preceded by a transient ischemic attack. This is also called a TIA or "warning stroke."

A wandering clot (an embolus) or some other particle that forms away from the brain, usually in the heart, may also cause an ischemic stroke. This is called cerebral embolism. The clot is carried by the bloodstream until it lodges in an artery leading to or in the brain, blocking the flow of blood. The most common cause of these emboli is blood clots that form during atrial fibrillation (AF). AF is a disorder found in about 2.2 million Americans. It's responsible for 15-20 percent of all strokes. In AF, the heart's two small upper chambers (the atria) quiver instead of beating effectively. Some blood isn't pumped completely out of them when the heart beats, so it pools and clots. When a blood clot enters the circulation and lodges in a narrowed artery of the brain, a stroke occurs. The compounds and methods of the invention can preferably be used to treat a patient that is suffering from or at risk for a stroke. In particular embodiments, the compounds and methods of the invention can be used to delay or prevent platelet activity. In other particular embodiments, the compounds and methods of the invention can be used to delay or prevent the formation of an embolus.

Myocardial infarction occurs when myocardial ischemia exceeds a critical threshold and overwhelms myocardial cellular repair mechanisms that are designed to maintain normal operating function and hemostasis. Acute myocardial infarction (MI) is defined as death or necrosis of myocardial cells. It is a diagnosis at the end of the spectrum of myocardial ischemia or acute coronary syndromes.

Myocardial infarction is the leading cause of death in the United States (US) as well as in most industrialized nations throughout the world. It is estimated that approximately 800,000 people in the US are affected and in spite of a better awareness of presenting symptoms, 250,000 die prior to presentation to a hospital. (www.acc.org/clinical/guidelines and www.americanheart.org). The survival rate for US patients hospitalized with MI is approximately 90% to 95%. In general, MI can occur at any age, but its incidence rises with age. The actual incidence is dependent upon predisposing risk factors for atherosclerosis, which are discussed below. Approximately 50% of all MI's in the US occur in people younger than 65 years of age. However, in the future, as demographics shift and the mean age of the population increases, a larger percentage of patients presenting with MI will be older than 65 years. (Rubin E, et al. Eds. Essential Pathology. 2nd ed. Philadelphia, Pa.: J B Lippincott Co; 1995; Cotran R S et al., eds. Robbins Pathologic Basis of Disease. 5th ed. Philadelphia, Pa.: W B Saunders Co; 1994). Risk factors for heart attack and coronary artery disease include, but are not limited to, hereditary factors, gender (male), diabetes, advanced age, high blood pressure, smoking, high fat diet, unhealthy cholesterol levels, especially high LDL ("bad") cholesterol and low HDL ("good") cholesterol. Blood tests can be used to determine if a subject is at a greater risk for heart attack. These include, but are not limited to, troponin I and troponin T, CPK and CPK-MB, serum myoglobin.

Most MIs are caused by a disruption in the vascular endothelium associated with an unstable atherosclerotic plaque that stimulates the formation of an intracoronary thrombus, which results in coronary artery blood flow occlusion. If such an occlusion persists long enough (20 to 40 min), irreversible myocardial cell damage and cell death will occur (DeWood M A, et al. N Engl J Med. 1986; 315:417-423).

The severity of an MI is dependent on three factors: the level of the occlusion in the coronary artery, the length of time of the occlusion, and the presence or absence of collateral circulation. Generally speaking, the more proximal the coronary occlusion, the more extensive is the amount of myocardium at risk of necrosis. The larger the MI, the greater is the chance of death due to a mechanical complication or pump failure. The longer the time period of vessel occlusion, the greater the chances of irreversible myocardial damage distal to the occlusion.

The compounds and methods of the invention can preferably be used to treat a patient that is suffering from or at risk for MI. In particular embodiments, the compounds and methods of the invention can be used to delay or prevent platelet activity. In other particular embodiments, the compounds and methods of the invention can be used to delay or prevent the formation or progression of a blood clot.

Acute Coronary Syndrome is a name given to three types of coronary artery disease that are associated with sudden rupture of plaque inside the coronary artery: unstable angina, Non-ST segment elevation myocardial infarction or heart attack (NSTEMI), or ST segment elevation myocardial infarction or heart attack (STEMI). The location of the blockage, the length of time that blood flow is blocked and the amount of damage that occurs determines the type of acute coronary syndrome.

Unstable angina is a new symptom or a change from stable angina. The angina may occur more frequently, occur more easily at rest, feel more severe, or last longer. Although this angina can often be relieved with oral medications, it is unstable and may progress to a heart attack. Usually more intense medical treatment or a procedure is required.

Unstable angina is an acute coronary syndrome and should be treated as a medical emergency.

Heart attack: Non-ST segment elevation myocardial infarction (NSTEMI): This heart attack, or MI, does not cause changes on an electrocardiogram (ECG). However, chemical markers in the blood indicate that damage has occurred to the heart muscle. In NSTEMI, the blockage may be partial or temporary, and so the extent of the damage relatively minimal.

Heart attack: ST segment elevation myocardial infarction (STEMI): This heart attack, or MI, is caused by a prolonged period of blocked blood supply. It affects a large area of the heart muscle, and so causes changes on the ECG as well as in blood levels of key chemical markers. More information is available publicly on the world wide web at clevelandclinic.org/heartcenter/pub/guide/disease/cad/mi_types.htm.

Thrombotic thrombocytopenic purpura (TTP) is a disorder of blood coagulation that presents classically with the pentad of fever, thrombocytopenia, microangiopathic hemolytic anemia, renal dysfunction and mental status changes. "Hyaline" microthrombi composed primarily of platelets and Von Willebrand Factor (VWF) are found in the small vessels of affected organs and represent the pathological hallmark of the disease. TTP causes multiple blood clots to form in blood vessels around the body. The compounds and methods of the invention can preferably be used to treat a patient that is suffering from or at risk for TTP. In particular embodiments, the compounds and methods of the invention can be used to delay or prevent platelet activity. In other particular embodiments, the compounds and methods of the invention can be used to delay or prevent the formation or progression of a blood clot.

Deep Vein Thrombosis is a condition resulting from the formation of a blood clot thrombus inside a deep vein, commonly located in the calf or thigh. DVT affects up to 2 million people each year in the U.S. and its primary complication, pulmonary embolism (PE), claims approximately 300,000 lives annually (information from dvt.net, a publicly available site on the world wide web). DVT occurs when the blood clot either partially or completely blocks the flow of blood in the vein. When the rhythm of circulation of the blood slows down due to illness, injury, or immobility, there is a tendency for blood to accumulate or "pool." A static pool of blood offers an ideal environment for clot formation and poses a potential risk for DVT. The signs and symptoms of deep vein thrombosis (DVT) may be related to DVT itself or to pulmonary embolism (PE). Only about half of the people with DVT have symptoms. These symptoms occur in the leg affected by the deep vein clot. They include: Swelling of the leg or along a vein in the leg, pain or tenderness in the leg, which may be felt only when standing or walking, increased warmth in the area of the leg that is swollen or in pain, red or discolored skin on the leg.

Some people are unaware that they have DVT until they have signs or symptoms of pulmonary embolism (PE). Symptoms of PE include, unexplained shortness of breath, pain with deep breathing, coughing up blood.

PE is a sudden blockage in a lung artery, usually due to a blood clot that traveled to the lung from a vein in the leg. A clot that forms in one part of the body and travels in the bloodstream to another part of the body is called an embolus. At least 100,000 cases of PE occur each year in the United States. PE is the third most common cause of death in hospitalized patients. If left untreated, about 30 percent of patients with PE will die. Most of those who die do so within the first few hours of the event. PE can cause permanent damage to part of your lung from lack of blood flow to lung tissue, low oxygen levels in your blood, damage to other organs in your body from not getting enough oxygen. If the blood clot is large, or if there are many clots, PE can cause death.

In particular embodiments, the compounds and methods of the invention can be used to treat or prevent DVT or PE. In other particular embodiments, the compounds and methods of the invention can be used to delay or prevent the formation of an embolus.

Information on both PE and DVT is publicly available on the world wide web at nhlbi.nih.gov/health/dci/Diseases/pe/pe_what.html.

III. Therapeutics

Glutamate Receptor Modulators

The invention is based on the finding that glutamate receptors modulate platelet activity and thrombosis. These results have important implications for treating and preventing thrombotic diseases where plasma glutamate levels can rise significantly.

The invention features in one aspect pharmaceutical compositions comprising a compound that delays or inhibits platelet activation, and a pharmaceutically acceptable excipient. The invention features in other certain aspects pharmaceutical compositions comprising a compound that delays or inhibits platelet activity, and a pharmaceutically acceptable excipient, wherein the compound is capable of modulating platelet activation, aggregation, thrombosis, adherence or clotting.

The invention also features in other aspects pharmaceutical compositions comprising a compound that increases platelet activity, and a pharmaceutically acceptable excipient. The invention features in other certain aspects pharmaceutical compositions comprising a compound that increases platelet activity, and a pharmaceutically acceptable excipient, wherein the compound is capable of modulating platelet activation, aggregation, thrombosis, adherence or clotting.

Pharmacologic Inhibitors

Any number of small molecule inhibitors can be used to inhibit glutamate receptor activity.

The term "small molecule" inhibitor as used herein is meant to refer to a molecule of less than about 3,000 daltons having glutamate receptor inhibitory activity. In certain embodiments, small molecule inhibitors can have inhibitory activity against one or more glutamate receptor type, e.g. a small molecule inhibitor that is an AMPA receptor inhibitor, a KA receptor inhibitor, or that is both a AMPA receptor inhibitor and a KA receptor inhibitor.

In certain embodiments, known glutamate inhibitors are used, for example, but not limited to CNQX, NBQX, GYKI52466, GYKI53655, GYKI47261, cyclothiazide, YM90K, Zonampel (YM872), YM928, Perampanel (E2007), CP-465,022, ZK200775, Talampanel (LY300164), and Tezampanel (NGX424), LY382884, NS-102, UBP301, CX-516, CX-717, topiramate, and philanthotoxin-343, and pharmaceutically acceptable salts, prodrugs, esters, and hydrates thereof.

In certain embodiments, preferred compounds are ionotropic receptor inhibitors, including but not limited to the inhibitors described in Catarzi et al. in Med Res Rev. 2007 March; 27(2):239-78, and Planells-Cases et al., Current Pharmaceutical Design (2006) 12:3583-3596, both of which are hereby incorporated by reference in their entireties.

1. Quinoxaline-2,3-Dione Derivatives

Quinoxalinedione derivatives are a chemical class of competitive AMPA receptor antagonists. Quinoxalinediones are described in Honore, T., Neuroscience Letters., 1988., 87(1-

2): 104-108 and Catarzi et al. in Med Res Rev. 2007 March; 27(2):239-78, which is hereby incorporated by reference in its entirety.

Exemplary compounds include CNQX (-cyano-7-nitro-quinoxaline-2,3-dione) and NBQX ((2,3-dihydroxy-6-nitro-7-sulfamoyl-benzo[f]quinoxaline-2,3-dione).

CNQX is represented by the formula:

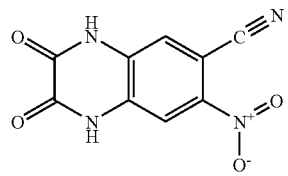 [SMILES: N#Cc1cc2[nH]c(=O)c(=O)[nH]c2cc1[N+](=O)[O-]]

There are at least 22 similar compounds to CNQX that can be used in the methods of the invention that include:
7-nitro-2,3-dioxo-1,4-dihydroquinoxaline-6-carbonitrile; 8-nitro-2,3-dioxo-1,4-dihydroquinoxaline-6-carbonitrile; 7-methyl-8-nitro-2,3-dioxo-1,4-dihydroquinoxaline-6-carbonitrile; 6-methyl-5,7-dinitro-1,4-dihydroquinoxaline-2,3-dione; 6-methyl-7-nitro-1,4-dihydroquinoxaline-2,3-dione; 5-methyl-7-nitro-1,4-dihydroquinoxaline-2,3-dione; 6-nitro-7-(trifluoromethyl)-1,4-dihydroquinoxaline-2,3-dione; 6-ethynyl-7-nitro-1,4-dihydroquinoxaline-2,3-dione; N-[7-nitro-2,3-dioxo-6-(trifluoromethyl)-4H-quinoxalin-1-yl]acetonitrilium; 5,6-dimethyl-7-nitro-1,4-dihydroquinoxaline-2,3-dione; 5,6-dinitro-7-(trifluoromethyl)-1,4-dihydroquinoxaline-2,3-dione; 5,7-dinitro-6-(trifluoromethyl)-1,4-dihydroquinoxaline-2,3-dione; 5,7-dimethyl-6-nitro-1,4-dihydroquinoxaline-2,3-dione; -[(7-nitro-2,3-dioxo-1,4-dihydroquinoxalin-5-yl)methylamino]acetonitrile; 2-[(7-nitro-2,3-dioxo-1,4-dihydroquinoxalin-5-yl)methylamino]acetonitrile hydrobromide; 5-(aminomethyl)-7-nitro-1,4-dihydroquinoxaline-2,3-dione; 7-iodo-6-methyl-5-nitro-1,4-dihydroquinoxaline-2,3-dione 4,7-dimethyl-6-nitro-1H-quinoxaline-2,3-dione; 7-methyl-5-nitro-1,4-dihydroquinoxaline-2,3-dione; 7-fluoro-6-methyl-5-nitro-1,4-dihydroquinoxaline-2,3-dione; 4-(6-nitro-2,3-dioxo-4,7,8,10-tetrahydro-1H-pyrido[3,4-f]quinoxalin-9-yl)butanenitrile. Prodrugs of any of the above are encompassed by the invention.

NBQX is represented by the formula:

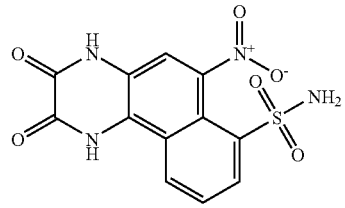 [SMILES: NS(=O)(=O)c1cccc2c1c([N+](=O)[O-])cc1[nH]c(=O)c(=O)[nH]c12]

There are at least 33 similar compounds to NBQX that can be used in the methods of the invention that include, but are not limited to:
6-nitro-2,3-dioxo-1,4-dihydrobenzo[f]quinoxaline-7-sulfonamide; disodium 6-nitro-2,3-dioxo-1,4-dihydrobenzo[f]quinoxaline-7-sulfonamide; 1-methyl-6-nitro-2,3-dioxo-4H-benzo[f]quinoxaline-7-sulfonamide; 6-nitro-2,3-dioxo-1,4-dihydrobenzo[f]quinoxaline-8-sulfonamide; 6-nitro-2,3-dioxo-1,4-dihydrobenzo[f]quinoxaline-9-sulfonamide; N,N-dimethyl-6-nitro-2,3-dioxo-1,4-dihydrobenzo[f]quinoxaline-8-sulfonamide; N-methyl-6-nitro-2,3-dioxo-1,4-dihydrobenzo[f]quinoxaline-8-sulfonamide; N-methyl-6-nitro-2,3-dioxo-1,4-dihydrobenzo[f]quinoxaline-9-sulfonamide; 6-nitro-2,3-dioxo-1,4-dihydrobenzo[f]quinoxaline-7,9-disulfonamide; 7-methylsulfonyl-6-nitro-1,4-dihydrobenzo[f]quinoxaline-2,3-dione; N-ethyl-6-nitro-2,3-dioxo-1,4-dihydrobenzo[f]quinoxaline-8-sulfonamide; 7-aminoperoxysulfanyl-6-nitro-1,4-dihydrobenzo[f]quinoxaline-2,3-dione; 6-amino-2,3-dioxo-1,4-dihydrobenzo[f]quinoxaline-7-sulfonamide; 6-nitro-2,3-dioxo-N-phenyl-1,4-dihydrobenzo[f]quinoxaline-8-sulfonamide; carbonic acid; 1-methyl-6-nitro-2,3-dioxo-4H-benzo[f]quinoxaline-7-sulfonamide; 1-methyl-1-[(6-nitro-2,3-dioxo-1,4-dihydrobenzo[f]quinoxalin-8-yl)sulfonyl]urea; 2-(6-nitro-2,3-dioxo-7-sulfamoyl-4H-benzo[h]quinoxalin-1-yl)acetic acid; (6-nitro-2,3-dioxo-7-sulfamoyl-4H-benzo[h]quinoxalin-1-yl)methylphosphonic acid; 8-methylsulfonyl-6-nitro-1,4-dihydrobenzo[f]quinoxaline-2,3-dione; 6-amino-2,3-dioxo-1,4-dihydrobenzo[f]quinoxaline-8-sulfonamide; 6-amino-2,3-dioxo-1,4-dihydrobenzo[f]quinoxaline-8-sulfonamide hydrochloride; 2-[(6-nitro-2,3-dioxo-1,4-dihydrobenzo[f]quinoxalin-8-yl)sulfonyl]acetamide; 1-(6-nitro-2,3-dioxo-7-sulfamoyl-4H-benzo[h]quinoxalin-1-yl)ethylphosphonic acid; 1-(6-nitro-2,3-dioxo-7-sulfamoyl-4H-benzo[h]quinoxalin-1-yl)propylphosphonic acid; 5-dimethylamino-N-[(7-nitro-2,3-dioxo-1,4-dihydroquinoxalin-5-yl)methyl]naphthalene-1-sulfonamide; N-methyl-N-[(6-methyl-7-nitro-2,3-dioxo-1,4-dihydroquinoxalin-5-yl)methyl]naphthalene-2-sulfonamide; 1-(6-nitro-2,3-dioxo-7-sulfamoyl-4H-benzo[h]quinoxalin-1-yl)ethyl hydrogen carbonate; 1-(diethoxyphosphorylmethyl)-6-nitro-2,3-dioxo-4H-benzo[f]quinoxaline-7-sulfonamide; 10-bromo-6-nitro-2,3-dioxo-1,4-dihydrobenzo[f]quinoxaline-7-sulfonamide; 2-(6-nitro-2,3-dioxo-7-sulfamoyl-4H-benzo[h]quinoxalin-1-yl)propanoic acid; disodium 7-azanidylsulfonyl-6-nitro-3-oxo-4H-benzo[h]quinoxalin-2-olate; N,4-dimethyl-N-[(6-methyl-7-nitro-2,3-dioxo-1,4-dihydroquinoxalin-5-yl)methyl]benzenesulfonamide. Prodrugs of any of the above are encompassed by the invention.

In certain embodiments, the compounds may be of the general formula:

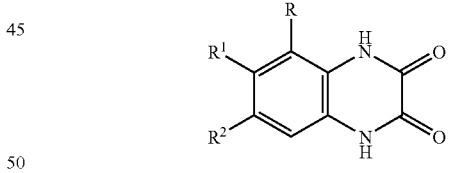

or a pharmaceutically acceptable salt thereof, wherein

R is a 5-membered ring heteroaryl group containing 3 or 4 nitrogen heteroatoms which is linked to the quinoxalinedione ring by a ring carbon or nitrogen atom, or is a 6-membered ring heteroaryl group containing from 1 to 3 nitrogen heteroatoms which is linked to the quinoxalinedione ring by a ring carbon atom, either of said groups being optionally benzo-fused and optionally substituted, including in the benzo-fused portion, by 1 or 2 substituents each independently selected from $C_1$-$C_4$ alkyl, $C_2$-$C_4$ alkenyl, $C_3$-$C_7$ cycloalkyl, halo, hydroxy, $C_1$-$C_4$ alkoxy, $C_3$-$C_7$ cycloalkyloxy, —COOH, $C_1$-$C_4$ alkoxycarbonyl, —CONR$^3$R$^4$, —NR$^3$R$^4$, —S(O)p ($C_1$-$C_4$ alkyl), —SO$_2$NR$^3$R$^4$, aryl, aryloxy, aryl($C_1$-$C_4$) alkoxy and het, said $C_1$-$C_4$ alkyl being optionally substituted by $C_3$-$C_7$ cycloalkyl, halo, hydroxy, $C_1$-$C_4$ alkoxy, halo($C_1$-$C_4$)alkoxy, $C_3$-$C_7$ cycloalkyloxy, $C_3$-$C_7$ cycloalkyl($C_1$-$C_4$)

alkoxy, —COOH, $C_1$-$C_4$ alkoxycarbonyl, —CONR$^3$R$^4$, —NR$^3$R$^4$, —S(O).sub.p ($C_1$-$C_4$ alkyl), —SO.sub.2 (aryl), —SO.sub.2 NR$^3$R$^4$, morpholino, aryl, aryloxy, aryl($C_1$-$C_4$) alkoxy or het, and said $C_2$-$C_4$ alkenyl being optionally substituted by aryl; R$^1$R$^2$ are each independently selected from H, fluoro, chloro, bromo, $C_1$-$C_4$ alkyl and halo($C_1$-$C_4$)alkyl; R$^3$ and R$^4$ are either each independently selected from H and $C_1$-$C_4$ alkyl or, when taken together, are $C_5$-$C_7$ alkylene; p is 0, 1 or 2. Prodrugs of any of the above are encompassed by the invention.

U.S. Pat. No. 6,376,490, incorporated by reference in its entirety herein, describes 2,3(1H,4H)-quinoxalinedione derivatives and methods of synthesis.

U.S. Pat. No. 6,333,326, incorporated by reference in its entirety herein, also describes 2,3(1H,4H)-quinoxalinedione derivatives.

EP-A-0572852, incorporated by reference in its entirety herein, describes pyrrol-1-yl-substituted 2,3(1H,4H)-quinoxalinedione derivatives.

EP-A-0556393 incorporated by reference in its entirety herein, describes imidazolyl- or triazolyl-substituted 2,3(1H, 4H)-quinoxalinedione derivatives with glutamate receptor antagonising activity.

Pharmaceutically acceptable salts of the compounds include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples are the calcium, lithium, magnesium, potassium, sodium, zinc, ethanolamine, diethanolamine and triethanolamine salts.

For a review on suitable salts see Berge et al, J. Pharm. Sci., 66, 1-19 (1977).

The compounds may be tricyclic quinoxalinedione derivatives. In certain embodiments, the tricyclic quinoxalinedione derivatives are represented by the formula:

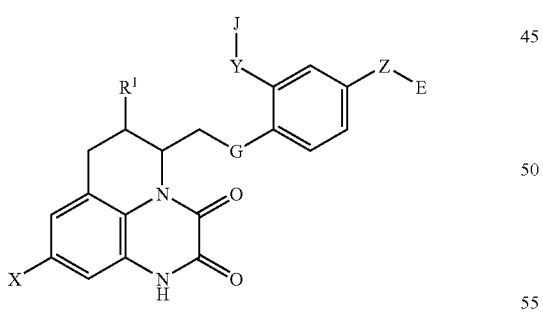

wherein X represents hydrogen, alkyl, halogen, cyano, trifluoromethyl, or nitro; R$^1$ represents hydrogen, alkyl, cycloalkyl, or cycloalkylalkyl; G represents —CONR$^2$— or —N R$^2$CO—, wherein R$^2$ represents hydrogen or alkyl; J represents an acidic group or a group which is convertible thereto in vivo; E represents an basic group or a group which is convertible thereto in vivo; Y represents a single bond, alkylene, alkenylene, substituted alkylene, or Y$^1$-Q-Y$^2$, wherein Y$^1$ represents a single bond or alkylene, Y$^2$ represents alkylene, and Q represents a heteroatom selected from oxygen or sulfur; Z represents alkylene. J and E may be simultaneously in the same molecule. Prodrugs of any of the above are encompassed by the invention.

U.S. Pat. No. 5,719,152, incorporated by reference in its entirety herein, describes tricyclic quinoxalinedione derivatives and methods of use.

Exemplary heterocyclic fused quinoxaline derivatives include:

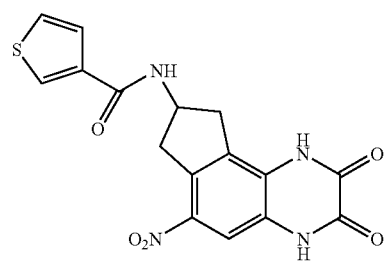

34

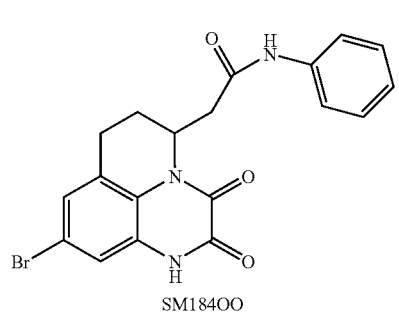

35

SM18400

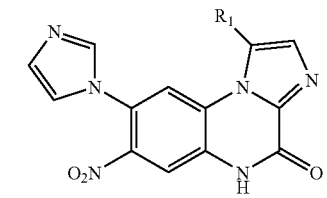

36a R$_1$ = CH$_2$CH$_3$
36b R$_1$ = H

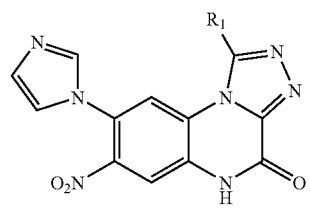

37a R$_1$ = CH$_2$CH$_3$
37b R$_1$ = H

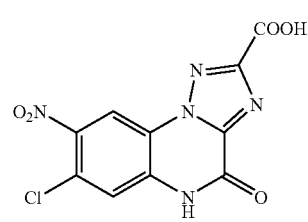

38

-continued

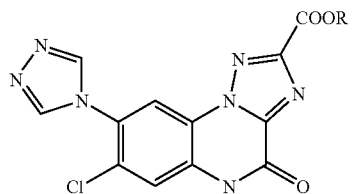

39a R = H TQX173
39b R = Et

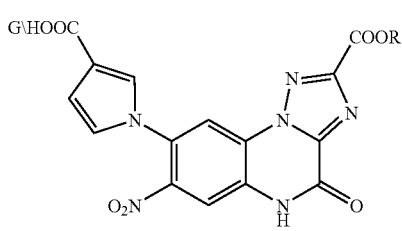

40a R = H
40b R = Et

Other quinoxaline compounds include YM928, YM90K and Zonampanel (YM872) and their derivatives. YM928 has been described in the literature as an AMPA receptor antagonist (Yamashita et al., Naunyn-Schmiedeberg's Archives of Pharmacology, Volume 370, Number 2; August, 2004).

Zonampanel ((1)1 (2H)-quinoxalineacetic acid, 3,4-dihydro-7-(1H-imidazol-1-yl)-6-nitro-2,3-dioxo-, monohydrate; (2) 3,4-dihydro-7-imidazol-1-yl-6-nitro-2,3-dioxo-1(2H)-quinoxalineacetic acid, monohydrate) is manufactured by Yamanouchi Pharmaceutical Co. Ltd. The structure of Zonampanel is shown below:

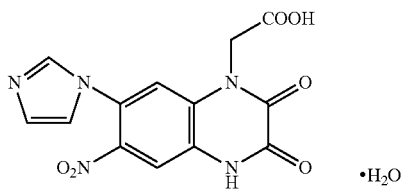

Other quinoxaline derivatives, including YM928, YM90K, PNQK, ZK-20075 and AMP-397A are shown below.

17

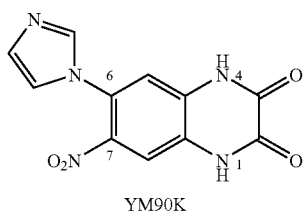

YM90K

-continued

18

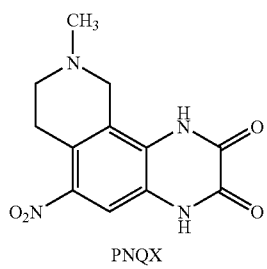

PNQX

20

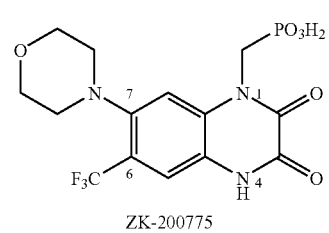

ZK-200775

21

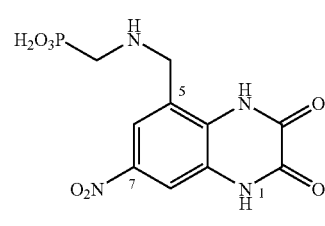

AMP-397A

2. N-4 Substituted Quinoxalin-2,3-Diones

Polar and hydrophilic groups at R4 such as hydroxy, carboxyalkyl, and phosphonoalkyl are, in general, responsible for increased water solubility and improved binding affinity for the AMPA receptor. Initial studies on N-4 acetic acid derivatives were reported on quinoxalinediones bearing simple substituents, such as chlorine atom(s) or methyl group(s) at R6 and/or R7.

Exemplary N-4 Substituted Quinoxalin-2,3-Diones are shown below:

22

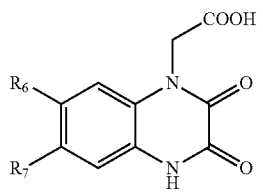

$R_6, R_7 = Cl, CH_3$

23

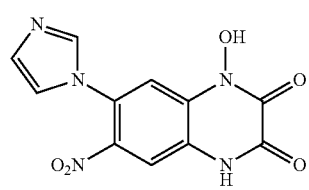

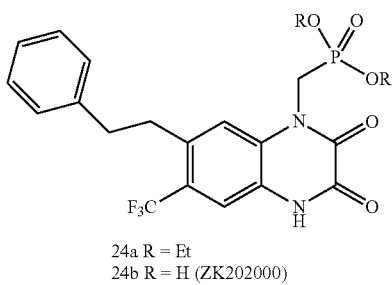

24a R = Et
24b R = H (ZK202000)

⊚ indicates text missing or illegible when filed

3. CS-Substituted Quinoxalin-2,3-Diones and C-6 Substituted Quinoxalin-2,3-Dione Derivatives Compounds bearing at R5 different side chains with amine functionality are useful as glutamate receptor inhibitors. It was found that N-alkylation of the R5 side chain nitrogen atom significantly modified the molecule conformation, thus enhancing the selectivity toward the AMPA receptor subtypes.

Exemplary C5-Substituted Quinoxalin-2,3-Diones are shown below:

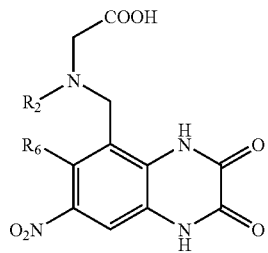

25a $R_6 = R_2 = H$
25b $R_6 = H$ $R_2 = CH_3$
25c $R_6 = CH_3$ $R_2 = H$
25d $R_6 = R_2 = CH_3$

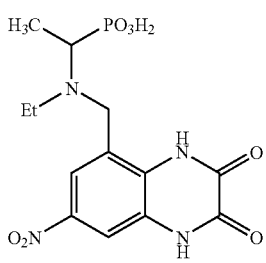

26

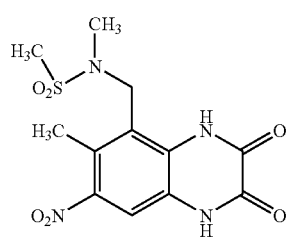

27

C6-Substituted Quinoxalin-2,3-Diones are mostly quinoxalinediones bearing an EWG at R7 and an optional substituent at R4.

Exemplary C6-Substituted Quinoxalin-2,3-Diones are shown below:

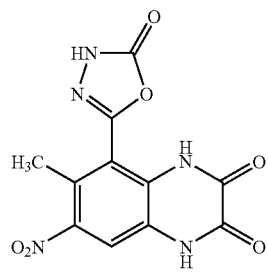

28

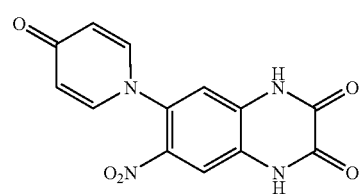

29

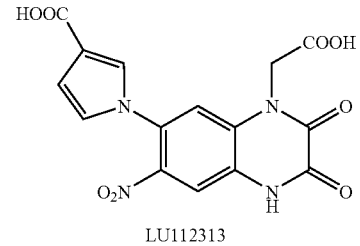

LU112313

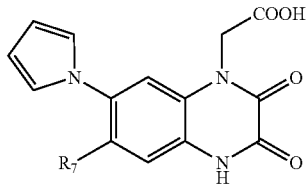

31a $R_7 = NO_2$
31b $R_7 = CF_3$

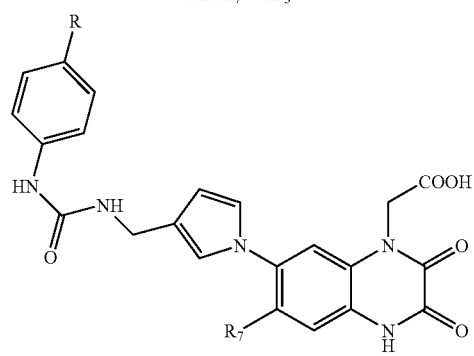

32a $R_7 = NO_2$ R = H
32b $R_7 = CF_3$ R = H
32c $R_7 = CF_3$ R = Br
32d $R_7 = CF_3$ R = $NO_2$
32e $R_7 = CF_3$ R = $CF_3$

-continued

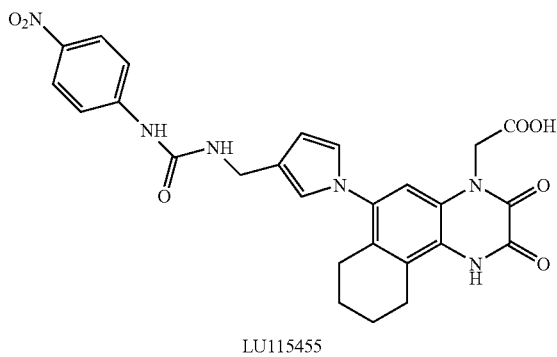

LU115455

4. Benzodiazapines

In certain preferred embodiments, the small molecule inhibitor is a 2,3 benzodiazapine derivative that inhibits glutamate receptor activity. The general formula for benzodiazepine is shown below:

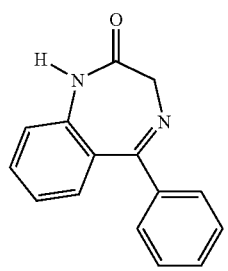

Talampanel (LY300164) is an example of a 2,3 benzodiazapene. The chemical name of Talampanel is (R)-7-acetyl-5-(4-aminophenyl)-8,9-dihydro-8-methyl-7H-1,3-dioxolo[4,5-h][2,3]benzodiazepine.

Other exemplary compounds include GYKI52466 and GYKI47261.

5. Isoquinolines

Isoquinolines are a group of compounds with the heterocyclic ring structure of benzo(c)pyridine. The ring structure is characteristic of the group of opium alkaloids such as papaverine. Exemplary structure is shown below:

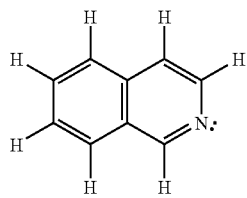

Preferred isoquinoline inhibitors of glutamate receptors are, for example, described in Gilron I. (Curr Opin Investig Drugs. 2001 September; 2(9):1273-8), incorporated by reference in its entirety herein.

U.S. Pat. No. 6,242,462, incorporated by reference in its entirety herein, describes a series of GluR5/KA receptor isoquinoline antagonists.

Exemplary compounds include Tezampanel (LY293558) ((3S,4aR,6R,8aR)-6-[2-(2H-tetrazol-5-yl)ethyl]-1,2,3,4,4a, 5,6,7,8,8a-decahydroisoquinoline-3-carboxylic acid), and NGX426 (the prodrug of Tezampanel). Related compounds include LY 215490, LY-215490, LY 293558, LY 326325, 6-(2-(1H-tetrazol-5-ypethyl)-1,2,3,4,4a,5,6,7,8,8a-decahydroisoquinoline-3-carboxylic acid, (3S,4aR,6R,8aR)-6-(2-(1 (2)H-tetrazole-5yl)ethyl)decahydroisoquinoline-3 carboxylic acid, ted-isoquinoline-3-cooh, Decahydro-6-(2-(1H-tetrazol-5-yl)ethyl)-3-isoquinolinecarboxylic acid, 150131-78-5, 154652-83-2,3-Isoquinolinecarboxylic acid, decahydro-6-(2-(1H-tetrazol-5-yl)ethyl)-, (3S,4aR,6R,8aR)-3-Isoquinolinecarboxylic acid, decahydro-6-(2-(1H-tetrazol-5-yl)ethyl)-, (3S-(3alpha,4aalpha,6beta,8aalpha))-6-(2-(1H-Tetrazol-5-yl)ethyl)-1,2,3,4,4a,5,6,7,8,8a-decahydroisoquinoline-3-carboxylic acid.

The structure of Tezampanel (LY293558) is shown below:

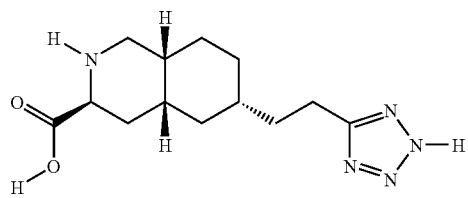 [SMILES: O=C(O)[C@@H]1C[C@H]2C[C@@H](CCc3nn[nH]n3)CC[C@H]2CN1]

There are at least 5 compounds related to Tezampanel (LY293558), including: (3R,4aR,8aR)-6-[2-(2H-tetrazol-5-yl)ethyl]-1,2,3,4,4a,5,6,7,8,8a-decahydroisoquinoline-3-carboxylic acid, (3S,4aR,8aS)-6-[2-(2H-tetrazol-5-yl)ethyl]-1,2,3,4,4a,5,6,7,8,8a-decahydroisoquinoline-3-carboxylic acid, 6-[2-(2H-tetrazol-5-yl)ethyl]-1,2,3,4,4a,5,6,7,8,8a-decahydroisoquinoline-3-carboxylic acid, (3R,4aS,6S,8aS)-6-[2-(2H-tetrazol-5-yl)ethyl]-1,2,3,4,4a,5,6,7,8,8a-decahydroisoquinoline-3-carboxylic acid, (3 S,4aR,6R,8aR)-6-[2-(2H-tetrazol-5-yl)ethyl]-1,2,3,4,4a,5,6,7,8,8a-decahydroisoquinoline-3-carboxylic acid. Prodrugs of any of the above are encompassed by the invention.

There are at least 31 similar compounds related to Tezampanel (LY293558), including, but not limited to: (3R,4aR,8aR)-6-[2-(2H-tetrazol-5-yl)ethyl]-1,2,3,4,4a,5,6,7,8,8a-decahydroisoquinoline-3-carboxylic acid; (3 S,4aR,8aS)-6-[2-(2H-tetrazol-5-yl)ethyl]-1,2,3,4,4a,5,6,7,8,8a-decahydroisoquinoline-3-carboxylic acid; 6-[2-(2H-tetrazol-5-yl)ethyl]-1,2,3,4,4a,5,6,7,8,8a-decahydroisoquinoline-3-carboxylic acid; 6-[2-(2H-tetrazol-5-yl)ethyl]-1,2,3,4,4a,5,6,7,8,8a-decahydroisoquinoline-3-carboxylic acid; (3R,4aS,6S,8aS)-6-[2-(2H-tetrazol-5-ypethyl]-1,2,3,4,4a,5,6,7,8,8a-decahydroisoquinoline-3-carboxylic acid; 6-(2H-tetrazol-5-ylmethyl)-1,2,3,4,4a,5,6,7,8,8a-decahydroisoquinoline-3-carboxylic acid; (3R,4aS,6S,8aS)-6-(2H-tetrazol-5-yl)-1,2,3,4,4a,5,6,7,8,8a-decahydroisoquinoline-3-carboxylic acid; (3S,4aR,6S,8aR)-6-(2H-tetrazol-5-ylmethyl)-1,2,3,4,4a,5,6,7,8,8a-decahydroisoquinoline-3-carboxylic acid; (3S,4aR,6S,8aR)-6-[3-(2H-tetrazol-5-yl)propyl]-1,2,3,4,4a,5,6,7,8,8a-decahydroisoquinoline-3-carboxylic acid; (3S,4aR,6R,8aR)-6-(2H-tetrazol-5-yl)-1,2,3,4,4a,5,6,7,8,8a-decahydroisoquinoline-3-carboxylic acid; (3S,4aR,6S,8aR)-6-[4-(2H-tetrazol-5-yl)butyl]-1,2,3,4,4a,5,6,7,8,8a-decahydroisoquinoline-3-carboxylic acid; (3 S,4aR,6R,8aR)-6-(2H-tetrazol-5-ylmethyl)-1,2,3,4,4a,5,6,7,8,8a-decahydroisoquinoline-3-carboxylic acid; (3S,4aR,6S,8aR)-6-(2H-tetrazol-5-ylmethyl)-1,2,3,4,4a,5,6,7,8,8a-decahydroisoquinoline-3-carboxylic acid; (3S,4aR,6S,8aR)-6-(2H-tetrazol-5-yl)-1,2,3,4,4a,5,6,7,8,8a-decahydroisoquinoline-3-carboxylic acid; Decahydro-6-(2H-tetrazol-5-ylmethyl)-3-isoquinolinecarboxylic acid (3R, 4aS,6R,8aS)-6-(2H-tetrazol-5-ylmethyl)-1,2,3,4,4a,5,6,7,8,8a-decahydroisoquinoline-3-carboxylic acid; 6-(2H-tetrazol-5-ylmethyl)-1,2,3,4,4a,5,6,7,8,8a-decahydroisoquinoline-1-carboxylic acid; (3S,4aR,6S,8aR)-6-[1-(2H-tetrazol-5-yl)propan-2-yl]-1,2,3,4,4a,5,6,7,8,8a-decahydroisoquinoline-3-carboxylic acid; (1R,4aR,8aR)-6-[2-(2H-tetrazol-5-yl)ethyl]-1,2,3,4,4a,5,6,7,8,8a-decahydroisoquinoline-1-carboxylic acid; (3S,4aR,6S,8aR)-6-[4-(2H-tetrazol-5-yl)cyclohexyl]-1,2,3,4,4a,5,6,7,8,8a-decahydroisoquinoline-3-carboxylic acid; 1-(2H-tetrazol-5-ylmethyl)-1,2,3,4,4a,5,6,7,8,8a-decahydroisoquinoline-3-carboxylic acid; 2-ethyl-6-(2H-tetrazol-5-yl)-3,4,4a,5,6,7,8,8a-octahydro-1H-isoquinoline-3-carboxylic acid; 6-(2H-tetrazol-5-ylmethoxymethyl)-1,2,3,4,4a,5,6,7,8,8a-decahydroisoquinoline-3-carboxylic acid; (3S,4aR,6S,8aR)-6-(2H-tetrazol-5-ylmethoxymethyl)-1,2,3,4,4a,5,6,7,8,8a-decahydroisoquinoline-3-carboxylic acid; (3R,4aS,6R,8aS)-6-(2H-tetrazol-5-ylmethoxymethyl)-1,2,3,4,4a,5,6,7,8,8a-decahydroisoquinoline-3-carboxylic acid; (3S,4aR,6S,8aR)-6-(2H-tetrazol-5-ylmethylamino)-1,2,3,4,4a,5,6,7,8,8a-decahydroisoquinoline-3-carboxylic acid; ethyl(3S,4aR,6R,8aR)-6-[2-(2H-tetrazol-5-yl)ethyl]-1,2,3,4,4a,5,6,7,8,8a-decahydroisoquinoline-3-carboxylate; (3S,4aS,6S,8aR)-6-(methyl-(2H-tetrazol-5-ylmethyl)amino)-1,2,3,4,4a,5,6,7,8,8a-decahydroisoquinoline-3-carboxylic acid; 2-methylpropyl(3S,4aR,6R,8aR)-6-[2-(2H-tetrazol-5-yl)ethyl]-1,2,3,4,4a,5,6,7,8,8a-decahydroisoquinoline-3-carboxylate; 3-methylbutyl (3S,4aR,6R,8aR)-6-[2-(2H-tetrazol-5-yl)ethyl]-1,2,3,4,4a,5,6,7,8,8a-decahydroisoquinoline-3-carboxylate; ethyl (3S,4aR,6R,8aR)-6-[2-(2H-tetrazol-5-ypethyl]-1,2,3,4,4a,5,6,7,8,8a-decahydroisoquinoline-3-carboxylate hydrochloride. Prodrugs of any of the above are encompassed by the invention.

U.S. Pat. No. 7,247,644, incorporated by reference in its entirety herein, claims specific oral ester prodrugs of NGX424/Tezampanel/LY293558, including NGX426.

6. Imidazoindenopyrazines

A heterogeneous class of tetracyclic derivatives structurally related to C3-N4 bridged quinoxaline-2,3-diones can also be used. The compounds are based on the optimization of both the 10H-imidazo[1,2-a]indeno[1,2-e]pyrazin-4-one 328,335 and the corresponding 9-acetic acid derivative.

Exemplary compounds are shown below:

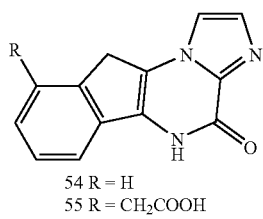

54 R = H
55 R = CH₂COOH

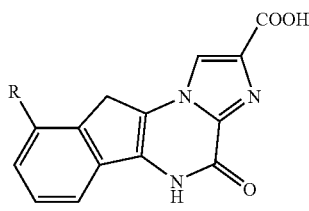

56 R = H
57 R = CH₂COOH
RPR 117824

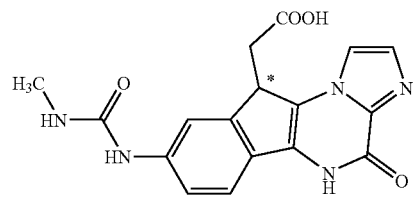

58

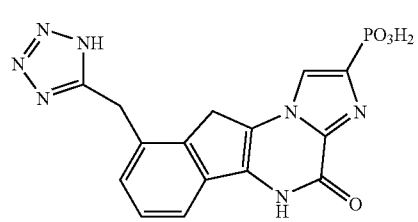

59

CP-465,022 is a selective noncompetitive AMPA receptor antagonist. Menniti et al. (Stroke, 34 (1): 171. (2003)), incorporated by reference in its entirety herein), described the potent inhibitory effects of CP-465,022 on AMPA receptor-mediated hippocampal synaptic transmission.

Other Antagonists

AMPA and Kainate receptors are built from closely related subunits (AMPA-GluR1-4; Kainate-GluR5-7, KA-1,2). At times, the diagnostic agonists for these two receptors (AMPA and kainate, respectively) also activate the other receptor. Thus, it can be challenging to identify compounds that can discriminate between these closely related receptors. Another challenge lies in developing pharmacological agents that can discriminate between AMPA or kainate receptors that contain particular subunits.

AMPA itself shows a good selectivity for AMPA receptors over kainate receptors (10-20 fold higher affinity for GluR1-4 over a representative kainate subunit, GluR5). However, it shows no selectivity for different AMPA receptor subunits. In contrast, compounds based on willardine are not only more selective for AMPA receptors than AMPA itself (5-fluorowillardiine has a 70-150 fold higher affinity for GluR1,2 over GluR5), but also shows selectivity for AMPA receptor subunits. 5-fluorowillardiine shows a 10-20 fold selectivity for GluR1 and 2 over GluR4, while 5-chloro-6-azawillardiine shows some selectivity for GluR4 over GluR1 and 2, but at the cost of losing selectivity for AMPA over kainate receptors. 5-iodo-6-azawillardiine shows a similar pattern of selectivity. The structures of AMPA, 5-F-Will and 5-Cl-6-Aza-Will are shown below:

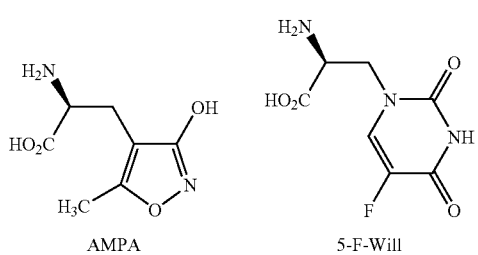

AMPA            5-F-Will

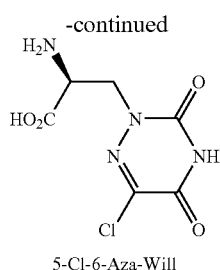

5-Cl-6-Aza-Will

A number of agonists show selectivity for kainate receptors over AMPA receptors. Apart from kainate itself, ATPA and 5-iodowillardiine show high degrees of selectivity for GluR5 over AMPA receptor subunits (1400 and 700 fold, respectively). Neither ATPA or 5-iodowillardiine significantly activate GluR6; however, both have been shown to have weak agonist activity at GluR6/KA2 heteromers. 5-iodowillardiine also has weak agonist activity at GluR7/KA2 heteromeric receptors. Interestingly, 5-iodowillardiine also shows a degree of selectivity for GluR1 and 2 over GluR4, whereas this is reversed for 5-iodo-6-azawillardiine (compare this with 5-Cl-6-azawill). This compound also shows a similar affinity for GluR5. Thus far there are no selective agonists for any other kainate receptor subunits. The structures of kainate, ATPA, 5-I-Will and 5-I-6-AzaWill are shown below:

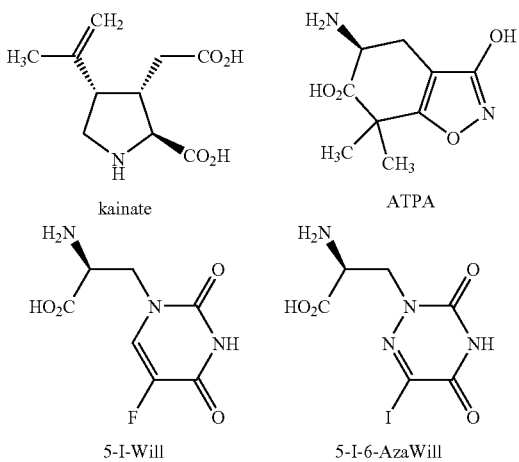

The compound Topiramate may be an AMPAR antagonist, and in particular a Glu5 antagonist. Work by Dudek F. E. et al, (J Neurosci 2003; 23:7069-7074), incorporated by reference in its entirety herein, reports that topirimate has been reported to interact with various ion channel types, including α-amino-3-hydroxy-5-methyl-4-isoxazolepropionate (AMPA)/kainate receptors, and thus may have potential in the methods of the invention as an AMPAR antagonist.

LY382884 (an isoquinoline), NS-102 and UBP301 are further kainate antagonists, and (R)-3,4,-DCPG, GYKI53655, and cyclothiazide are further AMPA antagonists that can be used according to methods of the invention as described herein.

Other AMPA or kainate antagonists include NS102, LY382884, LY377770, UBP296, UBP301, UBP302.

Other antagonists include CX-516, CX-717.

It is understood by one of ordinary skill in the art that any of the compounds as described or envisioned herein include pharmaceutically acceptable salts, prodrugs, esters, and hydrates thereof.

AMPAR Agonists

In certain embodiments, an AMPAR agonist may be administered. Examplary AMPAR agonists include, but are not limited to AMPA, CX-516, LY450108, LY451395, polyamines, S-(−)-5-fluorowillardine, (RS)-Willardine, and Ampakines.

The compounds as described herein can be obtained from commercial sources (TorreyPines Therapeutics, Eli Lilly, AG Scientific, Pfizer, BristolMyers), or can be or synthesized by conventional methods using commercially available starting materials and reagents.

Oligonucleotide Agents

As used herein, an "oligonucleotide agent" refers to a single stranded oligomer or polymer of ribonucleic acid (RNA) or deoxyribonucleic acid (DNA) or both or modifications thereof, which is antisense with respect to its target. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Oligonucleotide agents include both nucleic acid targeting (NAT) oligonucleotide agents and protein-targeting (PT) oligonucleotide agents. NAT and PT oligonucleotide agents refer to single stranded oligomers or polymers of ribonucleic acid (RNA) or deoxyribonucleic acid (DNA) or both or modifications thereof. NATs designed to bind to specific RNA or DNA targets have substantial complementarity, e.g., at least 70, 80, 90, or 100% complementary, with at least 10, 20, or 30 or more bases of a target nucleic acid, and include antisense RNAs, microRNAs, antagomirs and other non-duplex structures which can modulate expression. The NAT oligonucleotide agents can target any nucleic acid, e.g., a miRNA, a pre-miRNA, a pre mRNA, an mRNA, or a DNA. These NAT oligonucleotide agents may or may not bind via Watson-Crick complementarity to their targets. PT oligonucleotide agents bind to protein targets, preferably by virtue of three-dimensional interactions, and modulate protein activity. They include decoy RNAs, aptamers, and the like.

Single Stranded Ribonucleic Acid

Oligonucleotide agents include microRNAs (miRNAs). MicroRNAs are small noncoding RNA molecules that are capable of causing post-transcriptional silencing of specific genes in cells such as by the inhibition of translation or through degradation of the targeted mRNA. An miRNA can be completely complementary or can have a region of non-complementarity with a target nucleic acid, consequently resulting in a "bulge" at the region of non-complementarity. The region of noncomplementarity (the bulge) can be flanked by regions of sufficient complementarity, preferably complete complementarity to allow duplex formation. Preferably, the regions of complementarity are at least 8 to 10 nucleotides long (e.g., 8, 9, or 10 nucleotides long). A miRNA can inhibit gene expression by repressing translation, such as when the microRNA is not completely complementary to the target nucleic acid, or by causing target RNA degradation, which is believed to occur only when the miRNA binds its target with perfect complementarity. The invention also can include double-stranded precursors of miRNAs that may or may not form a bulge when bound to their targets.

In a preferred embodiment an oligonucleotide agent featured in the invention can target an endogenous miRNA or pre-miRNA. The oligonucleotide agent featured in the invention can include naturally occurring nucleobases, sugars, and covalent internucleoside (backbone) linkages as well as oligonucleotides having non-naturally-occurring portions that function similarly. Such modified or substituted oligonucleotides are often preferred over native forms because of desirable properties such as, for example, enhanced cellular uptake, enhanced affinity for the endogenous miRNA target, and/or increased stability in the presence of nucleases. An oligonucleotide agent designed to bind to a specific endogenous miRNA has substantial complementarity, e.g., at least 70, 80, 90, or 100% complementary, with at least 10, 20, or 25 or more bases of the target miRNA.

A miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors can have a length of 70-100 nucleotides and have a hairpin conformation. MicroRNAs can be generated in vivo from pre-miRNAs by enzymes called Dicer and Drosha that specifically process long pre-miRNA into functional miRNA. The microRNAs or precursor mi-RNAs featured in the invention can be synthesized in vivo by a cell-based system or can be chemically synthesized. MicroRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting.

An miRNA or a pre-miRNA can be constructed using chemical synthesis and/or enzymatic ligation reactions using procedures known in the art. For example, an miRNA or a pre-miRNA can be chemically synthesized using naturally occurring nucleotides or variously modified nucleotides designed to increase the biological stability of the molecules or to increase the physical stability of the duplex formed between the miRNA or a pre-miRNA and target nucleic acids, e.g., phosphorothioate derivatives and acridine substituted nucleotides can be used. Other appropriate nucleic acid modifications are described herein. Alternatively, the miRNA or pre-miRNA nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Preferably, glutamate receptor expression may be inhibited ex vivo by the use of any method which results in decreased transcription of the gene encoding a glutamate receptor. Exemplary glutamate receptors include, but are not limited to, kainate (KA) receptors, N methyl-D-aspartate (NMDA) receptors, and alpha($\alpha$)-amino-3-hydroxy-5-methyl-4-isoxazolepropionic acid (AMPA) receptors (AMPAR). The GenBank Accession No. for the amino acid sequence of an exemplary AMPAR subunit 1 is NP_000818. The GenBank Accession No. for the amino acid sequence of an exemplary AMPAR subunit 2 is NP_001077089. The GenBank Accession No. for the amino acid sequence of an exemplary KAR-GluR6 subunit is CAC67487. The GenBank Accession No. for the amino acid sequence of an exemplary KAR 2a subunit is CAC80547. The GenBank Accession No. for the amino acid sequence of an exemplary KAR 1 subunit is NP_055434.

Double-Stranded Ribonucleic Acid (dsRNA)

In one embodiment, the invention provides a double-stranded ribonucleic acid (dsRNA) molecule packaged in an association complex, such as a liposome, for inhibiting the expression of a gene in a cell or mammal, wherein the dsRNA comprises an antisense strand comprising a region of complementarity which is complementary to at least a part of an mRNA formed in the expression of the gene, and wherein the region of complementarity is less than 30 nucleotides in length, generally 19-24 nucleotides in length, and wherein said dsRNA, upon contact with a cell expressing said gene, inhibits the expression of said gene by at least 40%. The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of a gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc.

The dsRNAs suitable for packaging in the association complexes described herein can include a duplex structure of between 18 and 25 basepairs (e.g., 21 base pairs). In some embodiments, the dsRNAs include at least one strand that is at least 21 nt long. In other embodiments, the dsRNAs include at least one strand that is at least 15, 16, 17, 18, 19, 20, or more contiguous nucleotides.

RNA Interference

In one preferred embodiment, RNAi technology can be used to inhibit or downregulate the expression of one or more glutamate receptors by decreasing transcription of the gene encoding one or more glutamate receptors. RNA interference or "RNAi" is a term initially coined by Fire and co-workers to describe the observation that double-stranded RNA (dsRNA) can block gene expression when it is introduced into worms (Fire et al. (1998) Nature 391, 806-811). "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. See for example U.S. patent application Ser.

Nos. 20030153519A1; 20030167490A1; and U.S. Pat. Nos. 6,506,559; 6,573,099, which are herein incorporated by reference in their entirety.

Isolated RNA molecules specific to glutamate receptor (e.g. AMPAR, NMDAR, KAR) mRNA, which mediate RNAi, are antagonists useful in the method of the present invention. In one embodiment, the RNA interfering agents used in the methods of the invention, e.g., the siRNAs used in the methods of the invention, can to be taken up actively by cells ex vivo by their addition to the culture medium, illustrating efficient delivery of the RNA interfering agents, e.g., the siRNAs used in the methods of the invention.

An "RNA interfering agent" as used herein, is defined as any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), and small molecules which interfere with or inhibit expression of a target gene by RNA interference (RNAi). The target gene of the present invention is the gene encoding a glutamate receptor.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, 5, or 6 nucleotides. The length of the overhang is independent between the two strands, i.e., the length of the overhang on one strand is not dependent on the length of the overhang on the second strand. In one embodiment, the siRNA can inhibit one or more glutamate receptors by transcriptional silencing. Preferably the siRNA is capable of promoting RNA interference through degradation or specific post-transcriptional gene silencing (PTGS) of the target messenger RNA (mRNA).

To induce RNA interference in a cell, dsRNA may be introduced into the cell as an isolated nucleic acid fragment or via a transgene, plasmid or virus. Alternatively, siRNA may be synthesized and introduced directly into the cell. Other strategies for delivery of the RNA interfering agents, e.g., the siRNAs or shRNAs of used in the methods of the invention, may also be employed, such as, for example, delivery by a vector, e.g., a plasmid or viral vector, e.g., a lentiviral vector. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated be reference herein).

siRNA sequences are selected on the basis of their homology to the gene it is desired to silence. Homology between two nucleotide sequences may be determined using a variety of programs including the BLAST program, of Altschul et al. (1990) J. Mol. Biol. 215: 403-10, or BestFit, which is part of the Wisconsin Package, Version 8, September 1994, (Genetics Computer Group, 575 Science Drive, Madison, Wis., USA, Wisconsin 53711). Sequence comparisons may be made using FASTA and FASTP (see Pearson & Lipman, 1988. Methods in Enzymology 183: 63-98). Parameters are preferably set, using the default matrix, as follows: Gapopen (penalty for the first residue in a gap): −16 for nucleic acid; Gapext (penalty for additional residues in a gap): −4 for nucleic acids; KTUP word length: 6 for nucleic acids.

Sequence comparison may be made over the full length of the relevant sequence, or may more preferably be over a contiguous sequence of about or 10, 15, 20, 25 or 30 bases. Preferably the degree of homology between the siRNA and the target gene is at least 75%, at least 80%, at least 85%, at least 90%, at least 95%, at least 97%, or at least 99%.

The degree of homology between the siRNA or dsRNA and the gene to be silenced will preferably be sufficient that the siRNA or dsRNA will hybridize to the nucleic acid of the gene sequence under stringent hybridization conditions.

Typical hybridization conditions use 4-6.times.SSPE; 5-10.times. Denhards solution, 5 g polyvinylpyrrolidone and 5 g bovine serum albumin; 100 .ug-1 mg/ml sonicated salmon sperm DNA; 0.1-1% sodium dodecyl sulphate; optionally 40-60% deionized formamide. Hybridization temperature will vary depending on the GC content of the nucleic acid target sequence but will typically be between 42 .degree. C.-65 .degree. C. Sambrook et al (2001) Molecular Cloning: A Laboratory Approach (3.sup.rd Edn, Cold Spring Harbor Laboratory Press). A common formula for calculating the stringency conditions required to achieve hybridization between nucleic acid molecules of a specified homology is: Tm=81.5 C.+16.6 Log [Na+]+0.41[% G+C]−0.63(% formamide).

The siRNA may be between 10 bp and 30 bp in length, preferably between 20 bp and 25 bp. Preferably, the siRNA is 19, 20, 21 or 22 bp in length.

The siRNA sequence may be, for example, any suitable contiguous sequence of 10-30 by from the sequence corresponding to a kainate (KA) receptor, N methyl-D-aspartate (NMDA) receptor, or alpha ($\alpha$)-amino-3-hydroxy-5-methyl-4-isoxazolepropionic acid (AMPA) receptor (AMPAR).

The siRNA sequence may be, for example, any suitable contiguous sequence of 10-30 by from the sequence corresponding to the GenBank Accession No. for the amino acid sequence of an exemplary AMPAR subunit, NP_000818 (SEQ ID NO: 1).

```
      mqhifaffct gflgavvgan fpnniqiggl fpnqqsqeha afrfalsqlt eppkllpqid
  61  ivnisdsfem tyrfcsqfsk gvyaifgfye rrtvnmltsf cgalhvcfit psfpvdtsnq
 121  fvlqlrpelq dalisiidhy kwqkfvyiyd adrglsvlqk vldtaaeknw qvtavniltt
```

```
181  teegyrmlfq  dlekkkerlv  vvdceserln  ailgqiikle  kngigyhyil  anlgfmdidl
241  nkfkesganv  tgfqlvnytd  tipakimqqw  knsdardhtr  vdwkrpkyts  altydgvkvm
301  aeafqslrrq  ridisrrgna  gdclanpavp  wgqgidiqra  lqqvrfeglt  gnvqfnekgr
361  rtnytlhvie  mkhdsirkig  ywneddkfvp  aatdaqaggd  nssvqnrtyi  vttiledpyv
421  mlkknanqfe  gndryegycv  elaaeiakhv  gysyrleivs  dgkygardpd  tkawngmvge
481  lvygradvav  apltitlvre  evidfskpfm  slgisimikk  pqkskpgvfs  fldplayeiw
541  mcivfayigv  svvlflvsrf  spyewhseef  eegrdqttsd  qsnefgifns  lwfslgafmq
601  qgcdisprsl  sgrivggvww  fftliiissy  tanlaafltv  ermvspiesa  edlakqteia
661  ygtleagstk  effrrskiav  fekmwtymks  aepsvfvrtt  eegmirvrks  kgkyaylles
721  tmneyieqrk  pcdtmkvggn  ldskgygiat  pkgsalrnpv  nlavlklneq  glldklknkw
781  wydkgecgsg  ggdskdktsa  lslsnvagvf  yiligglgla  mlvaliefcy  ksrseskrmk
841  gfclipqqsi  neairtstlp  rnsgagassg  gsgengrvvs  hdfpksmqsi  pcmshssgmp
901  lgatgl
```

The siRNA sequence may be, for example, any suitable contiguous sequence of 10-30 by from the sequence corresponding to the GenBank Accession No. for the amino acid sequence of an exemplary AMPAR subunit 2 (isoform 1), NP_000817 (SEQ ID NO: 2).

```
  1  mqkimhisvl  lspvlwglif  gvssnsiqig  glfprgadqe  ysafrvgmvq  fstsefrltp
 61  hidnlevans  favtnafcsq  fsrgvyaifg  fydkksvnti  tsfcgtlhvs  fitpsfptdg
121  thpfviqmrp  dlkgallsli  eyyqwdkfay  lydsdrglst  lqavldsaae  kkwqvtainv
181  gninndkkde  myrslfqdle  lkkerrvild  cerdkvndiv  dqvitigkhv  kgyhyiianl
241  gftdgdllki  qfgganvsgf  qivdyddslv  skfierwstl  eekeypgaht  ttikytsalt
301  ydavqvmtea  frnlrkqrie  isrrgnagdc  lanpavpwgq  gveieralkq  vqveglsgni
361  kfdqngkrin  ytinimelkt  ngprkigyws  evdkmvvtlt  elpsgndtsg  lenktvvvtt
421  ilespyvmmk  knhemlegne  ryegycvdla  aeiakhcgtk  ykltivgdgk  ygardadtki
481  wngmvgelvy  gkadiaiapl  titlvreevi  dfskpfmslg  isimikkpqk  skpgvfsfld
541  playeiwmci  vfayigvsvv  lflvsrfspy  ewhteefedg  retqssestn  efgifnslwf
601  slgafmrqgc  disprslsgr  ivggvwwfft  liiissytan  laafltverm  vspiesaedl
661  skqteiaygt  ldsgstkeff  rrskiavfdk  mwtymrsaep  svfvrttaeg  varvrkskgk
721  yayllestmn  eyieqrkpcd  tmkvggnlds  kgygiatpkg  sslrtpvnla  vlklseqgvl
781  dklknkwwyd  kgecgakdsg  skektsalsl  snvagvfyil  vgglglamlv  aliefcyksr
841  aeakrmkvak  naqninpsss  qnsqnfatyk  egynvygies  vki
```

The siRNA sequence may be, for example, any suitable contiguous sequence of 10-30 by from the sequence corresponding to the GenBank Accession No. for the amino acid sequence of an exemplary KARGluR6 subunit, CAC67487 (SEQ ID NO:3).

```
  1  mkiifpilsn  pvfrrtvkll  lcllwigysq  gtthvlrfgg  ifeyvesgpm  gaeelafrfa
 61  vntinrnrtl  lpnttltydt  qkinlydsfe  askkacdqls  lgvaaifgps  hsssanavqs
121  icnalgvphi  qtrwkhqvsd  nkdsfyvsly  pdfsslsrai  ldlvqffkwk  tvtvvyddst
```

-continued

```
 181  glirlqelik apsrynlrlk irqlpadtkd akpllkemkr gkefhvifdc shemaagilk
 241  qalamgmmte yyhyifttld lfaldvepyr ysgvnmtgfr ilntentqvs siiekwsmer
 301  lqappkpdsg lldgfmttda almydavhvv svavqqfpqm tvsslqcnrh kpwrfgtrfm
 361  slikeahweg ltgritfnkt nglrtdfdld vislkeegle kigtwdpasg lnmtesqkgk
 421  panitdslsn rslivttile epyvlfkksd kplygndrfe gycidllrel stilgftyei
 481  rlvedgkyga qddangqwng mvrelidhka dlavaplait yvrekvidfs kpfmtlgisi
 541  lyrkpngtnp gvfsflnpls pdiwmyilla ylgvscvlfv iarfspyewy nphpcnpdsd
 601  vvennftlln sfwfgvgalm qqgselmpka lstrivggiw wfftliiiss ytanlaaflt
 661  vermespids addlakqtki eygavedgat mtffkkskis tydkmwafms srrqsvlvks
 721  neegiqrvlt sdyaflmest tiefvtqrnc nltqigglid skgygvgtpm gspyrdkiti
 781  ailqlqeegk lhmmkekwwr gngcpeeesk easalgvqni ggifivlaag lvlsvfvavg
 841  eflykskkna qlekessiwl vppyhpdtv
```

The siRNA sequence may be, for example, any suitable contiguous sequence of 10-30 by from the sequence corresponding to the GenBank Accession No. for the amino acid sequence of an exemplary KAR 1 subunit, NP_055434 (SEQ ID NO: 4).

```
   1  mprvsaplvl lpawlvmvac sphslriaai lddpmecsrg erlsitlakn rinraperlg
  61  kakvevdife llrdseyeta etmcqilpkg vvavlgpsss passsiisni cgekevphfk
 121  vapeefvkfq fqrfttlnlh psntdisvav agilnffnct taclicakae cllnlekllr
 181  qfliskdtls vrmlddtrdp tpllkeirdd ktatiiihan asmshtillk aaelgmvsay
 241  ytyiftnlef slqrmdslvd drvnilgfsi fnqshaffqe faqslnqswq encdhvpftg
 301  palssallfd avyavvtavq elnrsqeigv kplscgsaqi wqhgtslmny lrmvelegly
 361  ghiefnskgq rsnyalkilq ftrngfrqig qwhvaeglsm dshlyasnis dtlfnttlvv
 421  ttilenpylm lkgnhqemeg ndryegfcvd mlkelaeilr fnykirlvgd gvygvpeang
 481  twtgmvgeli arkadlavag ltitaerekv idfskpfmtl gisilyrvhm grkpgyfsfl
 541  dpfspgvwlf mllaylavsc vlflvarltp yewysphpca qgrcnllvnq yslgnslwfp
 601  vggfmqqgst iapralstrc vsgvwwaftl iiissytanl aafltvqrmd vpiesvddla
 661  dqtaieygti hggssmtffq nsryqtyqrm wnymyskqps vfvksteegi arvlnsnyaf
 721  llestmneyy rqrncnltqi gglldtkgyg igmpvgsvfr defdlailql qennrleilk
 781  rkwweggkcp keedhrakgl gmeniggifv vlicglivai fmamleflwt lrhseatevs
 841  vcqemvtelr siilcqdsih prrrraavpp prppipeerr prgtatlsng klcgagepdq
 901  laqrlaqeaa lvargcthir vcpecrrfqg lrarpspars eeslewektt nssepe
```

The siRNA sequence may be, for example, any suitable contiguous sequence of 10-30 by from the sequence corresponding to the GenBank Accession No. for the amino acid sequence of an exemplary KAR 2a subunit, NP_002079 (SEQ ID NO: 5).

```
   1  mpaellllli vafaspscqv lsslrmaail ddqtvcgrge rlalalareq ingiievpak
  61  arvevdifel qrdsqyettd tmcqilpkgv vsvlgpsssp asastvshic gekeiphikv
 121  gpeetprlqy lrfasvslyp snedvslavs rilksfnyps aslicakaec llrleelvrg
 181  flisketlsv rmlddsrdpt pllkeirddk vstiiidana sishlilrka selgmtsafy
```

```
241 kyilttmdfp ilhldgived ssnilgfsmf ntshpfypef vrslnmswre nceastylgp 301 alsaalmfda vhvvvsavre lnrsqeigvk plactsaniw phgtslmnyl rmveydgltg 361 rvefnskgqr tnytlrilek srqghreigv wysnrtlamn attldinlsq tlanktlvvt 421 tilenpyvmr rpnfqalsgn erfegfcvdm lrelaellrf ryrlrlvedg lygapepngs 481 wtgmvgelin rkadlavaaf titaerekvi dfskpfmtlg isilyrvhmg rkpgyfsfld 541 pfspavwlfm llaylavscv lflaarlspy ewynphpclr arphilenqy tlgnslwfpv 601 ggfmqqgsei mpralstrcv sgvwwaftli iissytanla afltvqrmev pvesaddlad 661 qtnieygtih agstmtffqn sryqtyqrmw nymqskqpsv fvksteegia rvlnsryafl 721 lestmneyhr rlncnltqig glldtkgygi gmplgspfrd eitlailqlq ennrleilkr 781 kwweggrcpk eedhrakglg meniggifiv licgliiavf vavmefiwst rrsaeseevs 841 vcqemlqelr havscrktsr srrrrrpggp srallslrav remrlsngkl ysagaggdag 901 sahggpqrll ddpgppsgar paaptpcthv rvcqecrriq alrasgagap prglgvpaea 961 tspprprpgp agprelaehe
```

The siRNA sequence may be, for example, any suitable contiguous sequence of 10-30 by from the sequence corresponding to the GenBank Accession No. for the amino acid sequence of an exemplary GluR3 subunit, NP_000831 (SEQ ID NO: 6).

```
  1 mkmltrlqvl tlalfskgfl lslgdhnflr reikiegdlv lgglfpinek gtgteecgri 61 nedrgiqrle amlfaidein kddyllpgvk lgvhildtcs rdtyaleqsl efvrasltkv 121 deaeymcpdg syaiqenipl liagviggsy ssvsiqvanl lrlfqipqis yastsaklsd 181 ksrydyfart vppdfyqaka maeilrffnw tyvstvaseg dygetgieaf eqearlrnic 241 iataekvgrs nirksydsvi rellqkpnar vvvlfmrsdd sreliaaasr anasftwvas 301 dgwgaqesii kgsehvayga itlelasqpv rqfdryfqsl npynnhrnpw frdfweqkfq 361 cslqnkrnhr rvcdkhlaid ssnyeqeski mfvvnavyam ahalhkmqrt lcpnttklcd 421 amkildgkkl ykdyllkinf tapfnpnkda dsivkfdtfg dgmgrynvfn fqnvggkysy 481 lkvghwaetl sldvnsihws rnsvptsqcs dpcapnemkn mqpgdvccwi cipcepyeyl 541 adeftcmdcg sgqwptadlt gcydlpedyi rwedawaigp vtiaclgfmc tcmvvtvfik 601 hnntplvkas grelcyillf gvglsycmtf ffiakpspvi calrrlglgs sfaicysall 661 tktnciarif dgvkngaqrp kfispssqvf iclglilvqi vmvsvwlile apgtrrytla 721 ekretvilkc nvkdssmlis itydvilvil ctvyafktrk cpenfneakf igftmyttci 781 iwlaflpify vtssdyrvqt ttmcisvsls gfvvlgclfa pkvhiilfqp qknvvthrlh 841 lnrfsvsgtg ttysqssast yvptvcngre vldsttssl
```

The siRNA sequence may be, for example, any suitable contiguous sequence of 10-30 by from the sequence corresponding to the GenBank Accession No. for the amino acid sequence of an exemplary GluR4 subunit, NP_000820 (SEQ ID NO: 7).

```
  1 mriisrqivl lfsgfwglam gafpssvqig glfirntdqe ytafrlaifl hntspnasea 61 pfnlvphvdn ietansfavt nafcsqysrg vfaifglydk rsvhtltsfc salhislitp 121 sfptegesqf vlqlrpslrg allslldhye wncfvflydt drgysilqai mekagqngwh
```

-continued

```
181 vsaicvenfn dvsyrqllee ldrrqekkfv idceierlqn ileqivsvgk hvkgyhyiia
241 nlgfkdisle rfihgganvt gfqlvdfntp mviklmdrwk kldqreypgs etppkytsal
301 tydgvlvmae tfrslrrqki disrrgnagd clanpaapwg qgidmertlk qvriqgltgn
361 vqfdhygrrv nytmdvfelk stgprkvgyw ndmdklvliq dvptlgndta aienrtvvvt
421 timespyvmy kknhemfegn dkyegycvdl aseiakhigi kykiaivpdg kygardadtk
481 iwngmvgelv ygkaeiaiap ltitlvreev idfskpfmsl gisimikkpq kskpgvfsfl
541 dplayeiwmc ivfayigvsv vlflvsrfsp yewhteeped gkegpsdqpp nefgifnslw
601 fslgafmqqg cdisprslsg rivggvwwff tliiissyta nlaafltver mvspiesaed
661 lakqteiayg tldsgstkef frrskiavye kmwtymrsae psvftrttae gvarvrkskg
721 kfafllestm neyieqrkpc dtmkvggnld skgygvatpk gsslgtpvnl avlklseagv
781 ldklknkwwy dkgecgpkds gskdktsals lsnvagvfyi lvgglglaml valiefcyks
841 raeakrmklt fseairnkar lsitgsvgen grvltpdcpk avhtgtairq ssglaviasd
901 lp
```

The siRNA sequence may be, for example, any suitable contiguous sequence of 10-30 by from the sequence corresponding to the GenBank Accession No. for the amino acid sequence of an exemplary GluR5 subunit, NP_000821 (SEQ ID NO: 8).

```
  1 mehgtllaqp glwtrdtswa llyflcyilp qtapqvlrig gifetvenep vnveelafkf
 61 avtsinrnrt lmpnttltyd iqrinlfdsf easrracdql algvaalfgp shsssvsavq
121 sicnalevph iqtrwkhpsv dnkdlfyinl ypdyaaisra ildlvlyynw ktvtvvyeds
181 tglirlqeli kapsryniki kirqlpsgnk dakpllkemk kgkefyvifd cshetaaeil
241 kqilfmgmmt eyyhyffttl dlfaldlely rysgvnmtgf rllnidnphv ssiiekwsme
301 rlqapprpet glldgmmtte aalmydavym vaiashrasq ltvsslqchr hkpwrlgprf
361 mnlikearwd gltghitfnk tnglrkdfdl diislkeegt ekaagevskh lykvwkkigi
421 wnsnsglnmt dsnkdkssni tdslanrtli vttileepyv myrksdkply gndrfegycl
481 dllkelsnil gfiydvklvp dgkygaqndk gewngmvkel idhradlava pltityvrek
541 vidfskpfmt lgisilyrkp ngtnpgvfsf lnplspdiwm yvllaclgvs cvlfviarft
601 pyewynphpc npdsdvvenn ftllnsfwfg vgalmqqgse lmpkalstri vggiwwfftl
661 iiissytanl aafltverme spidsaddla kqtkieygav rdgstmtffk kskistyekm
721 wafmssrqqt alvrnsdegi qrvlttdyal lmestsieyv tqrncnltqi gglidskgyg
781 vgtpigspyr dkitiailql qeegklhmmk ekwwrgngcp eednkeasal gveniggifi
841 vlaaglvlsv fvaigefiyk srknndieqa fcffyglqck qthptnstsg ttlstdlecg
901 klireergir kqssvhtv
```

The siRNA sequence may be, for example, any suitable contiguous sequence of 10-30 by from the sequence corresponding to The GenBank Accession No. for the amino acid sequence of an exemplary GluR6 subunit, NP_068775 (SEQ ID NO: 9).

```
  1 mkiifpilsn pvfrrtvkll lcllwigysq gtthvlrfgg ifeyvesgpm gaeelafrfa
 61 vntinrnrtl lpnttltydt qkinlydsfe askkacdqls lgvaaifgps hsssanavqs
121 icnalgvphi qtrwkhqvsd nkdsfyvsly pdfsslsrai ldlvqffkwk tvtvvyddst
```

```
181  glirlqelik  apsrynlrlk  irqlpadtkd  akpllkemkr  gkethvifdc  shemaagilk
241  qalamgmmte  yyhyifttld  lfaldvepyr  ysgvnmtgfr  ilntentqvs  siiekwsmer
301  lqappkpdsg  lldgtmttda  almydavhvv  svavqqfpqm  tvsslqcnrh  kpwrfgtrfm
361  slikeahweg  ltgritfnkt  nglrtdfdld  vislkeegle  kigtwdpasg  lnmtesqkgk
421  panitdslsn  rslivttile  epyvlfkksd  kplygndrfe  gycidllrel  stilgftyei
481  rlvedgkyga  qddangqwng  mvrelidhka  dlavaplait  yvrekvidfs  kpfmtlgisi
541  lyrkpngtnp  gvfsflnpls  pdiwmyilla  ylgvscvlfv  iarfspyewy  nphpcnpdsd
601  vvennftlln  sfwfgvgalm  qqgselmpka  lstrivggiw  wfftliiiss  ytanlaaflt
661  vermespids  addlakqtki  eygavedgat  mtffkkskis  tydkmwafms  srrqsvlvks
721  neegiqrvlt  sdyaflmest  tiefvtqrnc  nltqigglid  skgygvgtpm  gspyrdkiti
781  ailqlqeegk  lhmmkekwwr  gngcpeeesk  easalgvqni  ggifivlaag  lvlsvfvavg
841  eflykskkna  qlekrsfcsa  mveelrmslk  cqrrlkhkpq  apvivkteev  inmhtfndrr
901  lpgketma
```

The siRNA sequence may be, for example, any suitable contiguous sequence of 10-30 by from the sequence corresponding to the GenBank Accession No. for the amino acid sequence of an exemplary GluR7 subunit, NP_1000822 (SEQ ID NO: 10).

```
  1  mtapwrrlrs  lvweywagll  vcafwipdsr  gmphvirigg  ifeyadgpna  qvmnaeehaf
 61  rfsaniinrn  rtllpnttlt  ydiqrihfhd  sfeatkkacd  qlalgvvaif  gpsqgsctna
121  vqsicnalev  phiqlrwkhh  pldnkdtfyv  nlypdyasls  haildlvqyl  kwrsatvvyd
181  dstglirlqe  limapsryni  rlkirqlpid  sddsrpllke  mkrgrefrii  fdcshtmaaq
241  ilkqamamgm  mteyyhfift  tldlyaldie  pyrysgvnlt  gfrilnvdnp  hvsaivekws
301  merlqaaprs  esglldgvmm  tdaallydav  hivsvcyqra  pqmtvnslqc  hrhkawrfgg
361  rfmnfikeaq  wegltgrivf  nktsglrtdf  dldiislked  glekvgvwsp  adglniteva
421  kgrgpnvtds  ltnrslivtt  vleepfvmfr  ksdrtlygnd  rfegycidll  kelahilgfs
481  yeirlvedgk  ygaqddkgqw  ngmvkelidh  kadlavaplt  ithvrekaid  fskpfmtlgv
541  silyrkpngt  npsvfsflnp  lspdiwmyvl  laylgvscvl  fviarfspye  wydahpcnpg
601  sevvennftl  lnsfwfgmgs  lmqqgselmp  kalstriigg  iwwfftliii  ssytanlaaf
661  ltvermespi  dsaddlakqt  kieygavkdg  atmtffkksk  istfekmwaf  msskpsalvk
721  nneegiqral  tadyallmes  ttieyvtqrn  cnltqiggli  dskgygigtp  mgspyrdkit
781  iailqlqeed  klhimkekww  rgsgcpeeen  keasalgiqk  iggifivlaa  glvlsvlvav
841  gefvyklrkt  aereqrsfcs  tvadeirfsl  tcqrrvkhkp  qppmmvktda  vinmhtfndr
901  rlpgkdsmac  stslapvfp
```

In some embodiments, the siRNA has an overhang at one or both ends of one or more deoxythymidine bases. The overhang is not to be interpreted as part of the siRNA sequence. Where present, it serves to increase the stability of the siRNA within cells by reducing its susceptibility to degradation by nucleases.

siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR12; P(O)R; P(O)OR6; CO; or CONR'2 wherein R is H (or a salt) or alkyl (1-12 C) and R6 is alkyl (1-9 C) is joined to adjacent nucleotides through —O— or —S—.

Alternatively, siRNA molecules or longer dsRNA molecules may be made recombinantly by transcription of a nucleic acid sequence, preferably contained within a vector as described below.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl)uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5-methoxyuracil, 2 methylthio-N6-isopentenyladenine, uracil-5-oxyacetic acid methyl ester, psueouracil, 2-thiocytosine, 5-methyl-2 thiouracil, 2-thiouracil, 4-thiouracil, 5-methyluracil, N-uracil-5-oxyacetic acid methylester, uracil 5-oxyacetic acid, queosine, 2-thiocytosine, 5-propyluracil, 5-propylcytosine, 5-ethyluracil, 5-ethylcytosine, 5-butyluracil, 5-pentyluracil, 5-pentylcytosine, and 2,6,diaminopurine, methylpsuedouracil, 1-methylguanine, 1-methylcytosine.

Ribozymes

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules includes one or more sequences complementary to the target gene mRNA, and includes the well known catalytic sequence responsible for mRNA cleavage disclosed, for example, in U.S. Pat. No. 5,093,246. Within the scope of this disclosure are engineered hammerhead motif ribozyme molecules that specifically and efficiently catalyze endonucleolytic cleavage of RNA sequences encoding target gene proteins, e.g. glutamate receptors. Specific ribozyme cleavage sites within any potential RNA target are initially identified by scanning the molecule of interest for ribozyme cleavage sites that include the sequences GUA, GUU, and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

The antisense, ribozyme, and/or triple helix molecules described herein may reduce or inhibit the transcription (triple helix) and/or translation (antisense, ribozyme) of mRNA produced by both normal and mutant target gene alleles.

Aptamer-Type Oligonucleotide Agents

An oligonucleotide agent featured in the invention can be an aptamer. An aptamer binds to a non-nucleic acid ligand, such as a small organic molecule or protein, e.g., a transcription or translation factor, and subsequently modifies (e.g., inhibits) activity. An aptamer can fold into a specific structure that directs the recognition of the targeted binding site on the non-nucleic acid ligand. An aptamer can contain any of the modifications described herein.

In one embodiment, an aptamer includes a modification that improves targeting, e.g. a targeting modification described herein.

The term "aptamer" refers to a nucleic acid or oligonucleotide molecule that binds to a specific molecular target such as a protein receptor. Aptamers are obtained from an in vitro evolutionary process known as SELEX (Systematic Evolution of Ligands by EXponential Enrichment), which selects target-specific aptamer sequences from large combinatorial libraries of single stranded oligonucleotide templates comprising randomized sequences. Aptamer compositions may be double-stranded or single-stranded, and may include deoxyribonucleotides, ribonucleotides, nucleotide derivatives, or other nucleotide-like molecules. The nucleotide components of an aptamer may include modified or non-natural nucleotides, for example nucleotides that have modified sugar groups (e.g., the 2'-OH group of a ribonucleotide may be replaced by 2'-F or 2'-NH$_2$) which may improve a desired property, e.g., resistance to nucleases or longer lifetime in blood.

In a preparation of nucleic acids of the invention, individual aptamers having the same nucleotide sequence may differ in their secondary structure. Aptamers may also be conjugated to other molecules, e.g., a high molecular weight carrier to slow clearance of the aptamer from the circulatory system. Aptamers may be specifically cross-linked to their cognate ligands, e.g., by photo-activation of a cross-linker. [Brody, E. N. and L. Gold (2000) J. Biotechnol. 74:5-13.].

US Patent Application 20060148746, incorporated by reference in its entirety herein, describes the identification of nucleic acid inhibitors of glutamate receptors. Accordingly, in certain aspects invention relates to methods of identifying a nucleic acid ligand(s) that can inhibit glutamate receptor function, the method comprising the steps of screening a nucleic acid library for a nucleic acid that binds to a glutamate receptor; providing a cell that has been transfected to overexpress the glutamate receptor; exposing the cell to glutamate in the presence and absence of the nucleic acid identified by the method and measuring the glutamate-induced whole-cell current using laser pulse photolysis of caged glutamate as a source of glutamate. The measurements for whole-cell current in the absence and presence of the nucleic acid are compared. A decrease in whole-cell current in the presence of the nucleic acid indicates that the nucleic acid is a specific glutamate receptor inhibitor. The SELEX method can be used, in preferred embodiments, to screen the library and identify the nucleic acid.

The chemical modifications described above for miRNAs and antisense RNAs, and described elsewhere herein, are also appropriate for use in decoy nucleic acids.

Vectors

The invention also provides vectors comprising a nucleotide sequence encoding an siRNA or longer RNA or DNA sequence for production of dsRNA. The vector may be any RNA or DNA vector. The vector is preferably an expression vector, wherein the nucleotide sequence is operably linked to a promoter compatible with the cell. The vector will preferably have at least two promoters, one to direct expression of the sense strand and one to direct expression of the antisense strand of the dsRNA. Alternatively, two vectors may be used, one for the sense strand and one for the antisense strand. Alternatively the vector may encode RNAs which form stem-loop structures which are subsequently cleaved by the cell to produce dsRNA.

Where the vector is an expression vector, the sequence to be expressed will preferably be operably linked to a promoter functional in the target cells. Promoters suitable for use in various vertebrate systems are well known. For example, suitable promoters include viral promoters such as mammalian retrovirus or DNA virus promoters, e.g. MLV, CMV, RSV, SV40 IEP and adenovirus promoters and metallothionein promoter. The CMV IEP may be more preferable for human use. Strong mammalian promoters may also be suitable as well as RNA polymerase II and III promoters. Variants of such promoters retaining substantially similar transcriptional activities may also be used.

Other vehicles suitable for use in delivering nucleic acids such as siRNAs include viruses and virus-like particles (VLPs) such as HPV VLPs comprising the L1 and/or L2 HPV viral protein; or hepatitis B viral proteins. Other suitable VLPs may be derived from picornaviruses; togaviruses; rhabdoviruses; orthomyxoviruses; retroviruses; hepadnaviruses; papovaviruses; adenoviruses; herpesviruses; and pox viruses.

The RNA interfering agents, e.g., the siRNAs or shRNAs of the invention, may be introduced along with components that perform one or more of the following activities: enhance uptake of the RNA interfering agents, inhibit annealing of single strands, stabilize single strands, or otherwise facilitate delivery to the target cell and increase inhibition of the target gene, e.g. one or more glutamate receptors (AMPAR, NMDAR, KAR).

Delivery

Various agents may be used to improve the delivery of RNA, DNA or protein into the cell. Viral vectors as described above may be used to deliver nucleic acid into a cell. Where other vectors, or no vector, are used, delivery agents such as liposomes may usefully be employed. Delivery peptides such as Antennapedia of the HIV TAT peptide may be used, as may organic polymers such as a dendrimers or polylysine-transferrine-conjugates.

Liposomes can be prepared from a variety of cationic lipids, including DOTAP, DOTMA, DDAB, L-PE, and the like. Lipid carrier mixtures containing a cationic lipid, such as N-[1-(2,3-dioleyloxy)propyl]-N,N,N-triethylammonium chloride (DOTMA) also known as "lipofectin", dimethyl dioctadecyl ammonium bromide (DDAB), 1,2-dioleoyloxy-3-(trimethylammonio)propane (DOTAP) or L-lysinyl-phosphatidylethanolamine (L-PE) and a second lipid, such as dioleoylphosphatidylethanolamine (DOPE) or cholesterol (Chol), are particularly useful for use with nucleic acids. DOTMA synthesis is described in Feigner, et al., (1987) Proc. Nat. Acad. Sciences, (USA) 84:7413-7417. DOTAP synthesis is described in Stamatatos, et al., Biochemistry, (1988) 27:3917-3925.

Liposomes are commercially available from many sources. DOTMA:DOPE lipid carriers can be purchased from, for example, BRL. DOTAP:DOPE lipid carriers can be purchased from Boehringer Mannheim. Cholesterol and DDAB are commercially available from Sigma Corporation. DOPE is commercially available from Avanti Polar Lipids. DDAB:DOPE can be purchased from Promega. Invitrogen make liposomes under the names OLIGOFECTAMINE and LIPOFECTAMINE.

To incorporate nucleic acid into liposomes, the liposome-nucleic acid complex is prepared by mixing with the nucleic acid in an appropriate nucleic acid:lipid ratio (for example 5:3) in a physiologically acceptable diluent (for example OPTI-MEM at an appropriate dilution) immediately prior to use.

Another delivery system for polynucleotides is a colloidal dispersion system. Colloidal dispersion systems include macromolecular complexes, nanocapsules, microspheres, beads, and lipid-based systems including oil-in-water emulsions, micelles, mixed micelles and liposomes. A preferred colloidal delivery system is a liposome, an artificial membrane vesicle useful as in vivo or in vitro delivery vehicles. The composition of a liposome is usually a combination of phospholipids, usually in combination with steroids, particularly cholesterol.

Identifying Compounds

In certain aspects the invention features methods of identifying compounds that delays or inhibits platelet activation. Methods for identifying compounds comprise contacting a cell that expresses a glutamate receptor with a candidate compound, and comparing the biological activity of the glutamate receptor in the cell contacted by the candidate compound with the level of biological activity in a control cell not contacted by the candidate compound, wherein an alteration in the biological activity of the glutamate receptor identifies the candidate compound as a candidate compound that delays or inhibits platelet activation.

In certain preferred embodiments, the alteration is an inhibition of glutamate receptor activity that identifies the candidate compound as a candidate compound that delays or inhibits platelet activation.

In other certain aspects the invention features methods of identifying compounds that delays or inhibit a thrombotic disease or disorder. The methods comprise contacting a cell that expresses a glutamate receptor with a candidate compound, and comparing the biological activity of the glutamate receptor in the cell contacted by the candidate compound with the level of biological activity in a control cell not contacted by the candidate compound, wherein an alteration in the biological activity of the glutamate receptor identifies the candidate compound as a candidate compound that delays or inhibits a thrombotic disease.

In certain preferred embodiments, the alteration is an inhibition of glutamate receptor activity that identifies the candidate compound as a candidate compound that delays or inhibits a thrombotic disease. In certain preferred embodiments of the invention, the alteration of expression comprises the output measurement for glutamate receptor activity, e.g. ionotrophic receptor activity.

In the methods for identification of the compounds as described, the glutamate receptor is selected from an ionotrophic glutamate receptor or a metabotropic glutamate receptor. The ionotrophic glutamate receptor is selected from the group consisting of AMPAR, NMDAR, and KAR. The AMPAR may comprise at least one subunit selected from the group consisting of GluR1, GluR2, GluR3 and GluR4. The KAR may comprise at least one subunit selected from the group consisting of GluR 5, GluR6, GluR7, KA1 and KA2.

The cells used in the assay may be any non-neuronal cell type, although in certain preferred examples, the cell is selected from platelets, endothelial cells, sub-endothelial cells, leukocytes and megakaryocytes. The cell can be in vitro or in vivo. The cell can be a human cell.

In the methods of identifying compounds as described herein the alteration in expression is assayed using an immunological assay, an enzymatic assay, a radioimmunoassay, measurement of platelet adhesion, measurement of platelet aggregation, or measurement of platelet activation.

In certain preferred embodiments, ion channel activity can be measured using an indicator dyes and a plate reader. Indicator dyes are well known to those in the art, for example, Ca(2+) or Na(+) can be used as indicator dyes. Plate readers, such as FLIPR (Fluorometric Imaging Plate Reader) as suitable for measuring ion channel activity.

The FLIPR consists of an incubated cabinet with integrated 96-channel pipettor and fluorometer. An argon laser is used to excite fluorophores in a 96-well microtiter plate and the emitted fluorometer. An argon laser is used to excite fluorophores in a 96-well microtiter plate and the emitted fluorescence is imaged by a cooled CCD camera. The image data is downloaded from the camera and processed to average the signal form each well of the microtiter pate for each time point. The data is presented in real time on the computer screen, facilitating interpretation and trouble-shooting. In addition to fluorescence, the camera can also detect luminescence form firefly luciferase. In certain embodiments, Fluorometric Imaging Plate Reader (FLIPR) is especially suitable for high throughput screening.

The examples as described herein set forth ion flux assays and platelet activation-based assays.

Screening assays need not be performed in platelets/megakaryocytes or even non-neuronal cells. For example, the screens can do the screen in primary neurons or AMPAR or KAR transfected cells, then confirm activity in platelets/animals; also could do a binding assay to determine is a likely AMPAR or KAR, then confirm activity in platelets/animals)

In other particular embodiments, the screening assay could look at G-protein coupled receptor (GPCR) activity, which changes in response to platelet activation. Assays for determining GPCR activity are well known and routinely performed by those of skill in the art.

In any of the methods of identification as described above, one of skill in the art will easily understand that it is possible to identify modulators of glutamate receptor activation using the same methodology, wherein an alteration in the biological activity of the glutamate receptor identifies the candidate compound as a candidate compound that activates the glutamate receptor, and the alteration is a positive alteration.

Antibodies

Exemplary agents that that delays or inhibits platelet activation, that modulate glutamate receptor activity include antibodies that bind to (e.g., inhibit the activity of) glutamate receptors (e.g. ionotrophic receptors, in certain embodiments, AMPAR, KAR). In one embodiment, the antibody inhibits the interaction between the protein and its binding partner (e.g., a receptor and its substrate), e.g., by physically blocking the interaction, decreasing the affinity of the protein for its binding partner, disrupting or destabilizing protein complexes, sequestering the protein, or targeting the protein for degradation. In one embodiment, the antibody can bind to the protein at one or more amino acid residues that participate in the binding interface between the protein and its binding partner. Such amino acid residues can be identified, e.g., by alanine scanning.

In another embodiment, the antibody can bind to residues that do not participate in the binding. For example, the antibody can alter a conformation of the protein and thereby reduce binding affinity, or the antibody may sterically hinder binding. In other embodiments, the antibody can increase the activity (e.g., act as an agonist) of an agent that promotes glutamate receptor activity.

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')2 fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A., et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two b-sheets formed of about seven b-strands, and a conserved disulphide bond (see, e.g., A. F. Williams and A. N. Barclay (1988) Ann. Rev Immunol. 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two, or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with a target protein, e.g., a glutamate receptor, in certain embodiments an ionotropic glutamate receptor, in other certain embodiments an AMPAR or KAR, and in more specific embodiments a GluR1, GluR2, GluR3, GluR4 subunit of the AMPAR.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Antibody Generation

Antibodies that bind to a target protein as described herein can be generated by a variety of means, including immunization, e.g., using an animal, or in vitro methods such as phage display. All or part of the target protein can be used as an immunogen or as a target for selection. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nat. Gen. 7:13-21; U.S. 2003-0070185; U.S. Pat. No. 5,789,650; and PCT Application WO 96/34096.

Non-human antibodies to the target proteins can also be produced, e.g., in a rodent. The non-human antibody can be humanized, e.g., as described in EP 239 400; U.S. Pat. Nos. 6,602,503; 5,693,761; and 6,407,213, deimmunized, or otherwise modified to make it effectively human.

EP 239 400 (Winter et al.) describes altering antibodies by substitution (within a given variable region) of their complementarity determining regions (CDRs) for one species with those from another. Typically, CDRs of a non-human (e.g., murine) antibody are substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody.

Other methods for humanizing antibodies can also be used. For example, other methods can account for the three dimensional structure of the antibody, framework positions that are in three dimensional proximity to binding determinants, and immunogenic peptide sequences. See, e.g., PCT Application WO 90/07861; U.S. Pat. Nos. 5,693,762; 5,693,761; 5,585,089; and 5,530,101; Tempest et al. (1991) Biotechnology 9:266-271 and U.S. Pat. No. 6,407,213. Still another method is termed "humaneering" and is described, for example, in U.S. 2005-008625.

Fully human monoclonal antibodies that bind to target proteins can be produced, e.g., using in vitro-primed human splenocytes, as described by Boerner et al. (1991) J. Immunol. 147:86-95. They may be prepared by repertoire cloning as described by Persson et al. (1991) Proc. Nat. Acad. Sci. USA 88:2432-2436 or by Huang and Stollar (1991) J. Immunol. Methods 141:227-236; also U.S. Pat. No. 5,798,230. Large non-immunized human phage display libraries may also be used to isolate high affinity antibodies that can be developed as human therapeutics using standard phage technology (see, e.g., Hoogenboom et al. (1998) Immunotechnology 4:1-20; Hoogenboom et al. (2000) Immunol Today 2:371-378; and U.S. 2003-0232333).

Antibody and Protein Production

Antibodies and other proteins described herein can be produced in prokaryotic and eukaryotic cells. In one embodiment, the antibodies (e.g., scFv's) are expressed in a yeast cell such as *Pichia* (see, e.g., Powers et al. (2001) J. Immunol. Methods 251:123-35), *Hanseula*, or *Saccharomyces*.

Antibodies, particularly full length antibodies, e.g., IgG's, can be produced in mammalian cells. Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr-host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector can also carry a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies (and Fc fusions) may also include modifications, e.g., modifications that alter Fc function, e.g., to decrease or remove interaction with an Fc receptor or with Clq, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some proteins that include an Fc domain, the antibody/protein production system may be designed to synthesize antibodies or other proteins in which the Fc region is glycosylated. For example, the Fc domain of IgG molecules is glycosylated at asparagine 297 in the CH2 domain. The Fc domain can also include other eukaryotic post-translational modifications. In other cases, the protein is produced in a form that is not glycosylated.

Antibodies and other proteins can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody or Fc fusion protein. The protein can be purified from the milk, or for some applications, used directly.

Methods described in the context of antibodies can be adapted to other proteins, e.g., Fc fusions and soluble receptor fragments.

IV. Pharmaceutical Compositions
Combinations

In certain aspects, the invention features pharmaceutical compositions including a combination of an effective amount of a compound that inhibits the activity of one or more glutamate receptors and a second agent.

In certain embodiments of the invention, the compound of the invention, e.g. a compound that delays or inhibits the activity of one or more glutamate receptors, a compound that delays or inhibits platelet activity, a compound that delays or inhibits a thrombotic disease or disorder, or a compound that activates the activity of one or more glutamate receptors, may be administered in combination with an additional agent.

In certain examples, the additional agent may preferably be a compound that inhibits the activity of a second glutamate receptor. For example, if the first compound inhibits the AMPA receptor, the second compound may inhibit the KA receptor. Alternatively, the first compound may be one particular inhibitor of the AMPA receptor, and the second compound may be another particular inhibitor of the AMPA receptor.

The additional agent that inhibits the activity of a second glutamate receptor may be in certain preferred embodiments a commercially available inhibitor of a glutamate receptor, as set forth herein. The additional agent that inhibits the activity of a second glutamate receptor may be a newly synthesized inhibitor of a glutamate receptor, as set forth herein.

Combinations with Therapeutic Agents

The compound of the invention, e.g. a compound that inhibits the activity of one or more glutamate receptors, a compound that delays or inhibits platelet activity, a compound that delays or inhibits a thrombotic disease or disorder, or a compound that activates the activity of one or more glutamate receptors, may be administered in combination with a therapeutic agent.

The therapeutic agent can be any therapy that is envisioned by the skilled practicioner to be of use in the methods of the invention.

In certain preferred examples, the therapeutic agent is selected from, but not limited to, anticoagulants, antiplatelet drugs, thrombolytic agents, steroids, hormones, antibiotics, and antiinflammatories.

Anticoagulants help prevent the clotting (or coagulation) of blood. Anticoagulants prevent new clots from forming or an existing clot from enlarging. Anticoagulants do not dissolve an existing blood clot. Anticoagulants may be given to subjects that are at risk for forming blood clots, for example, but not limited to, subjects with artificial heart valves or subjects suffering from atrial fibrillation. A common type of stroke is caused by a blood clot blocking blood flow to the brain. To prevent such clots, anticoagulants are often prescribed in subjects with conditions such as atrial fibrillation to prevent a first or recurrent stroke. Examples of anticoagulants include, but are not limited to, coumarin, heparin, warfarin, direct thrombin inhibitors including lepirudin, argatroban, bivalirudin, melagatran and ximelagatran, factor Xa inhibitors including fondaparinux. A 2006 review by K. Bauer (Hematology 2006 (1): 450) describes new anticoagulants that target a single coagulation factor, including direct thrombin inhibitors and factor Xa inhibitors.

Antiplatelet agents are drugs that interfere with the blood's ability to clot. Antiplatelet agents are used to prevent blood clots from forming that can lead to heart attack or stroke. Antiplatelet agents work by preventing the platelets in the blood from clumping. Aspirin, an irreversible inhibitor of platelet cyclooxygenase activity, remains the standard against which other drugs are judged. Clinically employed anti-platelet and anti-thrombotic agents include heparin, aspirin, integrilin, and anti-GP IIb/IIIa antibodies (c7E3 Fab, abciximab, or ReoPro). Drugs that appear to be at least as efficacious as aspirin in specific clinical settings include the thienopyridines ticlopidine and clopidogrel, specific inhibitors of ADP-stimulated platelet function, and the phosphodiesterase 3 inhibitor cilostazol.

In general, drugs that can lower platelet counts include, but are not limited to, platelet inhibitors, chemotherapy drugs, chloramphenicol, colchicine, H2 blocking agents, heparin, hydralazine, indomethacin, isoniazid, quinidine, streptomycin, sulfonamide, thiazide diuretic, and tolbutamide.

Platelet activators include collagen, thrombin, ADP and epinephrine. Collagen becomes exposed to blood flow after vessel injury, and is quite a strong activator of platelets. The GP IIb/IIIa receptor is the final common endpoint of all of these activators, and enables platelets to bind to each other. Thus, in the design of platelet activators, any of these molecules is a suitable target.

Thrombolytic agents are drugs that are able to dissolve a clot (or thrombus) and reopen an artery or vein. Thrombolytic agents may be used to treat, for example, a heart attack, stroke, deep vein thrombosis (clot in a deep leg vein), pulmonary embolism, and occlusion of a peripheral artery or indwelling catheter. Thrombolytic agents are serine proteases. Accordingly, thrombolytic agents convert plasminogen to plasmin, which breaks down the fibrinogen and fibrin and dissolves the clot. Currently available thrombolyic agents include reteplase (r-PA or Retavase), alteplase (t-PA or Activase), urokinase (Abbokinase), prourokinase, anisoylated purified streptokinase activator complex (APSAC), and streptokinase.

The compounds of the invention may be administered in combination with chemotherapeutic agents. Examples of chemotherapeutic agents that may be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol,aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

Combinations with Imaging Agents

The compound of the invention, e.g. a compound that inhibits the activity of one or more glutamate receptors, a compound that delays or inhibits platelet activity, a compound that delays or inhibits a thrombotic disease or disorder, or a compound that activates the activity of one or more glutamate receptors, may be administered in combination with an imaging agent.

Platelet activation and resulting aggregation has been shown to be associated with various pathophysiological conditions including cardiovascular and cerebrovascular thromboembolic disorders such as unstable angina, myocardial infarction, transient ischemic attack, stroke, atherosclerosis and diabetes. Platelet activation and aggregation is also thought to play a significant role in venous thromboembolic disorders such as venous thrombophlebitis and subsequent pulmonary emboli. It is also known that patients whose blood flows over artificial surfaces, such as prosthetic synthetic cardiac valves, are at risk for the development of platelet plugs, thrombi and emboli. A method for the non-invasive diagnosis and monitoring of patients with such potential thromboembolic disorders would be useful in diagnosis and therapy.

Thus, in certain cases, it may be advantageous to administer the compounds of the invention along with an imaging agent in order to detect a thrombosis, to diagnose a disease state or to determine prognosis or course of treatment.

In certain cases, the imaging agent is a radiolabeled compound. By "radiolabeled", it is meant that the subject compound contains a radioisotope which is suitable for administration to a mammalian patient.

In certain embodiments of the invention, the compounds of the invention, e.g. the inhibitors of the glutamate receptors, are radiolabeled.

The radiolabeled compounds of the invention are useful with both newly formed and older thrombi.

Suitable radioisotopes are known to those skilled in the art and include, for example, isotopes of halogens (such as chlorine, fluorine, bromine and iodine), and metals including technetium and indium. Preferred radioisotopes include 11C, 18F, $^{123}$I, $^{125}$I, $^{131}$I, $^{99}$m Tc, $^{94}$m Tc, $^{95}$m Tc, $.^{111}$In, $^{62}$Cu, $^{43}$Sc, $.^{45}$Ti, $._{67}$Ga, $.^{68}$Ga, $.^{97}$Ru, $.^{72}$As, $..^{82}$Rb, and $.^{201}$Tl. Most preferred are the isoptopes $.^{123}$I, $.^{111}$In, and $^{99}$m Tc. Radiolabeled compounds of the invention may be prepared using standard radiolabeling procedures well known to those skilled in the art. Suitable synthesis methodology is described in detail below. As discussed below, the cyclic platelet glycoprotein IIb/IIIa compounds of the invention may be radiolabeled either directly (that is, by incorporating the radiolabel directly into the compounds) or indirectly (that is, by incorporating the radiolabel into the compounds through a chelating agent, where the chelating agent has been incorporated into the compounds). Also, the radiolabeling may be isotopic or nonisotopic. With isotopic radiolabeling, one group already present in the cyclic compounds described above is substituted with (exchanged for) the radioisotope. With nonisotopic radiolabeling, the radioisotope is added to the cyclic compounds without substituting with (exchanging for) an already existing group. Direct and indirect radiolabeled compounds, as well as isotopic and nonisotopic radiolabeled compounds are included within the phrase "radiolabeled compounds" as used in connection with the present invention. Such radiolabeling should also be reasonably stable, both chemically and metabolically, applying recognized standards in the art. Also, although the compounds of the invention may be labeled in a variety of fashions with a variety of different radioisotopes, as those skilled in the art will recognize, such radiolabeling should be carried out in a manner such that the high binding affinity and specificity of the unlabeled cyclic platelet GPIIb/IIIa compounds of the invention to the GPIIb/IIIa receptor is not significantly affected. By not significantly affected, it is meant that the binding affinity and specificity is not affected more than about 3 log units, preferably not more than about 2 log units, more preferably not more than about 1 log unit, even more preferably not more than about 500%, and still even more preferably not more than about 250%, and most preferably the binding affinity and specificity is not affected at all.

U.S. Pat. No. 5,879,657, incorporated by reference in its entirety herein, describes radiolabeled platelet GPIIb/IIIa receptor antagonists as imaging agents for the diagnosis of thromboembolic disorders.

Combination therapy can be advantageous, e.g., because the therapeutic effect achieved with the combination can be greater than the effect achieved by either agent alone. For example, the maximum dose of a first agent may be limited due to toxicity. Thus, the therapeutic effect achieved of that first agent is likewise limited. The same could be true for a second agent when administered alone. However, if the first agent is administered in combination with the second agent (both, e.g., at their maximum doses), and the two agents have an additive or synergistic effect, the total therapeutic effect achieved by the combination will be greater than that achieved with either agent alone. Similarly, if two agents have additive or synergistic effects when administered in combination, then, to achieve a given therapeutic effect (e.g., an effect that can be achieved by one of the agents when used alone), the doses required of each agent when used in combination can be less than the dose required if either of the agents was used alone. This decreased dose of each agent could, for example, result in decreased side effects or toxicity caused by one or both of the agents because less is administered.

Upon improvement of a patient's condition, a maintenance dose of a compound, composition or combination of this disclosure may be administered, if necessary. Subsequently, the dosage or frequency of administration, or both, may be reduced, e.g., to about ½ or ¼ or less of the dosage or frequency of administration, as a function of the symptoms, to a level at which the improved condition is retained when the symptoms have been alleviated to the desired level, treatment should cease. Subjects may, however, require intermittent treatment on a long-term basis upon any recurrence of disease symptoms.

It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional agent in the composition.

The inhibitors or activators of glutamate receptor, or any of the combinations described herein, can be formulated into a pharmaceutical composition, either separately or together, for example, with one or more pharmaceutically acceptable carriers, adjuvants, or vehicles. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as a-, b-, and g-cyclodextrin, or chemically modified derivatives such as hydroxyalkylcyclodextrins, including 2- and 3-hydroxypropyl-b-cyclodextrins, or other solubilized derivatives may also be advantageously used to enhance delivery of compounds of the formulae described herein.

The pharmaceutical compositions of this invention may be administered enterally (e.g., orally), parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents that are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the inhibitors or activators of glutamate receptor, or any of the combinations described herein can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

In certain preferred embodiments, the compounds of the invention may be used as part of implantable medical devices. An example of an implantable medical device is a stent. Typically, a stent is compressed, inserted into a small vessel through a catheter, and then expanded to a larger diameter once placed in a proper location. Stents play an important role in a variety of medical procedures such as, for example, percutaneous transluminal coronary angioplasty (PTCA), a procedure used to treat heart disease by opening a coronary artery blocked by an occlusion. Stents are generally implanted in such procedures to reduce occlusion formation, inhibit thrombosis and restenosis, and maintain patency within vascular lumens. Examples of patents disclosing stents include U.S. Pat. Nos. 4,733,665; 4,800,882; and 4,886,062, incorporated by reference in their entireties herein. Stents may be used to locally deliver active agents, e.g. drugs or other medically beneficial materials. Local delivery, e.g. a drug-eluting stent, is often preferred over systemic delivery, particularly where high systemic doses are necessary to affect a particular site. US Patent Application 20070280988, incorporated by reference in its entirety herein, describes coating layers for medical devices and methods of making.

In preferred embodiments, a composition that inhibits platelet activation as described herein can be used in association with a drug eluting stent device to prevent stent thrombosis.

Also within the invention is a patch to deliver the inhibitors or activators of glutamate receptor, or any of the combinations described herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

In some cases (e.g., when dominant negative forms of any of the glutamate receptors as described herein) are used to practice the invention, these agents can be administered via gene therapy techniques (e.g., via adenoviral or adeno-associated virus delivery).

When the compositions of this invention comprise the inhibitors or activators of glutamate receptor, or any of the combinations described herein, and a second agent (e.g., a therapeutic agent, an imaging agent), both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The term "mammal" includes organisms, which include mice, rats, cows, sheep, pigs, rabbits, goats, and horses, monkeys, dogs, cats, and preferably humans.

The term "treating" or "treated" refers to administering a compound(s) described herein to a subject with the purpose to cure, heal, alleviate, relieve, alter, remedy, ameliorate, improve, or affect a disease, e.g., a thrombotic disease, a bleeding disease or disorder, the symptoms of the disease or the predisposition toward the disease.

A "therapeutically effective amount" or an amount required to achieve a "therapeutic effect" can be determined based on the effect of the administered agent(s). A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition is outweighed by the therapeutically beneficial effects.

Any of the inhibitors or activators of glutamate receptors, or any of the combinations described herein can be administered, e.g., once or twice daily, or about one to four times per week, or preferably weekly, biweekly, or monthly, e.g., for between about 1 to 10 weeks (e.g., between 2 to 8 weeks or between about 3 to 7 weeks, or for about 4, 5, or 6 weeks) or for one, two three, four, five, six, seven, eight, nine, ten, eleven, twelve, or more months (e.g., for up to 24 months). The skilled artisan will appreciate that certain factors may influence the dosage and timing required to effectively treat a subject, including but not limited to the severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments. Animal models can also be used to determine a useful dose, e.g., an initial dose or a regimen.

In addition, after an administration period described herein with a combination described herein, a maintenance dose can be administered to the subject. For example, the maintenance dose can include a lower dose of one or both of the drugs of the combination described herein, a dose of only one of the drugs described herein (e.g., at the same or at a lower dose than in the initial administration period). The maintenance dose may be administration of another combination described herein, e.g., a combination described herein but not employed in the initial administration period. For example, if a inhibitors of a glutamate receptor in combination with another agent, e.g. another therapeutic agent, is used for the initial administration period, the inhibitor of the glutamate receptor alone may be used for the maintenance dose, and vice versa. The maintenance dose can be administered, e.g., for a period of one, two three, four, five, six, seven, eight, nine, ten, eleven, twelve, or more months (e.g., for up to 24 or 36 months or longer) after termination of the initial administration period terminates.

An effective amount of the compound described above may range from about 0.01 mg/kg to about 500 mg/kg, or in preferred embodiments from about 0.001 mg/kg to about 500 mg/kg, or from about 0.0001 mg/kg to about 500 mg/kg. For example, a compound such as one or more of CNQX, NBQX, GYKI52466, GYKI53655, GYKI47261, cyclothiazide, YM90K, Zonampel (YM872), YM928, Perampanel (E2007), CP-465,022, ZK200775, Talampanel (LY300164), and Tezampanel (NGX424), LY382884, NS-102, UBP301, CX-516, CX-717, topiramate, and philanthotoxin-343, and pharmaceutically acceptable salts, prodrugs, esters, and hydrates thereof, can be administered in doses of 75, 150, 300, 600, and 900 mg/m2/day). For example, a dose of 300 mg/m2/day for 5 days for 3 weeks can be used. Preferably, a dose of 18,000 mg/m2/day for 5 days for 3 weeks can be used.

Effective doses will also vary depending on route of administration, as well as the co-administration with other agents, e.g., a second agent described herein.

V. Kits

The compounds (e.g., a compound that inhibits or activates a glutamate receptor that, in certain embodiments is provided in combination with a second agent) described herein can be provided in a kit. The kit includes (a) the compounds described herein, e.g., a composition(s) that includes a compound(s) described herein, and, optionally (b) informational material. The informational material can be descriptive, instructional, marketing or other material that relates to the methods described herein and/or the use of a compound(s) described herein for the methods described herein.

The invention features in one aspect kits or pharmaceutical systems for the use in delaying or preventing platelet activity in a subject comprising one or more glutamate receptor inhibitors and instructions for use.

The invention features in other aspects kits for the use in delaying or preventing a thrombotic disease in a subject comprising one or more glutamate receptor inhibitors and instructions for use.

The invention features in other certain aspects kits comprising an effective amount of a compound that delays or inhibits platelet activity and associated instructions for using the compound to delay or inhibit platelet activity.

The invention features in other certain aspects kits comprising an effective amount of a compound that delays or inhibits platelet activity and associated instructions for using the compound to treat or prevent a thrombotic disease or disorder.

The invention features in other aspects kits comprising an effective amount of a compound that treats or prevents a thrombotic disease or disorder in a subject and associated instructions for using the compound to treat or prevent a thrombotic disease or disorder. The kits of the invention can comprise an effective amount of a compound that treats or prevents a thrombotic disease or disorder in a subject wherein the compound inhibits the activity of one or more glutamate receptors in non-neuronal cells in a subject, thereby treating or preventing a thrombotic disease or disorder in the subject.

The informational material of the kits is not limited in its form. In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to administer a compound(s) (e.g., a compound that inhibits or activates a glutamate receptor that, in certain embodiments is provided in combination with a second agent) described herein in a suitable manner to perform the methods described herein, e.g., in a suitable dose, dosage form, or mode of administration (e.g., a dose, dosage form, or mode of administration described herein). In another embodiment, the informational material can include instructions to administer a compound(s) described herein to a suitable subject, e.g., a human, e.g., a human having or at risk for a disorder described herein, e.g., a thrombotic disease or disorder.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound(s) described herein, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound(s) described herein and the other ingredients, or for using a compound(s) described herein together with the other ingredients, e.g., instructions on combining the two agents prior to administration.

A compound(s) described herein can be provided in any form, e.g., liquid, dried or lyophilized form. It is preferred that a compound(s) described herein be substantially pure and/or sterile. When a compound(s) described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

The kit can include one or more containers for the composition containing a compound(s) described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

EXAMPLES

The present work demonstrates that activated platelets release glutamate. Moreover, the present work shows that platelets express both AMPAR and KA subunits, and that glutamate increases agonist induced platelet activation. The data presented herein demonstrates that glutamate binding to the AMPAR and KAR increases intracellular sodium concentration and depolarizes platelets, two important steps in platelet activation. In contrast, platelets treated with the AMPAR antagonist CNQX or platelets derived from GluR1 knockout mice are resistant to AMPA effects. In vivo experiments presented herein demonstrate that mice lacking GluR1 have a prolonged time to thrombosis.

Example 1

Glutamate Release during Thrombus Generation Increases Platelet Activation

Platelets store glutamate, express glutamate transporters, and release glutamate during activation, but vascular targets of glutamate have not been characterized (13, 14, 16, 24, 25, 33). To define the role of platelet derived glutamate in the vasculature, we first quantified platelet glutamate release locally within a developing thrombus using a glutamate sensitive enzymatic probe. The probe provides continuous real time glutamate concentration measurements by glutamate oxidase catalyzed conversion of glutamate to alpha-ketoglutaric acid and hydrogen peroxide. Hydrogen peroxide is then ampomerically detected (34). Whole blood was diluted in Tyrode's buffer (1:1) and glutamate concentration was measured during thrombin (0.5 U/mL) initiated platelet aggregation. Glutamate increases rapidly during platelet aggregation to concentrations exceeding 400 μM (FIG. 1 A-B). It was next determined whether glutamate is a mediator of platelet activation. Platelet rich plasma (PRP) was diluted 1:20 in Tyrode's buffer and incubated with glutamate (0-250 μM) for 5 min before activating platelets with a moderate Thrombin Receptor Activating Peptide (TRAP-6) concentration (5 μM) or a high concentration of TRAP (20 μM). Platelet activation was measured by FACS analysis for active conformation of surface GP IIb/IIIa using PAC-1 antibody (FIG. 2 A), (or by surface P-selectin expression, FIG. 9 B).

It was found that glutamate does not increase resting platelet activation (FIG. 2 A), but in the presence of glutamate, 5 μM of TRAP significantly increases platelet activation (FIG. 2 A). Glutamate has no effect at high TRAP concentrations (FIG. 2 A). A dose response curve with glutamate and moderate TRAP concentration (5 μM) was also performed and PAC-1 binding expressed as the percent increase in platelet mean fluorescence versus resting control platelets. Glutamate dose dependently increases platelet activation in response to TRAP (FIG. 2 B). As little as 150 μM of glutamate increases TRAP induced platelet activation by greater than 50% as compared to control treated platelets (FIG. 2 B). These are physiologically relevant plasma glutamate concentrations; control patient plasma glutamate is approximately 100 μM at baseline, in stroke patients can rise above 200 μM on admission, and our data in FIG. 1 A-B demonstrate that local glutamate concentrations in platelet aggregation can exceed 400 μM (27, 35). Glutamate also dose dependently increases platelet activation in response to the thromboxane mimetic U46619 (FIG. 2 C). Because glutamate appears to have a modulatory role in platelet activation, its effects were determined at concentrations that are most relevant: low concentrations of glutamate (150 μM) and low agonist concentrations (1 μM TRAP and U46619). Glutamate mediated increase in platelet activation following low concentration thromboxane mimetic is approximately three times greater than control, and approximately two times greater in response to TRAP (FIG. 2 D).

Example 2

Glutamate Mediates Platelet Activation and Aggregation through the AMPAR

Next, it was sought to identify the glutamate receptor that augments platelet activation. Others have demonstrated the presence of the NMDA type glutamate receptor (NMDAR) on platelets, but this appears to have a different role in platelet function (20, 22, 23). To determine whether NMDAR mediates glutamate activity, NMDAR was blocked with (±)-3-(2-Carboxypiperazin-4-yl)propyl-1-phosphonic acid (CPP) and then treated platelets with glutamate before stimulating with TRAP. NMDAR inhibition does not inhibit glutamate mediated increase in platelet activation (FIG. 3 A). It was therefore explored whether platelets express another type of ionotropic glutamate receptor. By immunoblot the presence of AMPA receptor (AMPAR) subunit proteins GluR1-4 was demonstrated (FIG. 3 B). Expression of the AMPAR subunit GluR1 was also localized to the platelet surface using flow cytometry (FACS) with an antibody specific for an external region of GluR1 (FIG. 3 C). These data demonstrate that platelets express the AMPA receptor.

Additionally, it was found that platelets express the kainate (KA) receptor. Using immunoblot and RT-polymerase chain reaction, the presence of the KA receptor, in particular the GluR5 subunit was confirmed on platelets, as shown in FIG. 10. The top panel shows the results of Western Blot experiments, and the bottom panel shows the results of RT-PCR.

Next, to define AMPAR's potential role as a mediator of platelet activation, PRP was incubated with control or AMPA (0.1-1 mM) and activated the platelets were activated or not TRAP. Similar to glutamate, pre-treatment of platelets with AMPA has no affect on resting platelets, but the treatment dose dependently increases agonist induced platelet activation (FIG. 4 A). AMPA also increases platelet activation in response to U46619 (FIG. 9 C).

Similar experiments were carried out to determine KA's potential role as a mediator of platelet activation. Using similar methodology, it was found that KA dose dependently increases TRAP induced platelet activation by FACS, as shown in FIG. 11.

Next, additional pharmacological approaches were used to demonstrate signaling through the AMPA receptor and its potential as a target for anti-thrombotic therapy. First, human platelets were incubated with control, the AMPAR inhibitor CNQX (100 μM), AMPA, or both, and then platelet activation was measured in response to TRAP. CNQX is an AMPAR inhibitor with some KA receptor blocking, but has a 20-150 fold selectivity for AMPAR subunits versus KA receptor subunits. As before, AMPA increases TRAP induced PAC-1 antibody binding (FIG. 4 B). CNQX inhibits TRAP induced platelet activation and inhibits the effects of AMPA upon platelet stimulation (FIG. 4 B). Furthermore, as little as 10 μM of CNQX significantly decreases platelet activation, likely by inhibition of released endogenous glutamate activities, indicating an autocrine role of glutamate in platelet activation (FIG. 4 C and FIG. 9 D). Other AMPAR inhibitors, such as NBQX, have similar effects (FIG. 9 E).

The functional relevance of platelet AMPAR was explored by isolating platelets from wild-type (WT) and GluR1 subunit knockout mice (GluR1-/-). Platelets from each type of mouse were incubated with vehicle or AMPA (1 mM), and then activated or not with thrombin (0.25 U/mL). Unstimulated platelets from WT and GluR1-/- mice have similar levels of activation, as measured by P-selectin localized to the platelet surface membrane (FIG. 4 D). However, WT platelets stimulated with thrombin have a greater increase in P-selectin externalization than GluR1-/- platelets. Furthermore, AMPA increases activation of WT platelets but not GluR1-/- platelets (FIG. 4 D).

It was further shown that KAR specific agonist (ATPA) increases platelet activation by FACS (FIG. 12), and the KAR specific inhibitor UBP302 dose dependently reduces platelet activation (FIG. 13).

Taken together, these data demonstrate that AMPA receptor signaling increases platelet activation and KA receptor signaling increases platelet activation.

Example 3

Platelet AMPAR Signaling Induces Sodium Influx and Platelet Depolarization

In the open state AMPA receptors are permeable to Na+, and depending on its subunit isoform composition, can also be selectively permeable to Ca2+. To determine if platelet AMPAR increases Na+ influx into platelets, platelets were pre-incubated with the Na+ sensitive dye sodium-binding benzofuran isophthalate (SBFI) and next added control, AMPA (1 mM), CNQX (100 µM), or both. Platelets were then activated or not with TRAP. It was found that AMPA increases intracellular Na+ concentration by approximately two times upon activation as compared to control (FIG. 5 A). CNQX not only decreases Na+ concentrations in platelets treated with AMPA and TRAP, but CNQX also decreases Na+ levels in platelets treated with TRAP alone (FIG. 5 A).

These data demonstrate that the AMPAR mediates an increase in intracellular Na+. To confirm that the AMPA receptor mediates Na+ influx independent of the Na+/H+ exchanger (NHE), the NHE was inhibited with amiloride (100 µM) (FIG. 9 F), and activated platelets or not with TRAP. Inhibition of the NHE reduces Na+ influx and platelet activation in response to TRAP (FIG. 5 B and FIG. 9). However, adding AMPA after amiloride restores Na+ influx and platelet activation, again suggesting that the AMPAR can act as a Na+ channel in platelet activation (FIG. 5 B). To further characterize the signaling induced by platelet AMPA receptor activation, electrophysiological recordings were carried out from freshly isolated megakaryocytes. Whole-cell recordings showed that rapid application of AMPA (0.1 or 1 mM, n=7; not shown) or Kainate (KA; 0.1 or 1 mM; n=3) did not induce a measurable current. In contrast, when the desensitization blocker cyclothiazide was included in the recording solution, a small but reproducible inward current was readily observed following rapid perfusion of AMPA (100 µM; 8.6+/−4.5 pA; n=9; FIG. 5 C) and Kainate (100 µM; 3.1+/−0.9 pA; n=7; FIG. 5 D). Whereas the inward current induced by KA was of sustained amplitude throughout the duration of the application, that induced by AMPA was typically of slightly greater amplitude at the beginning of the application and subsided to a steady-state value (FIG. 5 C). The current induced by AMPA was mediated by activation of AMPA receptors as demonstrated by the current blocked by administration of the AMPA receptor antagonist CNQX (30 µM; FIG. 5 E).

It was next sought to determine the reversal potential of the current induced by AMPA and KA by determining the current-voltage relationship of the agonist-induced inward current. In the case of AMPA application, it was somewhat difficult to reliably and reproducibly coincide the voltage steps with the short-lived peak current obtained at the very beginning of the application (FIG. 5 C). As a consequence, I-V curves were constructed from the delayed, steady-state part of the AMPA induced current. In these conditions, the current induced by both AMPA (n=5) and KA (n=5) reversed at a potential close to 0 mV and did not show any obvious rectification (FIG. 5 C-D). Together, the results from these electrophysiological recordings support the previous finging that megakaryocytes express on their surface functional AMPA receptors. In addition, the linear current-voltage relationship suggests that these receptors are GluR2 subunitcontaining AMPA receptors.

In addition to conferring a linear I-V relationship to the AMPA receptor complex, the incorporation of GluR2 subunit renders the AMPA receptor impermeable to calcium. Joro Spider Toxin (JST) allows pharmacological discrimination between these subtypes of AMPARs by selectively inhibiting GluR2-subunits (36). Next, platelets were incubated with JST (1 µM) prior to AMPA. JST pre-incubation had no effect on AMPA-mediated increase in platelet activation (FIG. 5 F). These results thus suggest that platelet AMPARs are of the GluR2-containing, Ca2+ impermeable AMPAR subtype. Taken together, these data suggest that the AMPA receptor modulates platelet activation in part by regulating Na+ influx.

Example 4

AMPAR Increases Platelet Activation in Response to GPCR Agonists

Others have demonstrated an increase in GPCR ligand affinity and activity subsequent to membrane depolarization (6-8). Glutamate increases both thrombin and thromboxane receptor (both GPCR) agonist induced platelet activation. To determine if it similarly increases platelet activation in response to other GPCR agonists, platelets were incubated with glutamate (250 and 500 µM) prior to activation with epinephrine, a GPCR ligand, or collagen, a non-GPCR ligand. Glutamate significantly increases epinephrine induced platelet activation (FIG. 6 A), but has no effect on collagen induced platelet activation (FIG. 6 B). As further proof, platelets were activated with ATP in the presence of glutamate. ATP stimulates platelet P2X1, a purine-dependent ligandgated ion channel for Ca2+ (37). ATP mediated platelet activation is not increased by glutamate (FIG. 6 C). Platelet P2Y receptors are GPCR purine dependent receptors, and activation of AMPAR increases platelet activation in response to GPCR agonists. These data support the idea that platelet AMPAR activation increases GPCR ligand signaling activity.

Example 5

AMPAR Inhibition Blocks Aggregation and Delays In Vivo Thrombosis

The functional relevance of targeting platelet AMPAR signaling was assayed by first measuring aggregation in response to TRAP (10 µM) after incubating platelets with control or CNQX (1-100 µM). CNQX dose dependently reduces platelet aggregation (FIG. 7 A-B). Exogenous AMPA (1 mM) was also added to platelets prior to aggregation. AMPA increases the rate of early aggregation. At 1 min post-TRAP control platelets are approximately 55% aggregated and AMPA pre-treated platelets approximately 75% (FIG. 7 C). At later time points the effect is less apparent (FIG. 7 C), likely a reflection of the large concentration of endogenous glutamate released into the growing platelet aggregate obscuring exogenous AMPA effects with time. These data demonstrate that platelet AMPAR presents a potential novel in vivo therapeutic target.

Next, in vivo studies were carried out to support this idea. Mice were treated intravenously (i.v.) with control PBS or CNQX (0.1 mg/kg) and 20 mins later tail bleeding times were determined. Control mice have an average bleeding time of approximately 200 sec with a cluster of mice that have very similar bleeding times (FIG. 8 A). AMPAR inhibitor treated mice have a prolonged average bleeding time (approximately 600 sec) and a greater range of bleeding times (FIG. 8 A). To confirm these data intravital microscopy was used to examine the role of platelet AMPAR signaling in thrombus formation. Platelets were isolated from control mice, fluorescently labeled and injected i.v. into recipient mice. Mice were then treated with CNQX or control PBS intravenously 20 mins prior to mesentery externalization and FeCl3 application. Images were collected to quantify in vivo platelet function (FIG. 8 B). Compared to PBS treated mice, mice treated with CNQX have prolonged time to platelet adhesion (greater than 10 platelets adherent for greater than 10 sec), thrombus formation (first stable thrombus greater than 20 µm), and total vessel occlusion (FIG. 8 C).

To determine if mice lacking the AMPAR subunit GluR1 have in vivo changes in platelet function, isolated platelets from WT control or GluR1−/− mice were fluorescently labeled and injected into mice of the same genotype. Mesenteric arterioles were then damaged with FeCl3 and thrombus formation again imaged. Similar to mice treated with the AMPAR inhibitor, mice lacking GluR1 have prolonged time to vessel occlusion as compared to WT control mice (FIG. 8 D).

In further experiments it was found that the KA receptor specific antagonist UBP302 prolongs bleeding time in mice, as shown in FIG. 14), and that mice treated with UBP302 have prolonged time to total vessel occlusion (FIG. 15).

The results and data presented herein demonstrate that glutamate receptors, in particular AMPA and kainate receptors, modulate platelet activation and thrombosis. These results have important implications for thrombotic diseases such as stroke, where plasma glutamate levels can rise significantly (25, 27). Following compromise of the blood brain barrier, glutamate released by neurons or platelets may contribute to the pathophysiology of stroke, not only as an excitatory amino acid, but also by acting as a prothrombotic messenger.

The results and data presented herein are not limited to cerebral vascular disease, but can apply to other pathological states. The data and results demonstrates that large concentrations of glutamate are released locally in platelet aggregation making glutamate signaling important in disease processes such as myocardial infarction and ischemia-reperfusion injury. Glutamate receptor antagonists, in particular AMPAR antagonists, may therefore be useful in the treatment and prevention of stroke, myocardial infarction, and other thrombotic diseases. One idea is that glutamate contained within platelet dense granules is released in high concentrations locally into 'the platelet synapse' as platelets come into close apposition during thrombus formation. This glutamate released into the formed platelet synapse early in platelet activation acts in an autocrine manner to promote complete platelet activation and in a paracrine fashion to rapidly increase the agonist sensitivity of recruited platelets. This helps drive and accelerate further thrombus formation. This is one model, not meant to be limiting to the invention as described herein. This model is supported by the data demonstrating that glutamate increases platelet sensitivity to low dose agonist stimulation, that AMPAR antagonists inhibit platelet function, and that mice lacking the AMPAR subunit GluR1 have prolonged time to vessel occlusion. Also possible are the potential contributions of AMPA receptors expressed by other vascular cells, or the potential contribution of other platelet expressed glutamate receptors, such as KA receptors or metabotropic glutamate receptors. Taken as a whole however, both the ex vivo and in vivo data demonstrate an important role for platelet glutamate and AMPAR in platelet activation and thrombus formation.

Glutamate function in thrombosis is very similar to that of another neurotransmitter, serotonin (5-HT). At basal conditions plasma 5-HT is relatively low and tightly regulated, but is rapidly released from dense granules upon platelet activation. Serotonin promotes continued platelet aggregation as evidenced by mice lacking the enzyme necessary for peripheral 5-HT production having prolonged time to vessel occlusion (38, 39). Similar to glutamate, 5-HT is a weak platelet agonist on its own and its effect is enhanced by the addition of other agonists (40). Serotonin reuptake inhibitors (SSRIs) may provide myocardial infarction protection, but have not been extensively studied or used clinically as a preventative therapy (39).

The data presented herein demonstrates that glutamate mediates an increase in platelet activation in response to the GPCR agonists thrombin, thromboxane, epinephrine, and ADP. However, glutamate has no effect on non-GPCR signaling pathways such as through the collagen or P2X receptors. The data presented herein also shows that AMPAR signaling increases platelet Na+ influx and induces an inward current that depolarizes megakaryoctye membranes. Membrane depolarization can lead to an increase in GPCR ligand affinity by creating a charge movement that increases G protein coupling with the GPCR (8, 37). Platelet G protein receptors contain positively charged internal amino acid regions that are possible voltage sensing domains. Alternatively, independent of a potential depolarization function, Na+ is an important ion in platelet activation. A rapid increase in intracellular Na+ is necessary to drive the Na+/Ca2+ exchanger and promote calcium mediated events in platelet activation. A function of platelet AMPAR may be as a rapid sodium channel. The electrophysiological studies support The results presented herein by showing that megakaryocytes express functional, most likely GluR2-containing, Ca2+-impermeable, AMPARs. Noteworthy, the inward current induced by AMPA application in megakaryocytes was of modest amplitude and only observed in the presence of a desensitization blocker, cyclothiazide. This contrasts with neurons where robust AMPAR-mediated inward currents are readily observed in the absence of cyclothiazide. Microglial cells however are similar to megakaryocyte in that AMPAR-mediated inward currents are only observed in the presence of cyclothiazide (41). Several mechanisms may account for these cell type-specific biophysical properties of AMPARs. For instance, Transmembrane AMPA Receptor Regulating Proteins (TARPs) are important modulators of AMPAR functions and their differential expression amongst cell types is expected to translate into different functional properties of AMPARs (35, 42).

There have been few reports of the NMDA receptor on platelets and megakaryocytes (20-23). Signaling through the NMDA receptor has been demonstrated to increase platelet production from megakaryoctyes (20, 23) and interestingly, NMDA receptor signaling in platelets has been shown to inhibit platelet aggregation (21, 22). The results presented herein show that glutamatemediated increase in platelet activation is independent of the NMDA receptor (FIG. 3 A). Prior NMDA receptor studies primarily utilized aggregation as the measure of platelet function, but endogenous platelet glutamate must be taken into account. As shown herein, a substantial concentration of glutamate is released in the developing thrombus that reaches peak levels very rapidly (FIG. 1) and exogenous glutamate or AMPA addition has no effect on final aggregation, one possibility being because the rapid release of endogenous glutamate obscures any effect.

NMDAR signaling in neurons is a means to regulate AMPAR trafficking by inducing an influx of Ca2+ that initiates the delivery of AMPA receptors from the recycling endosome to the surface membrane. Prior NMDAR studies in platelets demonstrate that NMDA induces an increase in Ca2+ influx and as a result may mediate an increase in AMPAR surface localization (21, 22). Other glutamate regulatory elements in platelets, such as the glutamate transporters (EAATs), have primarily been studied as peripheral markers of CNS disease. However, EAATs and other glutamate receptors may also have an important role in normal platelet function by controlling the plasma glutamate concentration. Individuals with polymorphisms in EAAT-2 have increased plasma glutamate concentrations with a higher frequency of early neurological worsening in stroke (27). These individuals may also be at increased risk of stroke, or that increased neurologic decline may be secondary to continued platelet activation and increased infarct size.

Methods

Reagents

L-glutamate, AMPA, CPP, ADP, CNQX:HBC, mouse thrombin, choline chloride, amiloride, U46619, and Joro Spider Toxin were purchased from Sigma. Antibody to GluR1 was purchased from Calbiochem; antibody to GluR2, GluR3, GluR4 were purchased from Santa Cruz; PAC-1 and P-Selectin antibodies were purchased from BD Pharmingen. FITC-IgG secondary antibody for FACS, SBFI, and BCEF were purchased from Molecular Probes. RTPCR reagents were purchased from Invitrogen. TRAP-6 was purchased from Bachem.

Platelet Isolation and Ex Vivo Experiments

Human platelets were isolated from healthy volunteers who had not taken aspirin or NSAID within 10 d, under a protocol approved by The Johns Hopkins University School of Medicine Institutional Review Board (JCCI). Blood was collected into citrate anticoagulant, platelets were isolated as platelet rich plasma (PRP) by centrifugation at 180 g for 15 min, and then diluted in Tyrode's buffer 1:20 for activation flow cytometry studies. To determine surface GluR1, a Fc Blocking antibody was added to reduce non-specific background antibody binding. Mouse platelets were isolated by collection into heparinized Tyrode's buffer and isolated by centrifugation. Washed platelets were resuspended in Tyrode's. Intracellular ion concentrations were performed after incubating platelets diluted 1:20 in Tyrode's buffer with SBFI for 45 minutes prior to experiments.

Glutamate Concentration

Whole blood was isolated as described and diluted 1:1 in Tyrode's buffer. A 1 mM glutamate sensitive probe (Pinnacle Technology Inc) was used to determine real-time glutamate concentrations. The glutamate biosensor relies on the glutamate oxidase catalyzed conversion of glutamate to alpha ketoglutaric acid and hydrogen peroxide. The enzymatically produced hydrogen peroxide is then ampomerically detected by its oxidation at the probes platinum-iridium electrode with an applied potential of 600 mV, with high sensitivity to glutamate at low (micromolar) concentrations, producing a linear response over a wide concentration range. The rapid response (1-4 s) is recorded using probe specific software to monitor the time course of a physiological glutamate release. Probe calibration was performed by incubating the probe in a gradient of glutamate concentrations. Voltage output and glutamate concentration were then correlated. While stirring the biosensor probe was placed in stirring blood and voltage recordings initiated. Thrombin was added to induce platelet activation and aggregation.

Immunoblotting

Platelets purchased from HemaCare and rat brain cerebellar lysate were lysed with NP-40 lysis buffer and supernatants were fractionated on a 4-15% gel. Membrane transferred proteins were immunoblotted with antibodies against GluR1-4.

In Vivo Studies

Mouse experiments were performed as approved by the Johns Hopkins University School of Medicine Animal Care and Use Committee.

Tail Bleeding 6 week old male mice were anesthetized with ketamine and xylazine (80/13 mg/kg) and injected i.v. with either PBS or CNQX:HBC, 0.1 mg/kg of active CNQX. Twenty minutes later the distal 3 mm of the tail was amputated, immersed in 37° C. saline and the time to visual cessation of bleeding recorded.

Intravital Microscopy

Platelets were isolated from mice as above and resuspended in Tyrode's at a concentration of $1\times10^8/100\,\mu L$, fluorescently labeled with 10 μM calcein-AM, and 100 μL injected intravenously into a mouse anesthetized with ketamine and xylazine. The mesentery was externalized, thrombosis initiated by the addition of a 5 mm2 piece of Whatmann's paper soaked in 10% FeCl3, and thrombosis recorded using a digital imaging camera and software (Retiga, QCapture Pro). GluR1−/− mice, on a C57B16/J background, were a generous gift of Rolf Sprengel, University of Heidelberg, Germany.

Electrophysiological Experiments

Cell Preparation and Solutions

All procedures using animals were approved by the University of Miyazaki Institutional Animal Care and Use Committee. Megakaryocyte preparation was performed as reported previously (43). Briefly, mouse bone marrow was flushed with Na+-rich external solution (Na+-ES, 150 mM NaCl, 1 mM CaCl2, and 10 mM HEPES, pH adjusted to 7.2 using NMDG-OH). Cells were dispersed by repetitive pipetting, washed three times by gentle centrifugation, resuspended in Na+-ES and used within 90 min of isolation.

Electrophysiological Studies

Whole-cell recordings were obtained from freshly isolated megakaryocytes using an intracellular solution of the following composition: 150 mM CsCl, 1 mM ethylene glycol bis(-aminoethylether)-N,N,N',N'-tetraacetic acid (EGTA) and 10 mM HEPES. The pH was adjusted to 7.3 using NMDG-OH. The patch-clamp procedures were similar to those described previously (43). Briefly, the experiments were performed in the tight seal whole-cell configuration at room temperature and electrical signals were acquired with an HEKA EPC-7 (Darmstadt, Germany). The pipette resistances ranged between 2 MΩ and 3 MΩ. Current-voltage relationships (I-V curves) were obtained by clamping the cell to different potentials in 30 mV increments (−30, 0 and +30 mV; each of 35 ms duration) from a holding potential of −60 mV. I-V curves obtained prior to the application of the agonists were subtracted from those (typically two) obtained in the presence of the agonists. The current responses were monitored on a chart recorder (WR7700, Graphtec, Tokyo, Japan) through a low-pass filter (200 Hz). Chemicals and reagents used were purchased from either Sigma (St. Louis, Mo.) or Wako Pure Chemicals (Osaka, Japan). Rapid perfusion of AMPA and Kainate was achieved by puff-application from a nearby pipette of 30-35 μm diameter to an isolated single megakaryocyte. The perfusion pipette was located within 30 μm of the cell and the puff pressure was adjusted to obtain rapid and effective agonist application (<10 msec).

Data Analysis

Data are expressed as means±standard deviation unless otherwise stated. Statistical comparisons between two groups were performed using Student's t-test.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

REFERENCES

1. Chen, D., A. M. Bernstein, P. P. Lemons, and S. W. Whiteheart. 2000. Molecular mechanisms of platelet exocytosis: role of SNAP-23 and syntaxin 2 in dense core granule release. Blood 95:921-929.
2. Das, I., N. S. Khan, B. K. Puri, S. R. Sooranna, J. de Belleroche, and S. R. Hirsch. 1995. Elevated platelet calcium mobilization and nitric oxide synthase activity may reflect abnormalities in schizophrenic brain. Biochem Biophys Res Commun 212:375-380.
3. Loscalzo, J. 2001. Nitric oxide insufficiency, platelet activation, and arterial thrombosis. Circ Res 88:756-762.
4. Roberts, D. E., A. McNicol, and R. Bose. 2004. Mechanism of collagen activation in human platelets. J Biol Chem 279:19421-19430.
5. Roberts, D. E., and R. Bose. 2002. Reverse mode Na+/Ca2+ exchange in the collagen activation of human platelets. Ann N Y Acad Sci 976:345-349.
6. Martinez-Pinna, J., I. S. Gurung, C. Vial, C. Leon, C. Gachet, R. J. Evans, and M. P. Mahaut-Smith. 2005. Direct voltage control of signaling via P2Y1 and other G alphaq coupled receptors. J Biol Chem 280:1490-1498.
7. Martinez-Pinna, J., G. Tolhurst, I. S. Gurung, J. I. Vandenberg, and M. P. Mahaut-Smith. 2004. Sensitivity limits for voltage control of P2Y receptor-evoked Ca2+ mobilization in the rat megakaryocyte. J Physiol 555:61-70.
8. Ben-Chaim, Y., B. Chanda, N. Dascal, F. Bezanilla, I. Parnas, and H. Parnas. 2006. Movement of 'gating charge' is coupled to ligand binding in a G-protein-coupled receptor. Nature 444:106-109. Glutamate Signals Through Platelet AMPAR 25
9. Kulick, M. B., and I. von Kugelgen. 2002. P2Y-receptors mediating an inhibition of the evoked entry of calcium through N-type calcium channels at neuronal processes. J Pharmacol Exp Ther 303:520-526.
10. Riddell, D. R., D. V. Vinogradov, A. K. Stannard, N. Chadwick, and J. S. Owen. 1999. Identification and characterization of LRP8 (apoER2) in human blood platelets. J Lipid Res 40:1925-1930.
11. Petit-Turcotte, C., N. Aumont, U. Beffert, D. Dea, J. Herz, and J. Poirier. 2005. The apoE receptor apoER2 is involved in the maintenance of efficient synaptic plasticity. Neurobiol Aging 26:195-206.
12. Hoogland, G., I. W. Bos, F. Kupper, G. van Willigen, H. A. Spierenburg, O. van Nieuwenhuizen, and P. N. de Graan. 2005. Thrombin-stimulated glutamate uptake in human platelets is predominantly mediated by the glial glutamate transporter EAAT2. Neurochem Int 47:499-506.
13. Zoia, C., T. Cogliati, E. Tagliabue, G. Cavaletti, G. Sala, G. Galimberti, I. Rivolta, V. Rossi, L. Frattola, and C. Ferrarese. 2004. Glutamate transporters in platelets: EAAT1 decrease in aging and in Alzheimer's disease. Neurobiol Aging 25:149-157.
14. Ferrarese, C., G. Sala, R. Riva, B. Begni, C. Zoia, L. Tremolizzo, G. Galimberti, A. Millul, A. Bastone, T. Mennini, C. Balzarini, L. Frattola, and E. Beghi. 2001. Decreased platelet glutamate uptake in patients with amyotrophic lateral sclerosis. Neurology 56:270-272.
15. Berk, M., H. Plein, and B. Belsham. 2000. The specificity of platelet glutamate receptor supersensitivity in psychotic disorders. Life Sci 66:2427-2432. Glutamate Signals Through Platelet AMPAR 26
16. Hinoi, E., T. Takarada, T. Ueshima, Y. Tsuchihashi, and Y. Yoneda. 2004. Glutamate signaling in peripheral tissues. Eur J Biochem 271:1-13.
17. Bertrand, G., R. Gross, R. Puech, M. M. Loubatieres-Mariani, and J. Bockaert. 1993. Glutamate stimulates glucagon secretion via an excitatory amino acid receptor of the AMPA subtype in rat pancreas. Eur J Pharmacol 237:45-50.
18. Chenu, C. 2002. Glutamatergic innervation in bone. Microsc Res Tech 58:70-76.
19. Spencer, G. J., and P. G. Genever. 2003. Long-term potentiation in bone—a role for glutamate in strain-induced cellular memory? BMC Cell Biol 4:9.
20. Hitchcock, I. S., T. M. Skerry, M. R. Howard, and P. G. Genever. 2003. NMDA receptormediated regulation of human megakaryocytopoiesis. Blood 102:1254-1259.
21. Franconi, F., M. Miceli, L. Alberti, G. Seghieri, M. G. De Montis, and A. Tagliamonte. 1998. Further insights into the anti-aggregating activity of NMDA in human platelets. Br J Pharmacol 124:35-40.
22. Franconi, F., M. Miceli, M. G. De Montis, E. L. Crisafi, F. Bennardini, and A. Tagliamonte. 1996. NMDA receptors play an anti-aggregating role in human platelets. Thromb Haemost 76:84-87.
23. Genever, P. G., D. J. Wilkinson, A. J. Patton, N. M. Peet, Y. Hong, A. Mathur, J. D. Erusalimsky, and T. M. Skerry. 1999. Expression of a functional N-methyl-D-aspartate-type glutamate receptor by bone marrow megakaryocytes. Blood 93:2876-2883.
24. Inagaki, N., H. Kuromi, T. Gonoi, Y. Okamoto, H. Ishida, Y. Seino, T. Kaneko, T. Iwanaga, and S. Seino. 1995. Expression and role of ionotropic glutamate receptors in pancreatic islet cells. Faseb J 9:686-691.
25. Aliprandi, A., M. Longoni, L. Stanzani, L. Tremolizzo, M. Vaccaro, B. Begni, G. Galimberti, R. Garofolo, and C. Ferrarese. 2005. Increased plasma glutamate in stroke patients might be linked to altered platelet release and uptake. J Cereb Blood Flow Metab 25:513-519.
26. Tremolizzo, L., J. C. Difrancesco, V. Rodriguez-Menendez, E. Sirtori, M. Longoni, A. Cassetti, M. Bossi, S. El Mestikawy, G. Cavaletti, and C. Ferrarese. 2006. Human platelets express the synaptic markers VGLUT1 and 2 and release glutamate following aggregation. Neurosci Lett
27. Mallolas, J., O. Hurtado, M. Castellanos, M. Blanco, T. Sobrino, J. Serena, J. Vivancos, J. Castillo, I. Lizasoain, M. A. Moro, and A. Davalos. 2006. A polymorphism in the EAAT2 promoter is associated with higher glutamate concentrations and higher frequency of progressing stroke. J Exp Med 203:711-717.
28. Malenka, R. C. 2003. Synaptic plasticity and AMPA receptor trafficking. Ann N Y Acad Sci 1003:1-11.
29. Malinow, R., and R. C. Malenka. 2002. AMPA receptor trafficking and synaptic plasticity. Annu Rev Neurosci 25:103-126.
30. Bredt, D. S., and R. A. Nicoll. 2003. AMPA receptor trafficking at excitatory synapses. Neuron 40:361-379.
31. Eastwood, S. L., P. W. Burnet, and P. J. Harrison. 1997. GluR2 glutamate receptor subunit flip and flop isoforms are decreased in the hippocampal formation in schizophrenia: a reverse transcriptase-polymerase chain reaction (RT-PCR) study. Brain Res Mol Brain Res 44:92-98.
32. Eastwood, S. L., P. W. Burnet, J. Beckwith, R. W. Kerwin, and P. J. Harrison. 1994. AMPA glutamate receptors and their flip and flop mRNAs in human hippocampus. Neuroreport 5:1325-1328.
33. Begni, B., L. Tremolizzo, C. D'Orlando, M. S. Bono, R. Garofolo, M. Longoni, and C. Ferrarese. 2005. Substrate-induced modulation of glutamate uptake in human platelets. Br J Pharmacol 145:792-799.

34. Morita, H., C. Abe, C. Awazu, and K. Tanaka. 2007. Long-term hypergravity induces plastic alterations in vestibulo-cardiovascular reflex in conscious rats. Neurosci Lett 412:201-205.
35. Tomita, S., H. Adesnik, M. Sekiguchi, W. Zhang, K. Wada, J. R. Howe, R. A. Nicoll, and D. S. Bredt. 2005. Stargazin modulates AMPA receptor gating and trafficking by distinct domains. Nature 435:1052-1058.
36. Blaschke, M., B. U. Keller, R. Rivosecchi, M. Hollmann, S. Heinemann, and A. Konnerth. 1993. A single amino acid determines the subunit-specific spider toxin block of alpha-amino-3-hydroxy-5-methylisoxazole-4-propionate/kainate receptor channels. Proc Natl Acad Sci USA 90:6528-6532.
37. Vial, C., S. J. Pitt, J. Roberts, M. G. Rolf, M. P. Mahaut-Smith, and R. J. Evans. 2003. Lack of evidence for functional ADP-activated human P2X1 receptors supports a role for ATP during hemostasis and thrombosis. Blood 102:3646-3651.
38. Walther, D. J., J. U. Peter, S. Winter, M. Holtje, N. Paulmann, M. Grohmann, J. Vowinckel, V. Alamo-Bethencourt, C. S. Wilhelm, G. Ahnert-Hilger, and M. Bader. 2003. Serotonylation of small GTPases is a signal transduction pathway that triggers platelet alpha-granule release. Cell 115:851-862.
39. Sauer, W. H., J. A. Berlin, and S. E. Kimmel. 2001. Selective serotonin reuptake inhibitors and myocardial infarction. Circulation 104:1894-1898.
40. Maurer-Spurej, E. 2005. Serotonin reuptake inhibitors and cardiovascular diseases: a platelet connection. Cell Mol Life Sci 62:159-170.
41. Hagino, Y., Y. Kariura, Y. Manago, T. Amano, B. Wang, M. Sekiguchi, K. Nishikawa, S. Aoki, K. Wada, and M. Noda. 2004. Heterogeneity and potentiation of AMPA type of glutamate receptors in rat cultured microglia. Glia 47:68-77.
42. Tomita, S., M. Sekiguchi, K. Wada, R. A. Nicoll, and D. S. Bredt. 2006. Stargazin controls the pharmacology of AMPA receptor potentiators. Proc Natl Acad Sci USA 103:10064-10067.
43. Ikeda, M. 2007. Characterization of functional P2X(1) receptors in mouse megakaryocytes. Thromb Res 119:343-353.

What is claimed is:

1. A method of delaying thrombus formation in a subject comprising:
   administering to the subject an effective amount of a compound that inhibits the activity of one or more glutamate receptors in non-neuronal cells, thereby delaying thrombus formation in a subject wherein the compound is selected from the group consisting of CNQX, NBQX, GYKI52466, GYKI53655, GYKI47261, cyclothiazide, YM90K, Zonampel (YM872), YM928, Perampanel (E2007), CP-465,022, ZK200775, Talampanel (LY300164), and Tezampanel (NGX424), LY382884, NS-102, UBP301, CX-516, CX-717, and philanthotoxin-343, and pharmaceutically acceptable salts, prodrugs, esters, and hydrates thereof.

2. The method of claim 1, wherein the method delays platelet activation, aggregation, adherence, clotting, or thrombosis.

3. The method of claim 1, wherein the AMPAR comprises at least one subunit selected from the group consisting of: GluR1, GluR2, GluR3 and GluR4.

4. A method of treating thrombosis in a subject comprising: administering to the subject an effective amount of a compound that inhibits the activity of AMPA receptors in non-neuronal cells in a subject, thereby treating thrombosis in the subject, wherein the compound is selected from the group consisting of CNQX, NBQX, GYK152466, GYK153655, GYK147261, cyclothiazide, YM90K, Zonampel (YM872), YM928, Perampanel (E2007), CP-465.022, ZK200775, Talampanel (LY300164), Tezampanel (NGX424), LY382884, NS-102, UBP301, CX-516, CX-717, and philanthotoxin-343, and pharmaceutically acceptable salts, prodrugs, esters, and hydrates thereof.

5. A method of delaying clot formation or progression in a subject comprising: administering to the subject an effective amount of a compound that inhibits the activity of AMPA receptors in platelet cells in a subject, thereby delaying clot formation or progression wherein the compound is selected from the group consisting of CNQX, NBQX, GYKI52466, GYKI53655, GYKI47261, cyclothiazide, YM90K, Zonampel (YM872), YM928, Perampanel (E2007), CP-465,022, ZK200775, Talampanel (LY300164), and Tezampanel (NGX424), LY382884, NS-102, UBP301, CX-516, CX-717, and philanthotoxin-343, and pharmaceutically acceptable salts, prodrugs, esters, and hydrates thereof.

6. A method of treating a thrombotic disease or disorder in a subject comprising: administering to the subject an effective amount of a compound that inhibits the activity of AMPA receptors in platelet cells in a subject and delays thrombus formation, thereby treating or preventing a thrombotic disease or disorder in a subject wherein the compound is selected from the group consisting of CNQX, NBQX, GYKI52466, GYKI53655, GYKI47261, cyclothiazide, YM90K, Zonampel (YM872), YM928, Perampanel (E2007), CP-465,022, ZK200775, Talampanel (LY300164), and Tezampanel (NGX424), LY382884, NS-102, UBP301, CX-516, CX-717, and philanthotoxin-343, and pharmaceutically acceptable salts, prodrugs, esters, and hydrates thereof.

* * * * *

UNITED STATES PATENT AND TRADEMARK OFFICE
CERTIFICATE OF CORRECTION

PATENT NO. : 8,603,980 B2
APPLICATION NO. : 12/523437
DATED : December 10, 2013
INVENTOR(S) : Craig N. Morrell and Charles J. Lowenstein It is certified that error appears in the above-identified patent and that said Letters Patent is hereby corrected as shown below:

In the Specification

Column 1, immediately after the title, please add the following paragraph:

STATEMENT OF GOVERNMENTAL INTEREST
This invention was made with government support under grant numbers HL074945, HL063706, HL074061, HL065608, HL056091, awarded by the National Institutes of Health. The government has certain rights in the invention.

Signed and Sealed this
Twenty-fourth Day of April, 2018

Andrei Iancu
*Director of the United States Patent and Trademark Office*

SEQUENCE LISTING

<160> NUMBER OF SEQ ID NOS: 10

<210> SEQ ID NO 1
<211> LENGTH: 906
<212> TYPE: PRT
<213> ORGANISM: Homo sapiens

<400> SEQUENCE: 1

```
Met Gln His Ile Phe Ala Phe Phe Cys Thr Gly Phe Leu Gly Ala Val
1               5                   10                  15

Val Gly Ala Asn Phe Pro Asn Asn Ile Gln Ile Gly Gly Leu Phe Pro
            20                  25                  30

Asn Gln Gln Ser Gln Glu His Ala Ala Phe Arg Phe Ala Leu Ser Gln
        35                  40                  45

Leu Thr Glu Pro Pro Lys Leu Leu Pro Gln Ile Asp Ile Val Asn Ile
    50                  55                  60

Ser Asp Ser Phe Glu Met Thr Tyr Arg Phe Cys Ser Gln Phe Ser Lys
65                  70                  75                  80

Gly Val Tyr Ala Ile Phe Gly Phe Tyr Glu Arg Arg Thr Val Asn Met
                85                  90                  95

Leu Thr Ser Phe Cys Gly Ala Leu His Val Cys Phe Ile Thr Pro Ser
            100                 105                 110

Phe Pro Val Asp Thr Ser Asn Gln Phe Val Leu Gln Leu Arg Pro Glu
        115                 120                 125

Leu Gln Asp Ala Leu Ile Ser Ile Ile Asp His Tyr Lys Trp Gln Lys
    130                 135                 140

Phe Val Tyr Ile Tyr Asp Ala Asp Arg Gly Leu Ser Val Leu Gln Lys
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
            180                 185                 190

Glu Lys Lys Lys Glu Arg Leu Val Val Val Asp Cys Glu Ser Glu Arg
        195                 200                 205
```

-continued

```
Leu Asn Ala Ile Leu Gly Gln Ile Ile Lys Leu Glu Lys Asn Gly Ile
            210                 215                 220
Gly Tyr His Tyr Ile Leu Ala Asn Leu Gly Phe Met Asp Ile Asp Leu
225                 230                 235                 240
Asn Lys Phe Lys Glu Ser Gly Ala Asn Val Thr Gly Phe Gln Leu Val
                245                 250                 255
Asn Tyr Thr Asp Thr Ile Pro Ala Lys Ile Met Gln Gln Trp Lys Asn
            260                 265                 270
Ser Asp Ala Arg Asp His Thr Arg Val Asp Trp Lys Arg Pro Lys Tyr
        275                 280                 285
Thr Ser Ala Leu Thr Tyr Asp Gly Val Lys Val Met Ala Glu Ala Phe
290                 295                 300
Gln Ser Leu Arg Arg Gln Arg Ile Asp Ile Ser Arg Arg Gly Asn Ala
305                 310                 315                 320
Gly Asp Cys Leu Ala Asn Pro Ala Val Pro Trp Gly Gln Gly Ile Asp
                325                 330                 335
Ile Gln Arg Ala Leu Gln Gln Val Arg Phe Glu Gly Leu Thr Gly Asn
            340                 345                 350
Val Gln Phe Asn Glu Lys Gly Arg Arg Thr Asn Tyr Thr Leu His Val
        355                 360                 365
Ile Glu Met Lys His Asp Ser Ile Arg Lys Ile Gly Tyr Trp Asn Glu
370                 375                 380
Asp Asp Lys Phe Val Pro Ala Ala Thr Asp Ala Gln Ala Gly Gly Asp
385                 390                 395                 400
Asn Ser Ser Val Gln Asn Arg Thr Tyr Ile Val Thr Thr Ile Leu Glu
                405                 410                 415
Asp Pro Tyr Val Met Leu Lys Lys Asn Ala Asn Gln Phe Glu Gly Asn
            420                 425                 430
Asp Arg Tyr Glu Gly Tyr Cys Val Glu Leu Ala Ala Glu Ile Ala Lys
        435                 440                 445
His Val Gly Tyr Ser Tyr Arg Leu Glu Ile Val Ser Asp Gly Lys Tyr
450                 455                 460
Gly Ala Arg Asp Pro Asp Thr Lys Ala Trp Asn Gly Met Val Gly Glu
465                 470                 475                 480
Leu Val Tyr Gly Arg Ala Asp Val Ala Val Ala Pro Leu Thr Ile Thr
                485                 490                 495
Leu Val Arg Glu Glu Val Ile Asp Phe Ser Lys Pro Phe Met Ser Leu
            500                 505                 510
Gly Ile Ser Ile Met Ile Lys Lys Pro Gln Lys Ser Lys Pro Gly Val
        515                 520                 525
Phe Ser Phe Leu Asp Pro Leu Ala Tyr Glu Ile Trp Met Cys Ile Val
530                 535                 540
Phe Ala Tyr Ile Gly Val Ser Val Val Leu Phe Leu Val Ser Arg Phe
545                 550                 555                 560
Ser Pro Tyr Glu Trp His Ser Glu Glu Phe Glu Glu Gly Arg Asp Gln
                565                 570                 575
Thr Thr Ser Asp Gln Ser Asn Glu Phe Gly Ile Phe Asn Ser Leu Trp
            580                 585                 590
Phe Ser Leu Gly Ala Phe Met Gln Gln Gly Cys Asp Ile Ser Pro Arg
        595                 600                 605
Ser Leu Ser Gly Arg Ile Val Gly Gly Val Trp Trp Phe Phe Thr Leu
610                 615                 620
Ile Ile Ile Ser Ser Tyr Thr Ala Asn Leu Ala Ala Phe Leu Thr Val
625                 630                 635                 640
```

```
Glu Arg Met Val Ser Pro Ile Glu Ser Ala Glu Asp Leu Ala Lys Gln
            645                 650                 655

Thr Glu Ile Ala Tyr Gly Thr Leu Glu Ala Gly Ser Thr Lys Glu Phe
            660                 665                 670

Phe Arg Arg Ser Lys Ile Ala Val Phe Glu Lys Met Trp Thr Tyr Met
            675                 680                 685

Lys Ser Ala Glu Pro Ser Val Phe Val Arg Thr Thr Glu Glu Gly Met
            690                 695                 700

Ile Arg Val Arg Lys Ser Lys Gly Lys Tyr Ala Tyr Leu Leu Glu Ser
705                 710                 715                 720

Thr Met Asn Glu Tyr Ile Glu Gln Arg Lys Pro Cys Asp Thr Met Lys
            725                 730                 735

Val Gly Gly Asn Leu Asp Ser Lys Gly Tyr Gly Ile Ala Thr Pro Lys
            740                 745                 750

Gly Ser Ala Leu Arg Asn Pro Val Asn Leu Ala Val Leu Lys Leu Asn
            755                 760                 765

Glu Gln Gly Leu Leu Asp Lys Leu Lys Asn Lys Trp Trp Tyr Asp Lys
            770                 775                 780

Gly Glu Cys Gly Ser Gly Gly Asp Ser Lys Asp Lys Thr Ser Ala
785                 790                 795                 800

Leu Ser Leu Ser Asn Val Ala Gly Val Phe Tyr Ile Leu Ile Gly Gly
            805                 810                 815

Leu Gly Leu Ala Met Leu Val Ala Leu Ile Glu Phe Cys Tyr Lys Ser
            820                 825                 830

Arg Ser Glu Ser Lys Arg Met Lys Gly Phe Cys Leu Ile Pro Gln Gln
            835                 840                 845

Ser Ile Asn Glu Ala Ile Arg Thr Ser Thr Leu Pro Arg Asn Ser Gly
            850                 855                 860

Ala Gly Ala Ser Ser Gly Gly Ser Gly Glu Asn Gly Arg Val Val Ser
865                 870                 875                 880

His Asp Phe Pro Lys Ser Met Gln Ser Ile Pro Cys Met Ser His Ser
            885                 890                 895

Ser Gly Met Pro Leu Gly Ala Thr Gly Leu
            900                 905

<210> SEQ ID NO 2
<211> LENGTH: 883
<212> TYPE: PRT
<213> ORGANISM: Homo sapiens

<400> SEQUENCE: 2

Met Gln Lys Ile Met His Ile Ser Val Leu Leu Ser Pro Val Leu Trp
1               5                   10                  15

Gly Leu Ile Phe Gly Val Ser Ser Asn Ser Ile Gln Ile Gly Gly Leu
            20                  25                  30

Phe Pro Arg Gly Ala Asp Gln Glu Tyr Ser Ala Phe Arg Val Gly Met
            35                  40                  45

Val Gln Phe Ser Thr Ser Glu Phe Arg Leu Thr Pro His Ile Asp Asn
        50                  55                  60

Leu Glu Val Ala Asn Ser Phe Ala Val Thr Asn Ala Phe Cys Ser Gln
65                  70                  75                  80

Phe Ser Arg Gly Val Tyr Ala Ile Phe Gly Phe Tyr Asp Lys Lys Ser
            85                  90                  95

Val Asn Thr Ile Thr Ser Phe Cys Gly Thr Leu His Val Ser Phe Ile
            100                 105                 110
```

```
Thr Pro Ser Phe Pro Thr Asp Gly Thr His Pro Phe Val Ile Gln Met
            115                 120                 125

Arg Pro Asp Leu Lys Gly Ala Leu Leu Ser Leu Ile Glu Tyr Tyr Gln
        130                 135                 140

Trp Asp Lys Phe Ala Tyr Leu Tyr Asp Ser Asp Arg Gly Leu Ser Thr
145                 150                 155                 160

Leu Gln Ala Val Leu Asp Ser Ala Ala Glu Lys Lys Trp Gln Val Thr
                165                 170                 175

Ala Ile Asn Val Gly Asn Ile Asn Asn Asp Lys Lys Asp Glu Met Tyr
            180                 185                 190

Arg Ser Leu Phe Gln Asp Leu Glu Leu Lys Lys Glu Arg Arg Val Ile
        195                 200                 205

Leu Asp Cys Glu Arg Asp Lys Val Asn Asp Ile Val Asp Gln Val Ile
    210                 215                 220

Thr Ile Gly Lys His Val Lys Gly Tyr His Tyr Ile Ile Ala Asn Leu
225                 230                 235                 240

Gly Phe Thr Asp Gly Asp Leu Leu Lys Ile Gln Phe Gly Gly Ala Asn
                245                 250                 255

Val Ser Gly Phe Gln Ile Val Asp Tyr Asp Asp Ser Leu Val Ser Lys
            260                 265                 270

Phe Ile Glu Arg Trp Ser Thr Leu Glu Glu Lys Glu Tyr Pro Gly Ala
        275                 280                 285

His Thr Thr Thr Ile Lys Tyr Thr Ser Ala Leu Thr Tyr Asp Ala Val
    290                 295                 300

Gln Val Met Thr Glu Ala Phe Arg Asn Leu Arg Lys Gln Arg Ile Glu
305                 310                 315                 320

Ile Ser Arg Arg Gly Asn Ala Gly Asp Cys Leu Ala Asn Pro Ala Val
                325                 330                 335

Pro Trp Gly Gln Gly Val Glu Ile Glu Arg Ala Leu Lys Gln Val Gln
            340                 345                 350

Val Glu Gly Leu Ser Gly Asn Ile Lys Phe Asp Gln Asn Gly Lys Arg
        355                 360                 365

Ile Asn Tyr Thr Ile Asn Ile Met Glu Leu Lys Thr Asn Gly Pro Arg
    370                 375                 380

Lys Ile Gly Tyr Trp Ser Glu Val Asp Lys Met Val Val Thr Leu Thr
385                 390                 395                 400

Glu Leu Pro Ser Gly Asn Asp Thr Ser Gly Leu Glu Asn Lys Thr Val
                405                 410                 415

Val Val Thr Thr Ile Leu Glu Ser Pro Tyr Val Met Met Lys Lys Asn
            420                 425                 430

His Glu Met Leu Glu Gly Asn Glu Arg Tyr Glu Gly Tyr Cys Val Asp
        435                 440                 445

Leu Ala Ala Glu Ile Ala Lys His Cys Gly Phe Lys Tyr Lys Leu Thr
    450                 455                 460

Ile Val Gly Asp Gly Lys Tyr Gly Ala Arg Asp Ala Asp Thr Lys Ile
465                 470                 475                 480

Trp Asn Gly Met Val Gly Glu Leu Val Tyr Gly Lys Ala Asp Ile Ala
                485                 490                 495

Ile Ala Pro Leu Thr Ile Thr Leu Val Arg Glu Glu Val Ile Asp Phe
            500                 505                 510

Ser Lys Pro Phe Met Ser Leu Gly Ile Ser Ile Met Ile Lys Lys Pro
        515                 520                 525

Gln Lys Ser Lys Pro Gly Val Phe Ser Phe Leu Asp Pro Leu Ala Tyr
```

```
                530             535             540
Glu Ile Trp Met Cys Ile Val Phe Ala Tyr Ile Gly Val Ser Val Val
545                 550                 555                 560

Leu Phe Leu Val Ser Arg Phe Ser Pro Tyr Glu Trp His Thr Glu Glu
                565                 570                 575

Phe Glu Asp Gly Arg Glu Thr Gln Ser Ser Glu Ser Thr Asn Glu Phe
                580                 585                 590

Gly Ile Phe Asn Ser Leu Trp Phe Ser Leu Gly Ala Phe Met Arg Gln
            595                 600                 605

Gly Cys Asp Ile Ser Pro Arg Ser Leu Ser Gly Arg Ile Val Gly Gly
            610                 615                 620

Val Trp Trp Phe Phe Thr Leu Ile Ile Ile Ser Ser Tyr Thr Ala Asn
625                 630                 635                 640

Leu Ala Ala Phe Leu Thr Val Glu Arg Met Val Ser Pro Ile Glu Ser
                645                 650                 655

Ala Glu Asp Leu Ser Lys Gln Thr Glu Ile Ala Tyr Gly Thr Leu Asp
                660                 665                 670

Ser Gly Ser Thr Lys Glu Phe Phe Arg Arg Ser Lys Ile Ala Val Phe
                675                 680                 685

Asp Lys Met Trp Thr Tyr Met Arg Ser Ala Glu Pro Ser Val Phe Val
                690                 695                 700

Arg Thr Thr Ala Glu Gly Val Ala Arg Val Arg Lys Ser Lys Gly Lys
705                 710                 715                 720

Tyr Ala Tyr Leu Leu Glu Ser Thr Met Asn Glu Tyr Ile Glu Gln Arg
                725                 730                 735

Lys Pro Cys Asp Thr Met Lys Val Gly Gly Asn Leu Asp Ser Lys Gly
                740                 745                 750

Tyr Gly Ile Ala Thr Pro Lys Gly Ser Ser Leu Arg Thr Pro Val Asn
            755                 760                 765

Leu Ala Val Leu Lys Leu Ser Glu Gln Gly Val Leu Asp Lys Leu Lys
770                 775                 780

Asn Lys Trp Trp Tyr Asp Lys Gly Glu Cys Gly Ala Lys Asp Ser Gly
785                 790                 795                 800

Ser Lys Glu Lys Thr Ser Ala Leu Ser Leu Ser Asn Val Ala Gly Val
                805                 810                 815

Phe Tyr Ile Leu Val Gly Gly Leu Gly Leu Ala Met Leu Val Ala Leu
            820                 825                 830

Ile Glu Phe Cys Tyr Lys Ser Arg Ala Glu Ala Lys Arg Met Lys Val
            835                 840                 845

Ala Lys Asn Ala Gln Asn Ile Asn Pro Ser Ser Ser Gln Asn Ser Gln
850                 855                 860

Asn Phe Ala Thr Tyr Lys Glu Gly Tyr Asn Val Tyr Gly Ile Glu Ser
865                 870                 875                 880

Val Lys Ile

<210> SEQ ID NO 3
<211> LENGTH: 869
<212> TYPE: PRT
<213> ORGANISM: Homo sapiens

<400> SEQUENCE: 3

Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
                20                  25                  30
```

```
Thr His Val Leu Arg Phe Gly Gly Ile Phe Glu Tyr Val Glu Ser Gly
         35                  40                  45

Pro Met Gly Ala Glu Glu Leu Ala Phe Arg Phe Ala Val Asn Thr Ile
 50                  55                  60

Asn Arg Asn Arg Thr Leu Leu Pro Asn Thr Thr Leu Thr Tyr Asp Thr
 65                  70                  75                  80

Gln Lys Ile Asn Leu Tyr Asp Ser Phe Glu Ala Ser Lys Lys Ala Cys
                 85                  90                  95

Asp Gln Leu Ser Leu Gly Val Ala Ala Ile Phe Gly Pro Ser His Ser
                100                 105                 110

Ser Ser Ala Asn Ala Val Gln Ser Ile Cys Asn Ala Leu Gly Val Pro
         115                 120                 125

His Ile Gln Thr Arg Trp Lys His Gln Val Ser Asp Asn Lys Asp Ser
 130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
                180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
                260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
        290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
                340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
        370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
        420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
```

```
            450             455             460
Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Ala Asn Gly
                485                 490                 495

Gln Trp Asn Gly Met Val Arg Glu Leu Ile Asp His Lys Ala Asp Leu
                500                 505                 510

Ala Val Ala Pro Leu Ala Ile Thr Tyr Val Arg Glu Lys Val Ile Asp
                515                 520                 525

Phe Ser Lys Pro Phe Met Thr Leu Gly Ile Ser Ile Leu Tyr Arg Lys
530                 535                 540

Pro Asn Gly Thr Asn Pro Gly Val Phe Ser Phe Leu Asn Pro Leu Ser
545                 550                 555                 560

Pro Asp Ile Trp Met Tyr Ile Leu Leu Ala Tyr Leu Gly Val Ser Cys
                565                 570                 575

Val Leu Phe Val Ile Ala Arg Phe Ser Pro Tyr Glu Trp Tyr Asn Pro
                580                 585                 590

His Pro Cys Asn Pro Asp Ser Asp Val Val Glu Asn Asn Phe Thr Leu
                595                 600                 605

Leu Asn Ser Phe Trp Phe Gly Val Gly Ala Leu Met Gln Gln Gly Ser
                610                 615                 620

Glu Leu Met Pro Lys Ala Leu Ser Thr Arg Ile Val Gly Gly Ile Trp
625                 630                 635                 640

Trp Phe Phe Thr Leu Ile Ile Ile Ser Ser Tyr Thr Ala Asn Leu Ala
                645                 650                 655

Ala Phe Leu Thr Val Glu Arg Met Glu Ser Pro Ile Asp Ser Ala Asp
                660                 665                 670

Asp Leu Ala Lys Gln Thr Lys Ile Glu Tyr Gly Ala Val Glu Asp Gly
                675                 680                 685

Ala Thr Met Thr Phe Phe Lys Lys Ser Lys Ile Ser Thr Tyr Asp Lys
                690                 695                 700

Met Trp Ala Phe Met Ser Ser Arg Arg Gln Ser Val Leu Val Lys Ser
705                 710                 715                 720

Asn Glu Glu Gly Ile Gln Arg Val Leu Thr Ser Asp Tyr Ala Phe Leu
                725                 730                 735

Met Glu Ser Thr Thr Ile Glu Phe Val Thr Gln Arg Asn Cys Asn Leu
                740                 745                 750

Thr Gln Ile Gly Gly Leu Ile Asp Ser Lys Gly Tyr Gly Val Gly Thr
                755                 760                 765

Pro Met Gly Ser Pro Tyr Arg Asp Lys Ile Thr Ile Ala Ile Leu Gln
770                 775                 780

Leu Gln Glu Glu Gly Lys Leu His Met Met Lys Glu Lys Trp Trp Arg
785                 790                 795                 800

Gly Asn Gly Cys Pro Glu Glu Ser Lys Ala Ser Ala Leu Gly
                805                 810                 815

Val Gln Asn Ile Gly Gly Ile Phe Ile Val Leu Ala Ala Gly Leu Val
                820                 825                 830

Leu Ser Val Phe Val Ala Val Gly Glu Phe Leu Tyr Lys Ser Lys Lys
                835                 840                 845

Asn Ala Gln Leu Glu Lys Glu Ser Ser Ile Trp Leu Val Pro Pro Tyr
850                 855                 860

His Pro Asp Thr Val
865
```

-continued

```
<210> SEQ ID NO 4
<211> LENGTH: 956
<212> TYPE: PRT
<213> ORGANISM: Homo sapiens

<400> SEQUENCE: 4

Met Pro Arg Val Ser Ala Pro Leu Val Leu Pro Ala Trp Leu Val
1               5                   10                  15

Met Val Ala Cys Ser Pro His Ser Leu Arg Ile Ala Ala Ile Leu Asp
                20                  25                  30

Asp Pro Met Glu Cys Ser Arg Gly Glu Arg Leu Ser Ile Thr Leu Ala
            35                  40                  45

Lys Asn Arg Ile Asn Arg Ala Pro Glu Arg Leu Gly Lys Ala Lys Val
50                  55                  60

Glu Val Asp Ile Phe Glu Leu Leu Arg Asp Ser Glu Tyr Glu Thr Ala
65                  70                  75                  80

Glu Thr Met Cys Gln Ile Leu Pro Lys Gly Val Val Ala Val Leu Gly
                85                  90                  95

Pro Ser Ser Ser Pro Ala Ser Ser Ile Ile Ser Asn Ile Cys Gly
            100                 105                 110

Glu Lys Glu Val Pro His Phe Lys Val Ala Pro Glu Glu Phe Val Lys
        115                 120                 125

Phe Gln Phe Gln Arg Phe Thr Thr Leu Asn Leu His Pro Ser Asn Thr
130                 135                 140

Asp Ile Ser Val Ala Val Ala Gly Ile Leu Asn Phe Phe Asn Cys Thr
145                 150                 155                 160

Thr Ala Cys Leu Ile Cys Ala Lys Ala Glu Cys Leu Leu Asn Leu Glu
                165                 170                 175

Lys Leu Leu Arg Gln Phe Leu Ile Ser Lys Asp Thr Leu Ser Val Arg
            180                 185                 190

Met Leu Asp Asp Thr Arg Asp Pro Thr Pro Leu Leu Lys Glu Ile Arg
        195                 200                 205

Asp Asp Lys Thr Ala Thr Ile Ile Ile His Ala Asn Ala Ser Met Ser
210                 215                 220

His Thr Ile Leu Leu Lys Ala Ala Glu Leu Gly Met Val Ser Ala Tyr
225                 230                 235                 240

Tyr Thr Tyr Ile Phe Thr Asn Leu Glu Phe Ser Leu Gln Arg Met Asp
                245                 250                 255

Ser Leu Val Asp Asp Arg Val Asn Ile Leu Gly Phe Ser Ile Phe Asn
            260                 265                 270

Gln Ser His Ala Phe Phe Gln Glu Phe Ala Gln Ser Leu Asn Gln Ser
        275                 280                 285

Trp Gln Glu Asn Cys Asp His Val Pro Phe Thr Gly Pro Ala Leu Ser
290                 295                 300

Ser Ala Leu Leu Phe Asp Ala Val Tyr Ala Val Val Thr Ala Val Gln
305                 310                 315                 320

Glu Leu Asn Arg Ser Gln Glu Ile Gly Val Lys Pro Leu Ser Cys Gly
                325                 330                 335

Ser Ala Gln Ile Trp Gln His Gly Thr Ser Leu Met Asn Tyr Leu Arg
            340                 345                 350

Met Val Glu Leu Glu Gly Leu Thr Gly His Ile Glu Phe Asn Ser Lys
        355                 360                 365

Gly Gln Arg Ser Asn Tyr Ala Leu Lys Ile Leu Gln Phe Thr Arg Asn
370                 375                 380
```

-continued

```
Gly Phe Arg Gln Ile Gly Gln Trp His Val Ala Glu Gly Leu Ser Met
385                 390                 395                 400

Asp Ser His Leu Tyr Ala Ser Asn Ile Ser Asp Thr Leu Phe Asn Thr
            405                 410                 415

Thr Leu Val Val Thr Thr Ile Leu Glu Asn Pro Tyr Leu Met Leu Lys
        420                 425                 430

Gly Asn His Gln Glu Met Glu Gly Asn Asp Arg Tyr Glu Gly Phe Cys
            435                 440                 445

Val Asp Met Leu Lys Glu Leu Ala Glu Ile Leu Arg Phe Asn Tyr Lys
        450                 455                 460

Ile Arg Leu Val Gly Asp Gly Val Tyr Gly Val Pro Glu Ala Asn Gly
465                 470                 475                 480

Thr Trp Thr Gly Met Val Gly Glu Leu Ile Ala Arg Lys Ala Asp Leu
                485                 490                 495

Ala Val Ala Gly Leu Thr Ile Thr Ala Glu Arg Glu Lys Val Ile Asp
            500                 505                 510

Phe Ser Lys Pro Phe Met Thr Leu Gly Ile Ser Ile Leu Tyr Arg Val
        515                 520                 525

His Met Gly Arg Lys Pro Gly Tyr Phe Ser Phe Leu Asp Pro Phe Ser
530                 535                 540

Pro Gly Val Trp Leu Phe Met Leu Leu Ala Tyr Leu Ala Val Ser Cys
545                 550                 555                 560

Val Leu Phe Leu Val Ala Arg Leu Thr Pro Tyr Glu Trp Tyr Ser Pro
                565                 570                 575

His Pro Cys Ala Gln Gly Arg Cys Asn Leu Leu Val Asn Gln Tyr Ser
            580                 585                 590

Leu Gly Asn Ser Leu Trp Phe Pro Val Gly Gly Phe Met Gln Gln Gly
        595                 600                 605

Ser Thr Ile Ala Pro Arg Ala Leu Ser Thr Arg Cys Val Ser Gly Val
            610                 615                 620

Trp Trp Ala Phe Thr Leu Ile Ile Ile Ser Ser Tyr Thr Ala Asn Leu
625                 630                 635                 640

Ala Ala Phe Leu Thr Val Gln Arg Met Asp Val Pro Ile Glu Ser Val
                645                 650                 655

Asp Asp Leu Ala Asp Gln Thr Ala Ile Glu Tyr Gly Thr Ile His Gly
            660                 665                 670

Gly Ser Ser Met Thr Phe Phe Gln Asn Ser Arg Tyr Gln Thr Tyr Gln
        675                 680                 685

Arg Met Trp Asn Tyr Met Tyr Ser Lys Gln Pro Ser Val Phe Val Lys
            690                 695                 700

Ser Thr Glu Glu Gly Ile Ala Arg Val Leu Asn Ser Asn Tyr Ala Phe
705                 710                 715                 720

Leu Leu Glu Ser Thr Met Asn Glu Tyr Tyr Arg Gln Arg Asn Cys Asn
                725                 730                 735

Leu Thr Gln Ile Gly Gly Leu Leu Asp Thr Lys Gly Tyr Gly Ile Gly
            740                 745                 750

Met Pro Val Gly Ser Val Phe Arg Asp Glu Phe Asp Leu Ala Ile Leu
        755                 760                 765

Gln Leu Gln Glu Asn Asn Arg Leu Glu Ile Leu Lys Arg Lys Trp Trp
770                 775                 780

Glu Gly Gly Lys Cys Pro Lys Glu Glu Asp His Arg Ala Lys Gly Leu
785                 790                 795                 800

Gly Met Glu Asn Ile Gly Gly Ile Phe Val Val Leu Ile Cys Gly Leu
                805                 810                 815
```

```
Ile Val Ala Ile Phe Met Ala Met Leu Glu Phe Leu Trp Thr Leu Arg
                820             825                 830

His Ser Glu Ala Thr Glu Val Ser Val Cys Gln Glu Met Val Thr Glu
        835                 840                 845

Leu Arg Ser Ile Ile Leu Cys Gln Asp Ser Ile His Pro Arg Arg Arg
    850                 855                 860

Arg Ala Ala Val Pro Pro Arg Pro Pro Ile Pro Glu Glu Arg Arg
865             870                 875                 880

Pro Arg Gly Thr Ala Thr Leu Ser Asn Gly Lys Leu Cys Gly Ala Gly
            885                 890                 895

Glu Pro Asp Gln Leu Ala Gln Arg Leu Ala Gln Glu Ala Ala Leu Val
        900                 905                 910

Ala Arg Gly Cys Thr His Ile Arg Val Cys Pro Glu Cys Arg Arg Phe
            915                 920                 925

Gln Gly Leu Arg Ala Arg Pro Ser Pro Ala Arg Ser Glu Glu Ser Leu
        930                 935                 940

Glu Trp Glu Lys Thr Thr Asn Ser Ser Glu Pro Glu
945             950                 955

<210> SEQ ID NO 5
<211> LENGTH: 980
<212> TYPE: PRT
<213> ORGANISM: Homo sapiens

<400> SEQUENCE: 5

Met Pro Ala Glu Leu Leu Leu Leu Ile Val Ala Phe Ala Ser Pro
1               5                   10                  15

Ser Cys Gln Val Leu Ser Ser Leu Arg Met Ala Ala Ile Leu Asp Asp
                20                  25                  30

Gln Thr Val Cys Gly Arg Gly Glu Arg Leu Ala Leu Ala Leu Ala Arg
            35                  40                  45

Glu Gln Ile Asn Gly Ile Ile Glu Val Pro Ala Lys Ala Arg Val Glu
        50                  55                  60

Val Asp Ile Phe Glu Leu Gln Arg Asp Ser Gln Tyr Glu Thr Thr Asp
65                  70                  75                  80

Thr Met Cys Gln Ile Leu Pro Lys Gly Val Val Ser Val Leu Gly Pro
                85                  90                  95

Ser Ser Ser Pro Ala Ser Ala Ser Thr Val Ser His Ile Cys Gly Glu
                100                 105                 110

Lys Glu Ile Pro His Ile Lys Val Gly Pro Glu Glu Thr Pro Arg Leu
            115                 120                 125

Gln Tyr Leu Arg Phe Ala Ser Val Ser Leu Tyr Pro Ser Asn Glu Asp
        130                 135                 140

Val Ser Leu Ala Val Ser Arg Ile Leu Lys Ser Phe Asn Tyr Pro Ser
145                 150                 155                 160

Ala Ser Leu Ile Cys Ala Lys Ala Glu Cys Leu Leu Arg Leu Glu Glu
                165                 170                 175

Leu Val Arg Gly Phe Leu Ile Ser Lys Glu Thr Leu Ser Val Arg Met
            180                 185                 190

Leu Asp Asp Ser Arg Asp Pro Thr Pro Leu Leu Lys Glu Ile Arg Asp
        195                 200                 205

Asp Lys Val Ser Thr Ile Ile Ile Asp Ala Asn Ala Ser Ile Ser His
    210                 215                 220

Leu Ile Leu Arg Lys Ala Ser Glu Leu Gly Met Thr Ser Ala Phe Tyr
225                 230                 235                 240
```

```
Lys Tyr Ile Leu Thr Thr Met Asp Phe Pro Ile Leu His Leu Asp Gly
                245                 250                 255

Ile Val Glu Asp Ser Ser Asn Ile Leu Gly Phe Ser Met Phe Asn Thr
                260                 265                 270

Ser His Pro Phe Tyr Pro Glu Phe Val Arg Ser Leu Asn Met Ser Trp
                275                 280                 285

Arg Glu Asn Cys Glu Ala Ser Thr Tyr Leu Gly Pro Ala Leu Ser Ala
                290                 295                 300

Ala Leu Met Phe Asp Ala Val His Val Val Ser Ala Val Arg Glu
305                 310                 315                 320

Leu Asn Arg Ser Gln Glu Ile Gly Val Lys Pro Leu Ala Cys Thr Ser
                325                 330                 335

Ala Asn Ile Trp Pro His Gly Thr Ser Leu Met Asn Tyr Leu Arg Met
                340                 345                 350

Val Glu Tyr Asp Gly Leu Thr Gly Arg Val Glu Phe Asn Ser Lys Gly
                355                 360                 365

Gln Arg Thr Asn Tyr Thr Leu Arg Ile Leu Glu Lys Ser Arg Gln Gly
                370                 375                 380

His Arg Glu Ile Gly Val Trp Tyr Ser Asn Arg Thr Leu Ala Met Asn
385                 390                 395                 400

Ala Thr Thr Leu Asp Ile Asn Leu Ser Gln Thr Leu Ala Asn Lys Thr
                405                 410                 415

Leu Val Val Thr Thr Ile Leu Glu Asn Pro Tyr Val Met Arg Arg Pro
                420                 425                 430

Asn Phe Gln Ala Leu Ser Gly Asn Glu Arg Phe Glu Gly Phe Cys Val
                435                 440                 445

Asp Met Leu Arg Glu Leu Ala Glu Leu Leu Arg Phe Arg Tyr Arg Leu
                450                 455                 460

Arg Leu Val Glu Asp Gly Leu Tyr Gly Ala Pro Glu Pro Asn Gly Ser
465                 470                 475                 480

Trp Thr Gly Met Val Gly Glu Leu Ile Asn Arg Lys Ala Asp Leu Ala
                485                 490                 495

Val Ala Ala Phe Thr Ile Thr Ala Glu Arg Glu Lys Val Ile Asp Phe
                500                 505                 510

Ser Lys Pro Phe Met Thr Leu Gly Ile Ser Ile Leu Tyr Arg Val His
                515                 520                 525

Met Gly Arg Lys Pro Gly Tyr Phe Ser Phe Leu Asp Pro Phe Ser Pro
                530                 535                 540

Ala Val Trp Leu Phe Met Leu Leu Ala Tyr Leu Ala Val Ser Cys Val
545                 550                 555                 560

Leu Phe Leu Ala Ala Arg Leu Ser Pro Tyr Glu Trp Tyr Asn Pro His
                565                 570                 575

Pro Cys Leu Arg Ala Arg Pro His Ile Leu Glu Asn Gln Tyr Thr Leu
                580                 585                 590

Gly Asn Ser Leu Trp Phe Pro Val Gly Gly Phe Met Gln Gln Gly Ser
                595                 600                 605

Glu Ile Met Pro Arg Ala Leu Ser Thr Arg Cys Val Ser Gly Val Trp
                610                 615                 620

Trp Ala Phe Thr Leu Ile Ile Ile Ser Ser Tyr Thr Ala Asn Leu Ala
625                 630                 635                 640

Ala Phe Leu Thr Val Gln Arg Met Glu Val Pro Val Glu Ser Ala Asp
                645                 650                 655

Asp Leu Ala Asp Gln Thr Asn Ile Glu Tyr Gly Thr Ile His Ala Gly
```

-continued

```
                    660                 665                 670
Ser Thr Met Thr Phe Phe Gln Asn Ser Arg Tyr Gln Thr Tyr Gln Arg
                675                 680                 685

Met Trp Asn Tyr Met Gln Ser Lys Gln Pro Ser Val Phe Val Lys Ser
        690                 695                 700

Thr Glu Glu Gly Ile Ala Arg Val Leu Asn Ser Arg Tyr Ala Phe Leu
705                 710                 715                 720

Leu Glu Ser Thr Met Asn Glu Tyr His Arg Arg Leu Asn Cys Asn Leu
                725                 730                 735

Thr Gln Ile Gly Gly Leu Leu Asp Thr Lys Gly Tyr Gly Ile Gly Met
            740                 745                 750

Pro Leu Gly Ser Pro Phe Arg Asp Glu Ile Thr Leu Ala Ile Leu Gln
        755                 760                 765

Leu Gln Glu Asn Asn Arg Leu Glu Ile Leu Lys Arg Lys Trp Trp Glu
    770                 775                 780

Gly Gly Arg Cys Pro Lys Glu Asp His Arg Ala Lys Gly Leu Gly
785                 790                 795                 800

Met Glu Asn Ile Gly Gly Ile Phe Ile Val Leu Ile Cys Gly Leu Ile
                805                 810                 815

Ile Ala Val Phe Val Ala Val Met Glu Phe Ile Trp Ser Thr Arg Arg
            820                 825                 830

Ser Ala Glu Ser Glu Val Ser Val Cys Gln Glu Met Leu Gln Glu
        835                 840                 845

Leu Arg His Ala Val Ser Cys Arg Lys Thr Ser Arg Ser Arg Arg
    850                 855                 860

Arg Arg Pro Gly Gly Pro Ser Arg Ala Leu Leu Ser Leu Arg Ala Val
865                 870                 875                 880

Arg Glu Met Arg Leu Ser Asn Gly Lys Leu Tyr Ser Ala Gly Ala Gly
                885                 890                 895

Gly Asp Ala Gly Ser Ala His Gly Gly Pro Gln Arg Leu Leu Asp Asp
            900                 905                 910

Pro Gly Pro Pro Ser Gly Ala Arg Pro Ala Ala Pro Thr Pro Cys Thr
        915                 920                 925

His Val Arg Val Cys Gln Glu Cys Arg Arg Ile Gln Ala Leu Arg Ala
    930                 935                 940

Ser Gly Ala Gly Ala Pro Pro Arg Gly Leu Gly Val Pro Ala Glu Ala
945                 950                 955                 960

Thr Ser Pro Pro Arg Pro Arg Pro Gly Pro Ala Gly Pro Arg Glu Leu
                965                 970                 975

Ala Glu His Glu
            980

<210> SEQ ID NO 6
<211> LENGTH: 879
<212> TYPE: PRT
<213> ORGANISM: Homo sapiens

<400> SEQUENCE: 6

Met Lys Met Leu Thr Arg Leu Gln Val Leu Thr Leu Ala Leu Phe Ser
1               5                   10                  15

Lys Gly Phe Leu Leu Ser Leu Gly Asp His Asn Phe Leu Arg Arg Glu
                20                  25                  30

Ile Lys Ile Glu Gly Asp Leu Val Leu Gly Gly Leu Phe Pro Ile Asn
            35                  40                  45

Glu Lys Gly Thr Gly Thr Glu Glu Cys Gly Arg Ile Asn Glu Asp Arg
```

```
            50                  55                  60
Gly Ile Gln Arg Leu Glu Ala Met Leu Phe Ala Ile Asp Glu Ile Asn
65                  70                  75                  80

Lys Asp Asp Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
                100                 105                 110

Val Arg Ala Ser Leu Thr Lys Val Asp Glu Ala Glu Tyr Met Cys Pro
                115                 120                 125

Asp Gly Ser Tyr Ala Ile Gln Glu Asn Ile Pro Leu Leu Ile Ala Gly
                130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
                180                 185                 190

Pro Asp Phe Tyr Gln Ala Lys Ala Met Ala Glu Ile Leu Arg Phe Phe
                195                 200                 205

Asn Trp Thr Tyr Val Ser Thr Val Ala Ser Glu Gly Asp Tyr Gly Glu
                210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
                260                 265                 270

Val Leu Phe Met Arg Ser Asp Asp Ser Arg Glu Leu Ile Ala Ala Ala
                275                 280                 285

Ser Arg Ala Asn Ala Ser Phe Thr Trp Val Ala Ser Asp Gly Trp Gly
                290                 295                 300

Ala Gln Glu Ser Ile Ile Lys Gly Ser Glu His Val Ala Tyr Gly Ala
305                 310                 315                 320

Ile Thr Leu Glu Leu Ala Ser Gln Pro Val Arg Gln Phe Asp Arg Tyr
                325                 330                 335

Phe Gln Ser Leu Asn Pro Tyr Asn Asn His Arg Asn Pro Trp Phe Arg
                340                 345                 350

Asp Phe Trp Glu Gln Lys Phe Gln Cys Ser Leu Gln Asn Lys Arg Asn
                355                 360                 365

His Arg Arg Val Cys Asp Lys His Leu Ala Ile Asp Ser Ser Asn Tyr
                370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
                420                 425                 430

Asp Tyr Leu Leu Lys Ile Asn Phe Thr Ala Pro Phe Asn Pro Asn Lys
                435                 440                 445

Asp Ala Asp Ser Ile Val Lys Phe Asp Thr Phe Gly Asp Gly Met Gly
                450                 455                 460

Arg Tyr Asn Val Phe Asn Phe Gln Asn Val Gly Gly Lys Tyr Ser Tyr
465                 470                 475                 480
```

```
Leu Lys Val Gly His Trp Ala Glu Thr Leu Ser Leu Asp Val Asn Ser
            485                 490                 495

Ile His Trp Ser Arg Asn Ser Val Pro Thr Ser Gln Cys Ser Asp Pro
            500                 505                 510

Cys Ala Pro Asn Glu Met Lys Asn Met Gln Pro Gly Asp Val Cys Cys
            515                 520                 525

Trp Ile Cys Ile Pro Cys Glu Pro Tyr Glu Tyr Leu Ala Asp Glu Phe
            530                 535                 540

Thr Cys Met Asp Cys Gly Ser Gly Gln Trp Pro Thr Ala Asp Leu Thr
545                 550                 555                 560

Gly Cys Tyr Asp Leu Pro Glu Asp Tyr Ile Arg Trp Glu Asp Ala Trp
            565                 570                 575

Ala Ile Gly Pro Val Thr Ile Ala Cys Leu Gly Phe Met Cys Thr Cys
            580                 585                 590

Met Val Val Thr Val Phe Ile Lys His Asn Asn Thr Pro Leu Val Lys
            595                 600                 605

Ala Ser Gly Arg Glu Leu Cys Tyr Ile Leu Leu Phe Gly Val Gly Leu
            610                 615                 620

Ser Tyr Cys Met Thr Phe Phe Phe Ile Ala Lys Pro Ser Pro Val Ile
625                 630                 635                 640

Cys Ala Leu Arg Arg Leu Gly Leu Gly Ser Ser Phe Ala Ile Cys Tyr
            645                 650                 655

Ser Ala Leu Leu Thr Lys Thr Asn Cys Ile Ala Arg Ile Phe Asp Gly
            660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
            690                 695                 700

Val Trp Leu Ile Leu Glu Ala Pro Gly Thr Arg Arg Tyr Thr Leu Ala
705                 710                 715                 720

Glu Lys Arg Glu Thr Val Ile Leu Lys Cys Asn Val Lys Asp Ser Ser
            725                 730                 735

Met Leu Ile Ser Leu Thr Tyr Asp Val Ile Leu Val Ile Leu Cys Thr
            740                 745                 750

Val Tyr Ala Phe Lys Thr Arg Lys Cys Pro Glu Asn Phe Asn Glu Ala
            755                 760                 765

Lys Phe Ile Gly Phe Thr Met Tyr Thr Thr Cys Ile Ile Trp Leu Ala
            770                 775                 780

Phe Leu Pro Ile Phe Tyr Val Thr Ser Ser Asp Tyr Arg Val Gln Thr
785                 790                 795                 800

Thr Thr Met Cys Ile Ser Val Ser Leu Ser Gly Phe Val Val Leu Gly
            805                 810                 815

Cys Leu Phe Ala Pro Lys Val His Ile Ile Leu Phe Gln Pro Gln Lys
            820                 825                 830

Asn Val Val Thr His Arg Leu His Leu Asn Arg Phe Ser Val Ser Gly
            835                 840                 845

Thr Gly Thr Thr Tyr Ser Gln Ser Ser Ala Ser Thr Tyr Val Pro Thr
            850                 855                 860

Val Cys Asn Gly Arg Glu Val Leu Asp Ser Thr Thr Ser Ser Leu
865                 870                 875

<210> SEQ ID NO 7
<211> LENGTH: 902
<212> TYPE: PRT
<213> ORGANISM: Homo sapiens
```

-continued

```
<400> SEQUENCE: 7

Met Arg Ile Ile Ser Arg Gln Ile Val Leu Phe Ser Gly Phe Trp
1               5                   10                  15

Gly Leu Ala Met Gly Ala Phe Pro Ser Ser Val Gln Ile Gly Gly Leu
            20                  25                  30

Phe Ile Arg Asn Thr Asp Gln Glu Tyr Thr Ala Phe Arg Leu Ala Ile
        35                  40                  45

Phe Leu His Asn Thr Ser Pro Asn Ala Ser Glu Ala Pro Phe Asn Leu
50                  55                  60

Val Pro His Val Asp Asn Ile Glu Thr Ala Asn Ser Phe Ala Val Thr
65                  70                  75                  80

Asn Ala Phe Cys Ser Gln Tyr Ser Arg Gly Val Phe Ala Ile Phe Gly
                85                  90                  95

Leu Tyr Asp Lys Arg Ser Val His Thr Leu Thr Ser Phe Cys Ser Ala
            100                 105                 110

Leu His Ile Ser Leu Ile Thr Pro Ser Phe Pro Thr Glu Gly Glu Ser
        115                 120                 125

Gln Phe Val Leu Gln Leu Arg Pro Ser Leu Arg Gly Ala Leu Leu Ser
130                 135                 140

Leu Leu Asp His Tyr Glu Trp Asn Cys Phe Val Phe Leu Tyr Asp Thr
145                 150                 155                 160

Asp Arg Gly Tyr Ser Ile Leu Gln Ala Ile Met Glu Lys Ala Gly Gln
                165                 170                 175

Asn Gly Trp His Val Ser Ala Ile Cys Val Glu Asn Phe Asn Asp Val
            180                 185                 190

Ser Tyr Arg Gln Leu Leu Glu Glu Leu Asp Arg Arg Gln Glu Lys Lys
        195                 200                 205

Phe Val Ile Asp Cys Glu Ile Glu Arg Leu Gln Asn Ile Leu Glu Gln
210                 215                 220

Ile Val Ser Val Gly Lys His Val Lys Gly Tyr His Tyr Ile Ile Ala
225                 230                 235                 240

Asn Leu Gly Phe Lys Asp Ile Ser Leu Glu Arg Phe Ile His Gly Gly
                245                 250                 255

Ala Asn Val Thr Gly Phe Gln Leu Val Asp Phe Asn Thr Pro Met Val
            260                 265                 270

Ile Lys Leu Met Asp Arg Trp Lys Lys Leu Asp Gln Arg Glu Tyr Pro
        275                 280                 285

Gly Ser Glu Thr Pro Pro Lys Tyr Thr Ser Ala Leu Thr Tyr Asp Gly
290                 295                 300

Val Leu Val Met Ala Glu Thr Phe Arg Ser Leu Arg Arg Gln Lys Ile
305                 310                 315                 320

Asp Ile Ser Arg Arg Gly Asn Ala Gly Asp Cys Leu Ala Asn Pro Ala
                325                 330                 335

Ala Pro Trp Gly Gln Gly Ile Asp Met Glu Arg Thr Leu Lys Gln Val
            340                 345                 350

Arg Ile Gln Gly Leu Thr Gly Asn Val Gln Phe Asp His Tyr Gly Arg
        355                 360                 365

Arg Val Asn Tyr Thr Met Asp Val Phe Glu Leu Lys Ser Thr Gly Pro
370                 375                 380

Arg Lys Val Gly Tyr Trp Asn Asp Met Asp Lys Leu Val Leu Ile Gln
385                 390                 395                 400

Asp Val Pro Thr Leu Gly Asn Asp Thr Ala Ala Ile Glu Asn Arg Thr
                405                 410                 415
```

-continued

```
Val Val Val Thr Thr Ile Met Glu Ser Pro Tyr Val Met Tyr Lys Lys
            420                 425                 430

Asn His Glu Met Phe Glu Gly Asn Asp Lys Tyr Glu Gly Tyr Cys Val
        435                 440                 445

Asp Leu Ala Ser Glu Ile Ala Lys His Ile Gly Ile Lys Tyr Lys Ile
    450                 455                 460

Ala Ile Val Pro Asp Gly Lys Tyr Gly Ala Arg Asp Ala Asp Thr Lys
465                 470                 475                 480

Ile Trp Asn Gly Met Val Gly Glu Leu Val Tyr Gly Lys Ala Glu Ile
                485                 490                 495

Ala Ile Ala Pro Leu Thr Ile Thr Leu Val Arg Glu Glu Val Ile Asp
            500                 505                 510

Phe Ser Lys Pro Phe Met Ser Leu Gly Ile Ser Ile Met Ile Lys Lys
        515                 520                 525

Pro Gln Lys Ser Lys Pro Gly Val Phe Ser Phe Leu Asp Pro Leu Ala
    530                 535                 540

Tyr Glu Ile Trp Met Cys Ile Val Phe Ala Tyr Ile Gly Val Ser Val
545                 550                 555                 560

Val Leu Phe Leu Val Ser Arg Phe Ser Pro Tyr Glu Trp His Thr Glu
                565                 570                 575

Glu Pro Glu Asp Gly Lys Glu Gly Pro Ser Asp Gln Pro Pro Asn Glu
            580                 585                 590

Phe Gly Ile Phe Asn Ser Leu Trp Phe Ser Leu Gly Ala Phe Met Gln
        595                 600                 605

Gln Gly Cys Asp Ile Ser Pro Arg Ser Leu Ser Gly Arg Ile Val Gly
    610                 615                 620

Gly Val Trp Trp Phe Phe Thr Leu Ile Ile Ile Ser Ser Tyr Thr Ala
625                 630                 635                 640

Asn Leu Ala Ala Phe Leu Thr Val Glu Arg Met Val Ser Pro Ile Glu
                645                 650                 655

Ser Ala Glu Asp Leu Ala Lys Gln Thr Glu Ile Ala Tyr Gly Thr Leu
            660                 665                 670

Asp Ser Gly Ser Thr Lys Glu Phe Phe Arg Arg Ser Lys Ile Ala Val
        675                 680                 685

Tyr Glu Lys Met Trp Thr Tyr Met Arg Ser Ala Glu Pro Ser Val Phe
    690                 695                 700

Thr Arg Thr Thr Ala Glu Gly Val Ala Arg Val Arg Lys Ser Lys Gly
705                 710                 715                 720

Lys Phe Ala Phe Leu Leu Glu Ser Thr Met Asn Glu Tyr Ile Glu Gln
                725                 730                 735

Arg Lys Pro Cys Asp Thr Met Lys Val Gly Gly Asn Leu Asp Ser Lys
            740                 745                 750

Gly Tyr Gly Val Ala Thr Pro Lys Gly Ser Ser Leu Gly Thr Pro Val
        755                 760                 765

Asn Leu Ala Val Leu Lys Leu Ser Glu Ala Gly Val Leu Asp Lys Leu
    770                 775                 780

Lys Asn Lys Trp Trp Tyr Asp Lys Gly Glu Cys Gly Pro Lys Asp Ser
785                 790                 795                 800

Gly Ser Lys Asp Lys Thr Ser Ala Leu Ser Leu Ser Asn Val Ala Gly
                805                 810                 815

Val Phe Tyr Ile Leu Val Gly Gly Leu Gly Leu Ala Met Leu Val Ala
            820                 825                 830

Leu Ile Glu Phe Cys Tyr Lys Ser Arg Ala Glu Ala Lys Arg Met Lys
```

```
                    835                 840                 845
Leu Thr Phe Ser Glu Ala Ile Arg Asn Lys Ala Arg Leu Ser Ile Thr
    850                 855                 860

Gly Ser Val Gly Glu Asn Gly Arg Val Leu Thr Pro Asp Cys Pro Lys
865                 870                 875                 880

Ala Val His Thr Gly Thr Ala Ile Arg Gln Ser Ser Gly Leu Ala Val
                885                 890                 895

Ile Ala Ser Asp Leu Pro
            900

<210> SEQ ID NO 8
<211> LENGTH: 918
<212> TYPE: PRT
<213> ORGANISM: Homo sapiens

<400> SEQUENCE: 8

Met Glu His Gly Thr Leu Leu Ala Gln Pro Gly Leu Trp Thr Arg Asp
1               5                   10                  15

Thr Ser Trp Ala Leu Leu Tyr Phe Leu Cys Tyr Ile Leu Pro Gln Thr
            20                  25                  30

Ala Pro Gln Val Leu Arg Ile Gly Gly Ile Phe Glu Thr Val Glu Asn
        35                  40                  45

Glu Pro Val Asn Val Glu Glu Leu Ala Phe Lys Phe Ala Val Thr Ser
    50                  55                  60

Ile Asn Arg Asn Arg Thr Leu Met Pro Asn Thr Thr Leu Thr Tyr Asp
65                  70                  75                  80

Ile Gln Arg Ile Asn Leu Phe Asp Ser Phe Glu Ala Ser Arg Arg Ala
                85                  90                  95

Cys Asp Gln Leu Ala Leu Gly Val Ala Ala Leu Phe Gly Pro Ser His
            100                 105                 110

Ser Ser Ser Val Ser Ala Val Gln Ser Ile Cys Asn Ala Leu Glu Val
        115                 120                 125

Pro His Ile Gln Thr Arg Trp Lys His Pro Ser Val Asp Asn Lys Asp
    130                 135                 140

Leu Phe Tyr Ile Asn Leu Tyr Pro Asp Tyr Ala Ala Ile Ser Arg Ala
145                 150                 155                 160

Ile Leu Asp Leu Val Leu Tyr Tyr Asn Trp Lys Thr Val Thr Val Val
                165                 170                 175

Tyr Glu Asp Ser Thr Gly Leu Ile Arg Leu Gln Glu Leu Ile Lys Ala
            180                 185                 190

Pro Ser Arg Tyr Asn Ile Lys Ile Lys Ile Arg Gln Leu Pro Ser Gly
        195                 200                 205

Asn Lys Asp Ala Lys Pro Leu Leu Lys Glu Met Lys Lys Gly Lys Glu
    210                 215                 220

Phe Tyr Val Ile Phe Asp Cys Ser His Glu Thr Ala Ala Glu Ile Leu
225                 230                 235                 240

Lys Gln Ile Leu Phe Met Gly Met Met Thr Glu Tyr Tyr His Tyr Phe
                245                 250                 255

Phe Thr Thr Leu Asp Leu Phe Ala Leu Asp Leu Glu Leu Tyr Arg Tyr
            260                 265                 270

Ser Gly Val Asn Met Thr Gly Phe Arg Leu Leu Asn Ile Asp Asn Pro
        275                 280                 285

His Val Ser Ser Ile Ile Glu Lys Trp Ser Met Glu Arg Leu Gln Ala
    290                 295                 300

Pro Pro Arg Pro Glu Thr Gly Leu Leu Asp Gly Met Met Thr Thr Glu
```

```
            305                 310                 315                 320
Ala Ala Leu Met Tyr Asp Ala Val Tyr Met Val Ala Ile Ala Ser His
                325                 330                 335

Arg Ala Ser Gln Leu Thr Val Ser Ser Leu Gln Cys His Arg His Lys
                340                 345                 350

Pro Trp Arg Leu Gly Pro Arg Phe Met Asn Leu Ile Lys Glu Ala Arg
                355                 360                 365

Trp Asp Gly Leu Thr Gly His Ile Thr Phe Asn Lys Thr Asn Gly Leu
                370                 375                 380

Arg Lys Asp Phe Asp Leu Asp Ile Ile Ser Leu Lys Glu Gly Thr
385                 390                 395                 400

Glu Lys Ala Ala Gly Glu Val Ser Lys His Leu Tyr Lys Val Trp Lys
                405                 410                 415

Lys Ile Gly Ile Trp Asn Ser Asn Ser Gly Leu Asn Met Thr Asp Ser
                420                 425                 430

Asn Lys Asp Lys Ser Ser Asn Ile Thr Asp Ser Leu Ala Asn Arg Thr
                435                 440                 445

Leu Ile Val Thr Thr Ile Leu Glu Glu Pro Tyr Val Met Tyr Arg Lys
                450                 455                 460

Ser Asp Lys Pro Leu Tyr Gly Asn Asp Arg Phe Glu Gly Tyr Cys Leu
465                 470                 475                 480

Asp Leu Leu Lys Glu Leu Ser Asn Ile Leu Gly Phe Ile Tyr Asp Val
                485                 490                 495

Lys Leu Val Pro Asp Gly Lys Tyr Gly Ala Gln Asn Asp Lys Gly Glu
                500                 505                 510

Trp Asn Gly Met Val Lys Glu Leu Ile Asp His Arg Ala Asp Leu Ala
                515                 520                 525

Val Ala Pro Leu Thr Ile Thr Tyr Val Arg Glu Lys Val Ile Asp Phe
                530                 535                 540

Ser Lys Pro Phe Met Thr Leu Gly Ile Ser Ile Leu Tyr Arg Lys Pro
545                 550                 555                 560

Asn Gly Thr Asn Pro Gly Val Phe Ser Phe Leu Asn Pro Leu Ser Pro
                565                 570                 575

Asp Ile Trp Met Tyr Val Leu Leu Ala Cys Leu Gly Val Ser Cys Val
                580                 585                 590

Leu Phe Val Ile Ala Arg Phe Thr Pro Tyr Glu Trp Tyr Asn Pro His
                595                 600                 605

Pro Cys Asn Pro Asp Ser Asp Val Val Glu Asn Asn Phe Thr Leu Leu
                610                 615                 620

Asn Ser Phe Trp Phe Gly Val Gly Ala Leu Met Gln Gln Gly Ser Glu
625                 630                 635                 640

Leu Met Pro Lys Ala Leu Ser Thr Arg Ile Val Gly Gly Ile Trp Trp
                645                 650                 655

Phe Phe Thr Leu Ile Ile Ile Ser Ser Tyr Thr Ala Asn Leu Ala Ala
                660                 665                 670

Phe Leu Thr Val Glu Arg Met Glu Ser Pro Ile Asp Ser Ala Asp Asp
                675                 680                 685

Leu Ala Lys Gln Thr Lys Ile Glu Tyr Gly Ala Val Arg Asp Gly Ser
                690                 695                 700

Thr Met Thr Phe Phe Lys Lys Ser Lys Ile Ser Thr Tyr Glu Lys Met
705                 710                 715                 720

Trp Ala Phe Met Ser Ser Arg Gln Gln Thr Ala Leu Val Arg Asn Ser
                725                 730                 735
```

-continued

```
Asp Glu Gly Ile Gln Arg Val Leu Thr Thr Asp Tyr Ala Leu Leu Met
            740                 745                 750

Glu Ser Thr Ser Ile Glu Tyr Val Thr Gln Arg Asn Cys Asn Leu Thr
        755                 760                 765

Gln Ile Gly Gly Leu Ile Asp Ser Lys Gly Tyr Gly Val Gly Thr Pro
    770                 775                 780

Ile Gly Ser Pro Tyr Arg Asp Lys Ile Thr Ile Ala Ile Leu Gln Leu
785                 790                 795                 800

Gln Glu Glu Gly Lys Leu His Met Met Lys Glu Lys Trp Trp Arg Gly
                805                 810                 815

Asn Gly Cys Pro Glu Glu Asp Asn Lys Glu Ala Ser Ala Leu Gly Val
            820                 825                 830

Glu Asn Ile Gly Gly Ile Phe Ile Val Leu Ala Ala Gly Leu Val Leu
        835                 840                 845

Ser Val Phe Val Ala Ile Gly Glu Phe Ile Tyr Lys Ser Arg Lys Asn
    850                 855                 860

Asn Asp Ile Glu Gln Ala Phe Cys Phe Phe Tyr Gly Leu Gln Cys Lys
865                 870                 875                 880

Gln Thr His Pro Thr Asn Ser Thr Ser Gly Thr Thr Leu Ser Thr Asp
                885                 890                 895

Leu Glu Cys Gly Lys Leu Ile Arg Glu Glu Arg Gly Ile Arg Lys Gln
            900                 905                 910

Ser Ser Val His Thr Val
        915
```

<210> SEQ ID NO 9
<211> LENGTH: 908
<212> TYPE: PRT
<213> ORGANISM: Homo sapiens

<400> SEQUENCE: 9

```
Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190
```

```
Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ile Ile Glu Lys Trp Ser Met Glu Arg Leu Gln Ala Pro
290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
                340                 345                 350

Trp Arg Phe Gly Thr Arg Phe Met Ser Leu Ile Lys Glu Ala His Trp
            355                 360                 365

Glu Gly Leu Thr Gly Arg Ile Thr Phe Asn Lys Thr Asn Gly Leu Arg
        370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Ala Asn Gly
                485                 490                 495

Gln Trp Asn Gly Met Val Arg Glu Leu Ile Asp His Lys Ala Asp Leu
            500                 505                 510

Ala Val Ala Pro Leu Ala Ile Thr Tyr Val Arg Glu Lys Val Ile Asp
        515                 520                 525

Phe Ser Lys Pro Phe Met Thr Leu Gly Ile Ser Ile Leu Tyr Arg Lys
530                 535                 540

Pro Asn Gly Thr Asn Pro Gly Val Phe Ser Phe Leu Asn Pro Leu Ser
545                 550                 555                 560

Pro Asp Ile Trp Met Tyr Ile Leu Leu Ala Tyr Leu Gly Val Ser Cys
                565                 570                 575

Val Leu Phe Val Ile Ala Arg Phe Ser Pro Tyr Glu Trp Tyr Asn Pro
            580                 585                 590

His Pro Cys Asn Pro Asp Ser Asp Val Val Glu Asn Asn Phe Thr Leu
        595                 600                 605

Leu Asn Ser Phe Trp Phe Gly Val Gly Ala Leu Met Gln Gln Gly Ser
610                 615                 620
```

```
Glu Leu Met Pro Lys Ala Leu Ser Thr Arg Ile Val Gly Gly Ile Trp
625                 630                 635                 640

Trp Phe Phe Thr Leu Ile Ile Ile Ser Ser Tyr Thr Ala Asn Leu Ala
            645                 650                 655

Ala Phe Leu Thr Val Glu Arg Met Glu Ser Pro Ile Asp Ser Ala Asp
        660                 665                 670

Asp Leu Ala Lys Gln Thr Lys Ile Glu Tyr Gly Ala Val Glu Asp Gly
            675                 680                 685

Ala Thr Met Thr Phe Phe Lys Lys Ser Lys Ile Ser Thr Tyr Asp Lys
690                 695                 700

Met Trp Ala Phe Met Ser Ser Arg Arg Gln Ser Val Leu Val Lys Ser
705                 710                 715                 720

Asn Glu Glu Gly Ile Gln Arg Val Leu Thr Ser Asp Tyr Ala Phe Leu
                725                 730                 735

Met Glu Ser Thr Thr Ile Glu Phe Val Thr Gln Arg Asn Cys Asn Leu
            740                 745                 750

Thr Gln Ile Gly Gly Leu Ile Asp Ser Lys Gly Tyr Gly Val Gly Thr
        755                 760                 765

Pro Met Gly Ser Pro Tyr Arg Asp Lys Ile Thr Ile Ala Ile Leu Gln
            770                 775                 780

Leu Gln Glu Glu Gly Lys Leu His Met Met Lys Glu Lys Trp Trp Arg
785                 790                 795                 800

Gly Asn Gly Cys Pro Glu Glu Glu Ser Lys Glu Ala Ser Ala Leu Gly
                805                 810                 815

Val Gln Asn Ile Gly Gly Ile Phe Ile Val Leu Ala Ala Gly Leu Val
            820                 825                 830

Leu Ser Val Phe Val Ala Val Gly Glu Phe Leu Tyr Lys Ser Lys Lys
        835                 840                 845

Asn Ala Gln Leu Glu Lys Arg Ser Phe Cys Ser Ala Met Val Glu Glu
850                 855                 860

Leu Arg Met Ser Leu Lys Cys Gln Arg Arg Leu Lys His Lys Pro Gln
865                 870                 875                 880

Ala Pro Val Ile Val Lys Thr Glu Glu Val Ile Asn Met His Thr Phe
                885                 890                 895

Asn Asp Arg Arg Leu Pro Gly Lys Glu Thr Met Ala
            900                 905

<210> SEQ ID NO 10
<211> LENGTH: 919
<212> TYPE: PRT
<213> ORGANISM: Homo sapiens

<400> SEQUENCE: 10

Met Thr Ala Pro Trp Arg Arg Leu Arg Ser Leu Val Trp Glu Tyr Trp
1               5                   10                  15

Ala Gly Leu Leu Val Cys Ala Phe Trp Ile Pro Asp Ser Arg Gly Met
            20                  25                  30

Pro His Val Ile Arg Ile Gly Gly Ile Phe Glu Tyr Ala Asp Gly Pro
        35                  40                  45

Asn Ala Gln Val Met Asn Ala Glu Glu His Ala Phe Arg Phe Ser Ala
    50                  55                  60

Asn Ile Ile Asn Arg Asn Arg Thr Leu Leu Pro Asn Thr Thr Leu Thr
65                  70                  75                  80

Tyr Asp Ile Gln Arg Ile His Phe His Asp Ser Phe Glu Ala Thr Lys
                85                  90                  95
```

-continued

```
Lys Ala Cys Asp Gln Leu Ala Leu Gly Val Ala Ile Phe Gly Pro
                100                 105                 110
Ser Gln Gly Ser Cys Thr Asn Ala Val Gln Ser Ile Cys Asn Ala Leu
            115                 120                 125
Glu Val Pro His Ile Gln Leu Arg Trp Lys His Pro Leu Asp Asn
        130                 135                 140
Lys Asp Thr Phe Tyr Val Asn Leu Tyr Pro Asp Tyr Ala Ser Leu Ser
145                 150                 155                 160
His Ala Ile Leu Asp Leu Val Gln Tyr Leu Lys Trp Arg Ser Ala Thr
                165                 170                 175
Val Val Tyr Asp Asp Ser Thr Gly Leu Ile Arg Leu Gln Glu Leu Ile
                180                 185                 190
Met Ala Pro Ser Arg Tyr Asn Ile Arg Leu Lys Ile Arg Gln Leu Pro
                195                 200                 205
Ile Asp Ser Asp Asp Ser Arg Pro Leu Leu Lys Glu Met Lys Arg Gly
        210                 215                 220
Arg Glu Phe Arg Ile Ile Phe Asp Cys Ser His Thr Met Ala Ala Gln
225                 230                 235                 240
Ile Leu Lys Gln Ala Met Ala Met Gly Met Met Thr Glu Tyr Tyr His
                245                 250                 255
Phe Ile Phe Thr Thr Leu Asp Leu Tyr Ala Leu Asp Leu Glu Pro Tyr
                260                 265                 270
Arg Tyr Ser Gly Val Asn Leu Thr Gly Phe Arg Ile Leu Asn Val Asp
            275                 280                 285
Asn Pro His Val Ser Ala Ile Val Glu Lys Trp Ser Met Glu Arg Leu
        290                 295                 300
Gln Ala Ala Pro Arg Ser Glu Ser Gly Leu Leu Asp Gly Val Met Met
305                 310                 315                 320
Thr Asp Ala Ala Leu Leu Tyr Asp Ala Val His Ile Val Ser Val Cys
                325                 330                 335
Tyr Gln Arg Ala Pro Gln Met Thr Val Asn Ser Leu Gln Cys His Arg
            340                 345                 350
His Lys Ala Trp Arg Phe Gly Gly Arg Phe Met Asn Phe Ile Lys Glu
        355                 360                 365
Ala Gln Trp Glu Gly Leu Thr Gly Arg Ile Val Phe Asn Lys Thr Ser
    370                 375                 380
Gly Leu Arg Thr Asp Phe Asp Leu Asp Ile Ile Ser Leu Lys Glu Asp
385                 390                 395                 400
Gly Leu Glu Lys Val Gly Val Trp Ser Pro Ala Asp Gly Leu Asn Ile
                405                 410                 415
Thr Glu Val Ala Lys Gly Arg Gly Pro Asn Val Thr Asp Ser Leu Thr
            420                 425                 430
Asn Arg Ser Leu Ile Val Thr Thr Val Leu Glu Glu Pro Phe Val Met
        435                 440                 445
Phe Arg Lys Ser Asp Arg Thr Leu Tyr Gly Asn Asp Arg Phe Glu Gly
    450                 455                 460
Tyr Cys Ile Asp Leu Leu Lys Glu Leu Ala His Ile Leu Gly Phe Ser
465                 470                 475                 480
Tyr Glu Ile Arg Leu Val Glu Asp Gly Lys Tyr Gly Ala Gln Asp Asp
                485                 490                 495
Lys Gly Gln Trp Asn Gly Met Val Lys Glu Leu Ile Asp His Lys Ala
            500                 505                 510
Asp Leu Ala Val Ala Pro Leu Thr Ile Thr His Val Arg Glu Lys Ala
```

```
            515                 520                 525
Ile Asp Phe Ser Lys Pro Phe Met Thr Leu Gly Val Ser Ile Leu Tyr
530                 535                 540

Arg Lys Pro Asn Gly Thr Asn Pro Ser Val Phe Ser Phe Leu Asn Pro
545                 550                 555                 560

Leu Ser Pro Asp Ile Trp Met Tyr Val Leu Leu Ala Tyr Leu Gly Val
                    565                 570                 575

Ser Cys Val Leu Phe Val Ile Ala Arg Phe Ser Pro Tyr Glu Trp Tyr
                580                 585                 590

Asp Ala His Pro Cys Asn Pro Gly Ser Glu Val Val Glu Asn Asn Phe
            595                 600                 605

Thr Leu Leu Asn Ser Phe Trp Phe Gly Met Gly Ser Leu Met Gln Gln
610                 615                 620

Gly Ser Glu Leu Met Pro Lys Ala Leu Ser Thr Arg Ile Ile Gly Gly
625                 630                 635                 640

Ile Trp Trp Phe Phe Thr Leu Ile Ile Ile Ser Ser Tyr Thr Ala Asn
                    645                 650                 655

Leu Ala Ala Phe Leu Thr Val Glu Arg Met Glu Ser Pro Ile Asp Ser
                660                 665                 670

Ala Asp Asp Leu Ala Lys Gln Thr Lys Ile Glu Tyr Gly Ala Val Lys
            675                 680                 685

Asp Gly Ala Thr Met Thr Phe Phe Lys Lys Ser Lys Ile Ser Thr Phe
690                 695                 700

Glu Lys Met Trp Ala Phe Met Ser Ser Lys Pro Ser Ala Leu Val Lys
705                 710                 715                 720

Asn Asn Glu Glu Gly Ile Gln Arg Ala Leu Thr Ala Asp Tyr Ala Leu
                    725                 730                 735

Leu Met Glu Ser Thr Thr Ile Glu Tyr Val Thr Gln Arg Asn Cys Asn
                740                 745                 750

Leu Thr Gln Ile Gly Gly Leu Ile Asp Ser Lys Gly Tyr Gly Ile Gly
            755                 760                 765

Thr Pro Met Gly Ser Pro Tyr Arg Asp Lys Ile Thr Ile Ala Ile Leu
770                 775                 780

Gln Leu Gln Glu Glu Asp Lys Leu His Ile Met Lys Glu Lys Trp Trp
785                 790                 795                 800

Arg Gly Ser Gly Cys Pro Glu Glu Asn Lys Glu Ala Ser Ala Leu
                    805                 810                 815

Gly Ile Gln Lys Ile Gly Gly Ile Phe Ile Val Leu Ala Ala Gly Leu
                820                 825                 830

Val Leu Ser Val Leu Val Ala Val Gly Glu Phe Val Tyr Lys Leu Arg
            835                 840                 845

Lys Thr Ala Glu Arg Glu Gln Arg Ser Phe Cys Ser Thr Val Ala Asp
850                 855                 860

Glu Ile Arg Phe Ser Leu Thr Cys Gln Arg Arg Val Lys His Lys Pro
865                 870                 875                 880

Gln Pro Pro Met Met Val Lys Thr Asp Ala Val Ile Asn Met His Thr
                    885                 890                 895

Phe Asn Asp Arg Arg Leu Pro Gly Lys Asp Ser Met Ala Cys Ser Thr
                900                 905                 910

Ser Leu Ala Pro Val Phe Pro
            915
```